(12) United States Patent
Eggenweiler et al.

(10) Patent No.: US 8,119,795 B2
(45) Date of Patent: *Feb. 21, 2012

(54) TRIAZOLE DERIVATIVES II

(75) Inventors: Hans-Michael Eggenweiler, Darmstadt (DE); Michael Wolf, Darmstadt (DE); Hans-Peter Buchstaller, Griesheim (DE); Christian Sirrenberg, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 351 days.

This patent is subject to a terminal disclaimer.

(21) Appl. No.: 12/301,140

(22) PCT Filed: Apr. 20, 2007

(86) PCT No.: PCT/EP2007/003478
§ 371 (c)(1),
(2), (4) Date: Nov. 17, 2008

(87) PCT Pub. No.: WO2007/134678
PCT Pub. Date: Nov. 29, 2007

(65) Prior Publication Data
US 2010/0022540 A1   Jan. 28, 2010

(30) Foreign Application Priority Data
May 18, 2006 (DE) .......... 10 2006 023 337

(51) Int. Cl.
*A61K 31/4196* (2006.01)
*C07D 503/12* (2006.01)
*C07D 249/12* (2006.01)
*C07D 401/12* (2006.01)

(52) U.S. Cl. ....... 544/33; 544/132; 544/366; 548/263.2; 546/272.4

(58) Field of Classification Search .......... None
See application file for complete search history.

(56) References Cited

U.S. PATENT DOCUMENTS
2008/0182857 A1*  7/2008  Eggenweiler et al. ... 514/254.05

FOREIGN PATENT DOCUMENTS
| WO | WO-2004 056782 A | 7/2004 |
| WO | WO-2005 000300 A | 1/2005 |
| WO | WO-2006 087077 A | 8/2006 |

OTHER PUBLICATIONS

Vippagunta et al. (Adv. Drug Deliv. Rev. 48: 3-26, 2001).*
International Search Report from PCT/EP2007/003478 dated Jul. 11, 2008.

* cited by examiner

*Primary Examiner* — Brandon Fetterolf
*Assistant Examiner* — Anna Pagonakis
(74) *Attorney, Agent, or Firm* — Millen, White, Zelano & Branigan, P.C.

(57) ABSTRACT

Novel triazole derivatives of the formula (I) in which $R^1$-$R^6$ and Y have the meanings indicated in Claim 1, are HSP90 inhibitors and can be used for the preparation of a medicament for the treatment of diseases in which the inhibition, regulation and/or modulation of HSP90 plays a role.

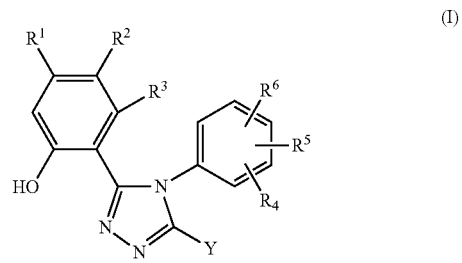

24 Claims, No Drawings

TRIAZOLE DERIVATIVES II

BACKGROUND OF THE INVENTION

The invention was based on the object of finding novel compounds having valuable properties, in particular those which can be used for the preparation of medicaments.

The present invention relates to compounds in which the inhibition, regulation and/or modulation of HSP90 plays a role, furthermore to pharmaceutical compositions which comprise these compounds, and to the use of the compounds for the treatment of diseases in which HSP90 plays a role.

The correct folding and conformation of proteins in cells is ensured by molecular chaperones and is critical for the regulation of the equilibrium between protein synthesis and degradation. Chaperones are important for the regulation of many central functions of cells, such as, for example, cell proliferation and apoptosis (Jolly and Morimoto, 2000; Smith et al., 1998; Smith, 2001).

Heat Shock Proteins (HSPs)

The cells of a tissue react to external stress, such as, for example, heat, hypoxia, oxidative stress, or toxic substances, such as heavy metals or alcohols, with activation of a number of chaperones which are known under the term "heat shock proteins" (HSPs).

The activation of HSPs protects the cell against damage initiated by such stress factors, accelerates the restoration of the physiological state and results in a stress-tolerant state of the cell.

Besides this originally discovered protective mechanism promoted by HSPs against external stress, further important chaperone functions have also been described in the course of time for individual HSPs under normal stress-free conditions. Thus, various HSPs regulate, for example, correct folding, intracellular localisation and function or regulated degradation of a number of biologically important proteins of cells.

HSPs form a gene family with individual gene products whose cellular expression, function and localisation differs in different cells. The naming and classification within the family is carried out on the basis of their molecular weight, for example HSP27, HSP70, and HSP90.

Some human diseases are based on incorrect protein folding (see review, for example, Tytell et al., 2001; Smith et al., 1998). The development of therapies which engages in the mechanism of the chaperone-dependent protein folding could therefore be useful in such cases. For example, incorrectly folded proteins result in aggregation of protein with neurodegenerative progression in the case of Alzheimer's disease, prion diseases or Huntington's syndrome. Incorrect protein folding may also result in loss of wild-type function, which can have the consequence of incorrectly regulated molecular and physiological function.

HSPs are also ascribed great importance in tumour diseases. There are, for example, indications that the expression of certain HSPs correlates with the stage of progression of tumours (Martin et al., 2000; Conroy et al., 1996; Kawanishi et al., 1999; Jameel et al., 1992; Hoang et al., 2000; Lebeau et al., 1991).

The fact that HSP90 plays a role in a number of central oncogenic signalling pathways in the cell and certain natural products having cancer-inhibiting activity target HSP90 has led to the concept that inhibition of the function of HSP90 would be sensible in the treatment of tumour diseases. An HSP90 inhibitor, 17-allylamino-17-demethoxygeldanamycin (17AAG), a derivative of geldanamycin, is currently undergoing clinical trials.

HSP90

HSP90 represents approximately 1-2% of the total cellular protein mass. It is usually in the form of a dimer in the cell and is associated with a multiplicity of proteins, so-called co-chaperones (see, for example, Pratt, 1997). HSP90 is essential for the vitality of cells (Young et al., 2001) and plays a key role in the response to cellular stress by interaction with many proteins whose native folding has been modified by external stress, such as, for example, heat shock, in order to restore the original folding or to prevent aggregation of the proteins (Smith et al., 1998).

There are also indications that HSP90 is of importance as buffer against the effects of mutations, presumably through correction of incorrect protein folding caused by the mutation (Rutherford and Lindquist, 1998).

In addition, HSP90 also has a regulatory importance. Under physiological conditions, HSP90, together with its homologue in the endoplasmatic reticulum, GRP94, plays a role in the cell balance for ensuring the stability of the conformation and maturing of various client key proteins. These can be divided into three groups: receptors for steroid hormones, Ser/Thr or tyrosine kinases (for example ERBB2, RAF-1, CDK4 and LCK) and a collection of various proteins, such as, for example, mutated p53 or the catalytic subunit of telomerase hTERT. Each of these proteins takes on a key role in the regulation of physiological and biochemical processes of cells.

The preserved HSP90 family in humans consists of four genes, cytosolic HSP90α, the inducible HSP90β isoform (Hickey et al., 1989), GRP94 in the endoplasmatic reticulum (Argon et al., 1999) and HSP75/TRAP1 in the mitochondrial matrix (Felts et al., 2000). It is assumed that all members of the family have a similar mode of action, but, depending on their localisation in the cell, bind to different client proteins. For example, ERBB2 is a specific client protein of GRP94 (Argon et al., 1999), while the type 1 receptor of tumour necrosis factor (TNFR1) or the retinoblastoma protein (Rb) have been found to be clients of TRAP1 (Song et al., 1995; Chen et al., 1996).

HSP90 is involved in a number of complex interactions with a large number of client proteins and regulatory proteins (Smith, 2001). Although precise molecular details have not yet been clarified, biochemical experiments and investigations with the aid of X-ray crystallography in recent years have increasingly been able to decipher details of the chaperone function of HSP90 (Prodromou et al., 1997; Stebbins et al., 1997). Accordingly, HSP90 is an ATP-dependent molecular chaperone (Prodromou et al, 1997), with dimerisation being important for ATP hydrolysis. The binding of ATP results in the formation of a toroidal dimer structure, in which the two N-terminal domains come into close contact with one another and act as a switch in the conformation (Prodromou and Pearl, 2000).

Known HSP90 Inhibitors

The first class of HSP90 inhibitors to be discovered were benzoquinone ansamycins with the compounds herbimycin A and geldanamycin. Originally, the reversion of the malignant phenotype in fibroblasts which had been induced by transformation with the v-Src oncogene was detected with them (Uehara et al., 1985).

Later, a strong antitumoural activity was demonstrated in vitro (Schulte et al., 1998) and in vivo in animal models (Supko et al., 1995).

Immune precipitation and investigations on affinity matrices then showed that the principal mechanism of action of geldanamycin involves binding to HSP90 (Whitesell et al., 1994; Schulte and Neckers, 1998). In addition, X-ray crystallographic studies have shown that geldanamycin competes for the ATP binding site and inhibits the intrinsic ATPase activity of HSP90 (Prodromou et al., 1997; Panaretou et al., 1998). This prevents the formation of the multimeric HSP90 complex, with its property of functioning as chaperone for client proteins. As a consequence, client proteins are degraded via the ubiquitin-proteasome pathway.

The geldanamycin derivative 17-allylamino-17-demethoxygeldanamycin (17AAG) showed an unchanged property in the inhibition of HSP90, the degradation of client proteins and antitumoural activity in cell cultures and in xenograft tumour models (Schulte et al, 1998; Kelland et al, 1999), but had significantly lower liver cytotoxicity than geldanamycin (Page et all 1997). 17AAG is currently undergoing phase I/II clinical trials.

Radicicol, a macrocyclic antibiotic, likewise exhibited revision of the v-Src and v-Ha-Ras-induced malignant phenotype of fibroblasts (Kwon et all 1992; Zhao et al, 1995). Radicicol degrades a large number of signal proteins as a consequence of HSP90 inhibition (Schulte et al., 1998). X-ray crystallographic studies have shown that radicicol likewise binds to the N-terminal domain of HSP90 and inhibits the intrinsic ATPase activity (Roe et al., 1998).

Antibiotics of the coumarine type, as is known, bind to the ATP binding site of the HSP90 homolog DNA gyrase in bacteria. The coumarine, Novobiocin, binds to the carboxy-terminal end of HSP90, i.e. to a different site in HSP90 than the benzoquinone-ansamycins and radicicol, which bind to the N-terminal end of HSP90 (Marcu et al., 2000b).

The inhibition of HSP90 by novobiocin results in degradation of a large number of HSP90-dependent signal proteins (Marcu et al., 2000a).

The degradation of signal proteins, for example ERBB2, was demonstrated using PU3, an HSP90 inhibitor derived from purines. PU3 causes cell cycle arrest and differentiation in breast cancer cell lines (Chiosis et al., 2001).

HSP90 as Therapeutic Target

Due to the participation of HSP90 in the regulation of a large number of signalling pathways which have crucial importance in the phenotype of a tumour, and the discovery that certain natural products exert their biological effect through inhibition of the activity of HSP90, HSP90 is currently being tested as a novel target for the development of a tumour therapeutic agent (Neckers et al., 1999).

The principal mechanism of action of geldanamycin, 17AAG, and radicicol includes the inhibition of the binding of ATP to the ATP binding site at the N-terminal end of the protein and the resultant inhibition of the intrinsic ATPase activity of HSP90 (see, for example, Prodromou et al., 1997; Stebbins et al., 1997; Panaretou et al., 1998). Inhibition of the ATPase activity of HSP90 prevents the recruitment of co-chaperones and favours the formation of an HSP90 heterocomplex, which causes client proteins to undergo degradation via the ubiquitin-proteasome pathway (see, for example, Neckers et al., 1999; Kelland et al., 1999). The treatment of tumour cells with HSP90 inhibitors results in selective degradation of important proteins having fundamental importance for processes such as cell proliferation, regulation of the cell cycle and apoptosis. These processes are frequently deregulated in tumours (see, for example, Hostein et al., 2001). An attractive rationale for the development of an inhibitor of HSP90 is that a strong tumour-therapeutic action can be achieved by simultaneous degradation of a plurality of proteins which are associated with the transformed phenotype.

In detail, the present invention relates to compounds which inhibit, regulate and/or modulate HSP90, to compositions which comprise these compounds, and to methods for the use thereof for the treatment of HSP90-induced diseases, such as tumour diseases, viral diseases, such as, for example, hepatitis B (Waxman, 2002); immune suppression in transplants (Bijlmakers, 2000 and Yorgin, 2000); inflammation-induced diseases (Bucci, 2000), such as rheumatoid arthritis, asthma, multiple sclerosis, type 1 diabetes, lupus erythematosus, psoriasis and inflammatory bowel disease; cystic fibrosis (Fuller, 2000); diseases associated with angiogenesis (Hur, 2002 and Kurebayashi, 2001), such as, for example, diabetic retinopathy, haemangiomas, endometriosis and tumour angiogenesis; infectious diseases; autoimmune diseases; ischaemia; promotion of nerve regeneration (Rosen et al., WO 02/09696; Degranco et al., WO 99/51223; Gold, U.S. Pat. No. 6,210,974 B1); fibrogenetic diseases, such as, for example, dermatosclerosis, polymyositis, systemic lupus, cirrhosis of the liver, keloid formation, interstitial nephritis and pulmonary fibrosis (Strehlow, WO 02/02123).

The invention also relates to the use of the compounds according to the invention for the protection of normal cells against toxicity caused by chemotherapy, and to the use in diseases where incorrect protein folding or aggregation is a principal causal factor, such as, for example, scrapie, Creutzfeldt-Jakob disease, Huntington's or Alzheimer's (Sittler, Hum. Mol. Genet., 10, 1307, 2001; Tratzelt et al., Proc. Nat. Acad. Sci., 92, 2944, 1995; Winklhofer et al., J. Biol. Chem., 276, 45160, 2001). WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous cell carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy-chain disease.

A. Kamal et al. in Trends in Molecular Medicine, Vol. 10 No. 6 Jun. 2004, describe therapeutic and diagnostic applications of HSP90 activation, inter alia for the treatment of diseases of the central nervous system and of cardiovascular diseases.

The identification of small compounds which specifically inhibit, regulate and/or modulate HSP90 is therefore desirable and an aim of the present invention.

It has been found that the compounds of the formula I and salts thereof have very valuable pharmacological properties while being well tolerated. In particular, they exhibit HSP90-inhibiting properties.

The present invention therefore relates to compounds of the formula I as medicaments and/or medicament active ingredients in the treatment and/or prophylaxis of the said diseases and to the use of compounds of the formula I for the preparation of a pharmaceutical for the treatment and/or prophylaxis of the said diseases and also to a process for the treatment of the said diseases which comprises the administration of one or more compounds of the formula I to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

PRIOR ART

WO 2005/00300 A1 describes other triazole derivatives as HSP90 inhibitors.

WO 00/53169 describes HSP90 inhibition with coumarine or a coumarine derivative.

WO 03/041643 A2 discloses HSP90-inhibiting zearalanol derivatives. HSP90-inhibiting pyrazole derivatives which are substituted by an aromatic radical in the 3- or 5-position are disclosed in WO 2004/050087 A1 and WO 2004/056782 A1.

WO 03/055860 A1 describes 3,4-diarylpyrazoles as HSP90 inhibitors. Purine derivatives having HSP90-inhibiting properties are disclosed in WO 02/36075 A2.

WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous cell carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy-chain disease.

WO 01/72779 furthermore discloses the use of the compounds mentioned therein for the treatment of viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, equinovirus, arbovirus, huntavirus, Coxsackie virus, mumps virus, measles virus, rubella virus, polio virus, human immunodeficiency virus type I (HIV-I) and human immunodeficiency virus type II (HIV-II). WO 01/72779 furthermore describes the use of the compounds mentioned therein for GRP94 modulation, where the modulated biological GRP94 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Finally, WO 01/72779 describes the use of an effective amount of a GRP94 protein modulator for the preparation of a medicament for changing a subsequent cellular reaction to an ischaemic state in a tissue site in an individual, by treatment of the cells at the tissue site with the GRP94 protein modulator in order that the GRP94 activity in cells is increased to such an extent that a subsequent cellular reaction to an ischaemic state is changed, where the subsequent ischaemic condition is preferably the consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress, or where the tissue site is the donor tissue for a transplant.

The specifications mentioned below describe combinations of the HSP90 inhibitor geldanamycin with other medicament active ingredients:
WO 2004/108080 A2, WO 2005/002506 A2, WO 2005/000211 A2, WO 2005/000212 A2, WO 2005/000213 A2, WO 2005/000214 A2, WO 2005/000314 A1.

FURTHER LITERATURE

Argon Y and Simen B B. 1999 "Grp94, an ER chaperone with protein and peptide binding properties", Semin. Cell Dev. Biol., Vol. 10, pp. 495-505.

Bijlmakers M-J J E, Marsh M. 2000 "Hsp90 is essential for the synthesis and subsequent membrane association, but not the maintenance, of the Src-kinase p56lck", Mol. Biol. Cell, Vol. 11 (5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", Brit. J. Pharmacol., Vol 131 (1), pp. 13-16.

Carreras C W, Schirmer A, Zhong Z, Santi V S. 2003 "Filter binding assay for the geldanamycin-heat shock protein 90 interaction", Analytical Biochem., Vol 317, pp 40-46.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", Mol. Cell. Biol., Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", Chem. Biol., Vol. 8, pp. 289-299.

Chiosis G, Lucas B, Shtil A, Huezo H, Rosen N 2002 "Development of a purine-scaffold novel class of HSP90 binders that inhibit the proliferation of cancer cells and induce the degradation of her2 tyrosine kinase". Bioorganic Med. Chem., Vol 10, pp 3555-3564.

Conroy S E and Latchman D S. 1996 "Do heat shock proteins have a role in breast cancer?", Brit. J. Cancer, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", J. Biol. Chem., Vol. 5, pp. 3305-331 2.

Fuller W, Cuthbert A W. 2000 "Post-translational disruption of the delta F508 cystic fibrosis transmembrane conductance regulator (CFTR)-molecular Chaperone complex with geldanamycin stabilises delta F508 CFTR in the rabbit reticulocyte lysate", J. Biol. Chem., Vol. 275(48), pp. 37462-37468.

Hickey E, Brandon S E, Smale G, Lloyd D and Weber L A. 1999 "Sequence and regulation of a gene encoding a human 89-kilodalton heat shock protein", Mol. Cell. Biol., Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor 1 (HSF1) and prostate adenocarcinoma, Am. J. Pathol., Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", Cancer Res., Vol. 61, pp. 4003-4009.

Hur E, Kim H-H, Choi S M, Kim J H, Yim S, Kwon H J, Choi Y, Kim D K, Lee M-0, Park H. 2002 "Reduction of hypoxia-induced transcription through the repression of hypoxia-inducible factor-1α/aryl hydrocarbon receptor nuclear translocator DNA binding by the 90-kDa heatshock protein inhibitor radicicol", Mol. Pharmacol., Vol 62(5), pp. 975-982.

Jameel A, Skilton R A, Campbell T A, Chander S K, Coombes R C and Luqmani Y A. 1992 "Clinical Jolly C and Morimoto R I. 2000 "Role of the heat shock response and molecular chaperones in oncogenesis and cell death", J. Natl. Cancer Inst., Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", Cancer, Vol. 85, pp. 1649-1657.

Kelland L R, Abel G, McKeage M J, Jones M, Goddard P M, Valenti M, Murrer B A, and Harrap K R. 1993 "Preclinical antitumour evaluation of bisacetalo-amino-dichloro-cyclohexylamine platinum (IV): an orally active platinum drug", Cancer Research, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", J. Natl. Cancer Inst., Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", Jap. J. Cancer Res., Vol. 92(12), 1342-1351.

Kwon H J, Yoshida M, Abe K, Horinouchi S and Bepple T. 1992 "Radicicol, an agent inducing the reversal of transformed phentoype of src-transformed fibroblasts, Biosci., Biotechnol., Biochem., Vol. 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJE24 Harveyras oncogene", Oncogene, Vol. 6, pp. 1125-1132.

Marcu M G, Chadli A, Bouhouche I, Catelli M and Neckers L. 2000a "The heat shock protein 90 antagonist novobiocin interacts with a previously unrecognised ATP-binding domain in the carboxyl terminus of the chaperone", J. Biol. Chem., Vol. 275, pp. 37181-37186.

Marcu M G, Schulte T W and Neckers L. 2000b "Novobiocin and related coumarins and depletion of heat shock protein 90-dependent signaling proteins", J. Natl. Cancer Inst., Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", Cancer Res., Vol. 60, pp. 2232-2238.

Neckers L, Schulte T W and Momnaaugh E. 1999 "Geldanamycin as a potential anti-cancer agent: its molecular target and biochemical activity", Invest. New Drugs, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", Proc. Am. Assoc. Cancer Res., Vol. 38, pp. 308.

Panaretou B, Prodromou C, Roe S M, OBrien R, Ladbury J E, Piper P W and Pearl L H. 1998 "ATP binding and hydrolysis are essential to the function of the HSP90 molecular chaperone in vivo", EMBO J., Vol. 17, pp. 4829-4836.

Pratt W B. 1997 "The role of the HSP90-based chaperone system in signal transduction by nuclear receptors and receptors signalling via MAP kinase", Annu. Rev. Pharmacol. Toxicol., Vol. 37, pp. 297-326.

Prodromou C, Roe S M, O'Brien R, Ladbury J E, Piper P W and Pearl L H. 1997 "Identification and structural characterisation of the ATP/ADP-binding site in the HSP90 molecular chaperone", Cell, Vol. 90, pp. 65-75.

Prodromou C, Panaretou B, Chohan S, Siligardi G, O'Brien R, Ladbury J E, Roe S M, Piper P W and Pearl L H. 2000 "The ATPase cycle of HSP90 drives a molecular "clamp" via transient dimerisation of the N-terminal domains", EMBO J., Vol. 19, pp. 4383-4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", J. Med. Chem., Vol. 42, pp. 260-266.

Rutherford S L and Lindquist S. 1998 "HSP90 as a capacitor for morphological evolution. Nature, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", Mol. Endocrinology, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", Cell Stress and Chaperones, Vol. 3, pp. 100-108.

Schulte T W and Neckers L M. 1998 "The benzoquinone ansamycin 17-allylamino-17-demethoxygeldanamcyin binds to HSP90 and shares important biologic activities with geldanamycin", Cancer Chemother. Pharmacol., Vol. 42, pp. 273-279.

Smith D F. 2001 "Chaperones in signal transduction", in: Molecular chaperones in the cell (P Lund, ed.; Oxford University Press, Oxford and NY), pp. 165-178.

Smith D F, Whitesell L and Katsanis E. 1998 "Molecular chaperones: Biology and prospects for pharmacological intervention", Pharmacological Reviews, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", J. Biol. Chem., Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", Cell, Vol. 89, pp. 239-250.

Supko J G, Hickman R L, Grever M R and Malspeis L. 1995 "Preclinical pharmacologic evaluation of geldanamycin as an antitumour agent", Cancer Chemother. Pharmacol., Vol. 36, pp. 305-315.

Tytell M and Hooper P L. 2001 "Heat shock proteins: new keys to the development of cytoprotective therapies", Emerging Therapeutic Targets, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", Mol. Cell. Biol., Vol. 6, pp. 21 98-2206.

Waxman, Lloyd H. Inhibiting hepatitis C virus processing and replication. (Merck & Co., Inc., USA). PCT Int. Appl. (2002), WO 0207761

Whitesell L, Mimnaugh E G, De Costa B, Myers C E and Neckers L M. 1994 "Inhibition of heat shock protein HSP90-pp 60v-src heteroprotein complex formation by benzoquinone ansamycins: essential role for stress proteins in oncogenic transformation", Proc. Natl. Acad. Sci. USA., Vol. 91, pp. 8324-8328.

Yorgin et al. 2000 "Effects of geldanamycin, a heat-shock protein 90-binding agent, on T cell function and T cell nonreceptor protein tyrosine kinases", J. Immunol., Vol 164(6), pp. 2915-2923.

Young J C, Moarefi I and Hartl F U. 2001 "HSP90: a specialised but essential protein-folding tool", J. Cell. Biol., Vol. 154, pp. 267-273.

Zhao J F, Nakano H and Sharma S. 1995 "Suppression of RAS and MOS transformation by radicicol", Oncogene, Vol. 11, pp. 161-173.

SUMMARY OF THE INVENTION

The invention relates to compounds of the formula I

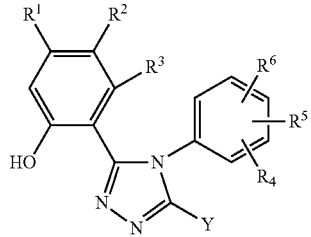

in which $R^1$ denotes OH, $OCH_3$, $OCF_3$, $OCHF_2$, OBzl, OAc, p-methoxybenzyloxy, SH, $S(O)_mCH_3$, $SO_2NH_2$, Hal, $CF_3$ or $CH_3$, $R^2$ denotes $CONA[(CH_2)_oAr]$, $CONA[(CH_2)_oHet']$, $SO_2NA[(CH_2)_oAr']$ or $SO_2NA[(CH_2)_oHet']$, $R^3$ denotes H, Hal, CN, $NO_2$, A, Alk, $(CH_2)_oAr$, $(CH_2)_oHet'$, COOH, COOA, COOAr, COOHet', $CONH_2$, CONHA, CONAA', CONHAr, CONAAr, $CON(Ar)_2$, CONHHet', $CON(Het')_2$, $NH_2$, NHA, NHAr, NHHet', NAA', NHCOA, NACOA', NHCOAr, NHCOHet', NHCOOA, NHCOOAr, NHCOOHet', NHCONHA, NHCONHAr, NHCONHHet', OH, OA, OAr, OHet', SH, $S(O)_mA$, $S(O)_mAr$, $S(O)_mHet'$, $SO_2NH_2$, $SO_2NHA$, $SO_2NAA'$, $SO_2NHAr$, $SO_2NAAr$, $SO_2NHHet'$, $SO_2NAHet'$, $SO_2NA$-benzyl, $SO_2N(Ar)_2$ or $SO_2N(Het')_2$, $R^4$, $R^5$, $R^6$ each, independently of one another, denote H, Hal, CN, $NO_2$, A, Alk, $(CH_2)_nAr$, $(CH_2)_nHet'$, COOH, COOA, COOAr, COOHet', $CONH_2$, CONHA, CONAA', CONHAr, CONAAr, $CON(Ar)_2$, CONHHet', $CON(Het')_2$, $NH_2$, NHA, NHAr, NHHet', NAA', NHCOA, $NHCONH_2$, NACOA', $NHCO(CH_2)_nAr$, NHCOHet', NHCOOA, NHCOOAr, NHCOOHet', NHCONHA, NHCONHAr, NHCONHHet', OH, OA, $O(CH_2)_oHet$, $O(CH_2)_oNH_2$, $O(CH_2)_oCN$, OAr, OHet', SH, $S(O)_mA$, $S(O)_mAr$, $S(O)_mHet'$, $SO_2NH_2$, $SO_2NHA$, $SO_2NAA'$, $SO_2NHAr$, $SO_2NAAr$, $SO_2NHHet'$, $SO_2N(Ar)_2$ or $SO_2N(Het')_2$, $R^4$ and $R^5$ together also denote $OCH_2O$, $OCH_2CH_2O$, —CH=CH—CH=CH—, NH—CH=CH or CH=CH—NH, Y denotes OH or SH, A, A' each, independently of one another, denote unbranched or branched alkyl having 1-10 C atoms, in which one, two or three $CH_2$ groups may be replaced by O, S, SO, $SO_2$, NH, $NR^8$ and/or by —CH=CH— groups and/or in addition 1-5H atoms may be replaced by F, Cl, Br and/or $R^7$, Alk or cyclic alkyl having 3-7 C atoms, A and A' together also denote an alkylene chain having 2, 3, 4, 5 or 6 C atoms, in which a $CH_2$ group may be replaced by O, S, SO, $SO_2$, N, NH, $NR^8$, $NCOR^8$ or $NCOOR^8$, Alk denotes alkenyl having 2-6 C atoms, $R^7$ denotes CN, $COOR^9$, $CONR^9R^{10}$, $NR^9R^{10}$, $NHCOR^9$, $NHCOOR^9$ or $OR^9$, $R^8$ denotes cycloalkyl having 3-7 C atoms, cycloalkylalkylene having 4-10 C atoms, Alk or
unbranched or branched alkyl having 1-6 C atoms, in which one, two or three $CH_2$ groups may be replaced by O, S, SO, $SO_2$, NH and/or in addition 1-5H atoms may be replaced by F and/or Cl, $R^9$, $R^{10}$ each, independently of one another, denote H or alkyl having 1-5 C atoms, in which 1-3 $CH_2$ groups may be replaced by O, S, SO, $SO_2$, NH, NMe or NEt and/or in addition 1-5H atoms may be replaced by F and/or Cl, $R^9$ and $R^{10}$ together also denote an alkylene chain having 2, 3, 4, 5 or 6 C atoms, in which a $CH_2$ group may be replaced by O, S, SO, $SO_2$, NH, $NR^8$, $NCOR^8$ or $NCOOR^8$, Ar denotes phenyl, naphthyl or biphenyl, each of which is unsubstituted or mono-, di- or trisubstituted by Hal, A, $XR^7$, Y, CN, phenyl, Het'', OXHet''', OA, $OXR^7$, $S(O)_mA$, $S(O)_mXR^7$, $NO_2$, $NH_2$, $NR^9R^{10}$, $NR^8R^9$, $CONR^9R^{10}$, $CONR^8R^9$, $SO_2NR^9R^{10}$, $SO_2NR^8R^9$, $NR^9COR^{10}$, $NR^9CONR^9R^{10}$ and/or $NR^9SO_2R^{10}$, Ar' denotes phenyl, naphthyl or biphenyl, each of which is mono-, di- or trisubstituted by Hal, A, $XR^7$, $XR^4$, Y, CN, Ar, Het, OA, $OXR^7$, $OXR^4$, $S(O)_mA$, $S(O)_mXR^7$, $S(O)_mXR^4$, $NO_2$, $NH_2$, $NR^9R^{10}$, $NR^8R^9$, $CONR^9R^{10}$, $CONR^8R^9$, $SO_2NR^9R^{10}$, $SO_2NR^8R^9$, $NR^9COR^{10}$, $NR^9CONR^9R^{10}$ and/or $NR^9SO_2R^{10}$, Het denotes a mono- or bicyclic saturated, unsaturated or aromatic heterocycle having 1 to 4 N, O and/or S atoms, which may be unsubstituted or mono-, di- or trisubstituted by Hal, A, $XR^7$, Y, CN, Ar, OA, $OXR^7$, $S(O)_mA$, $S(O)_{gr}XR^7$, $NO_2$, $NH_2$, $NR^9R^{10}$, $NR^8R^9$, $CONR^9R^{10}$, $CONR^8R^9$, $SO_2NR^9R^{10}$, $SO_2NR^8R^9$, $NR^9COR^{10}$, $NR^9CONR^9R^{10}$, $NR^9SO_2R^{10}$, =S, =$NR^{11}$, =$NR^{11}R^7$ and/or =O (carbonyl oxygen), Het' denotes a mono- or bicyclic saturated, unsaturated or aromatic heterocycle having 1 to 4 N, O and/or S atoms, which may be unsubstituted or mono-, di- or trisubstituted by Hal, A, $XR^7$, $XR^4$, Y, CN, Ar, Het, OA, $OXR^7$, $OXR^4$, $S(O)_mA$, $S(O)_mXR^7S(O)_mXR^4$, $NO_2$, $NH_2$, $NR^9R^{10}$, $NR^8R^9$, $CONR^9R^{10}$, $CONR^8R^9$, $SO_2NR^9R^{10}$, $SO_2NR^8R^9$, $NR^9COR^{10}$, $NR^9CONR^9R^{10}$, $NR^9SO_2R^{10}$, =S, =$NR^{11}$, =$NR^{11}R^7$ and/or =O (carbonyl oxygen), and/or in which a ring nitrogen may be substituted by —O⁻, Het" denotes a monocyclic aromatic heterocycle having 1 to 3 N, O and/or S atoms, Het''' denotes a monocyclic saturated heterocycle having 1 to 3 N, O and/or S atoms, X denotes unbranched or branched alkylene having 1-10 C atoms, in which one, two or three $CH_2$ groups may be replaced by O, S, SO, $SO_2$, NH, $NR^8$ and/or by —CH=CH— groups and/or in addition 1-5H atoms may be replaced by F, Cl, Br and/or $R^7$, $R^{11}$ denotes H or A, Hal denotes F, Cl, Br or I, m denotes 0, 1 or 2, n denotes 0, 1, 2, 3 or 4, o denotes 1, 2 or 3, and pharmaceutically usable salts, tautomers and stereoisomers thereof, including mixtures thereof in all ratios.

The invention relates to the compounds of the formula I and salts thereof and to a process for the preparation of compounds of the formula I and pharmaceutically usable derivatives, solvates, salts, tautomers and stereoisomers thereof, characterised in that a) a compound of the formula II

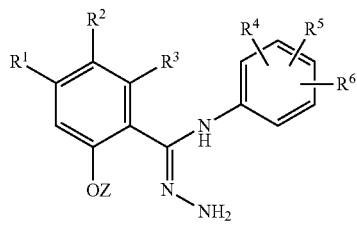

II in which
$R^1$, $R^2$, $R^3$, $R^4$, $R^5$ and $R^6$ have the meanings indicated in Claim 1, where $NH_2$ and/or OH groups are in protected form, and
Z denotes a hydroxyl-protecting group,
is reacted with
a compound of the formula III

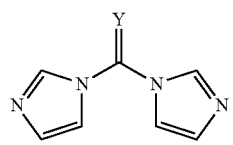

III in which Y denotes O or S,
and subsequently the protecting groups are removed,
or b) a compound of the formula IV

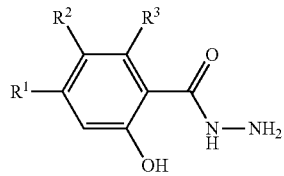

IV in which $R^1$, $R^2$ and $R^3$ have the meanings indicated in Claim 1,
is reacted with
a compound of the formula V

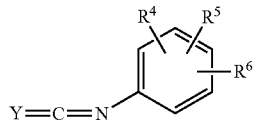

V in which $R^4$, $R^5$ and $R^6$ have the meanings indicated in Claim 1 and Y denotes O or S, to give thiosemicarbazide derivatives, and the latter are subsequently cyclised, and/or in that one or more radical(s) $R^1$, $R^2$, $R^3$, $R^4$, $R^5$ and/or $R^6$ in a compound of the formula I are converted into one or more radical(s) $R^1$, $R^2$, $R^3$, $R^4$, $R^5$ and/or $R^6$ by, for example, i) reducing a nitro group to an amino group, ii) hydrolysing an ester group to a carboxyl group, iii) converting an amino group into an alkylated amine by reductive amination, iv) converting an acid chloride into an amide, and/or a base or acid of the formula I is converted into one of its salts.

The invention also relates to the hydrates and solvates of these compounds. solvates of the compounds are taken to mean adductions of inert solvent molecules onto the compounds which form owing to their mutual attractive force. solvates are, for example, mono- or dihydrates or alcoholates.

The compounds of the formula I according to the invention may also exist in the tautomeric form of the formula Ia

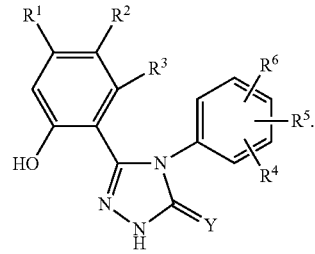

Ia

Pharmaceutically usable derivatives are taken to mean, for example, the salts of the compounds according to the invention and also so-called prodrug compounds.

Prodrug derivatives are taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The expression "effective amount" means the amount of a medicament or pharmaceutical active ingredient which causes a biological or medical response which is sought or desired, for example, by a researcher or physician in a tissue, system, animal or human.

In addition, the expression "therapeutically effective amount" means an amount which, compared with a corresponding subject who has not received this amount, has the following consequence:
improved healing treatment, healing, prevention or elimination of a disease, a disease picture, a disease state, a complaint, a disorder or of side effects or also the reduction in the progress of a disease, a complaint or a disorder.

The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, their meanings are independent of one another.

Above and below, the radicals and parameters $R^1$, $R^2$, $R^3$, $R^4$, $R^5$ and $R^6$ have the meanings indicated for the formula I, unless expressly indicated otherwise.

A or A' preferably denotes alkyl, is unbranched (linear) or branched, and has 1, 2, 3, 4, 5, 6, 7, 8, 9 or 10 C atoms. A or A' particularly preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1, 2- or 1,2,2-trimethylpropyl.

A or A' very particularly preferably denotes alkyl having 1, 2, 3, 4, 5 or 6 C atoms, preferably ethyl, propyl, isopropyl, butyl, isobutyl, sec-butyl, tert-butyl, pentyl, hexyl, trifluoromethyl, pentafluoroethyl or 1,1,1-trifluoroethyl, furthermore also fluoromethyl, difluoromethyl or bromomethyl.

A or A' also denotes cycloalkyl. Cycloalkyl preferably denotes cyclopropyl, cyclobutyl, cyclopentyl, cyclohexyl or cycloheptyl.

A or A' also denotes Alk. Alk denotes alkenyl having 2-6 C atoms, such as, for example, vinyl or propenyl.

Cycloalkylalkylene denotes, for example, cyclohexylmethyl, cyclohexylethyl, cyclopentylmethyl or cyclopentylethyl.

Ac denotes acetyl, Bzl denotes benzyl, Ms denotes —$SO_2CH_3$.

$R^1$ preferably denotes OH, $OCH_3$ or SH, particularly preferably OH or $OCH_3$, furthermore also $OCF_3$, $OCHF_2$.

$R^2$ preferably denotes $CONA[(CH_2)_oAr]$, $CONA[(CH_2)_oHet']$, $SO_2NA[(CH_2)_oAr']$ or $SO_2NA[(CH_2)_oHet']$, where A denotes alkyl having 1, 2, 3 or 4 C atoms.

$R^2$ particularly preferably denotes $CON(CH_3)CH_2Ar$, $CON(CH_3)CH_2Het'$, $SO_2N(CH_3)CH_2Ar'$ or $SO_2N(CH_3)CH_2Het'$.

$R^3$ particularly preferably denotes H.

$R^4$, $R^5$, $R^6$ preferably each, independently of one another, denote H, Hal, CN, A, $O(CH_2)_oHet'$, $O(CH_2)_oCN$, $(CH_2)_oNH_2$, $(CH_2)_oNHA$ or $(CH_2)_oNAA'$;

$R^4$ and $R^5$ preferably denote H.

$R^6$ preferably denotes H, Hal, CN, A, $O(CH_2)_oHet'$, $O(CH_2)_oCN$, $(CH_2)_oNH_2$, $(CH_2)_oNHA$ or $(CH_2)_oNAA'$.

$R^7$ preferably denotes CN; $COOR^9$, such as, for example, COOH or $COOCH_3$; $CONR^9R^{10}$, such as, for example, $CONH_2$; $NR^9R^{10}$, such as, for example, amino, methylamino or dimethylamino; $NHCOR^9$, $NHCOOR^9$ or $OR^9$, such as, for example, hydroxyl or methoxy.

$R^8$ preferably denotes cyclopentyl, cyclohexyl, methyl, ethyl, propyl or butyl.

$R^9$, $R^{10}$ preferably each, independently of one another, denote H or alkyl having 1-5 C atoms, in which 1-5H atoms may be replaced by F and/or Cl.

X preferably denotes alkylene having 1-6 C atoms, in which one, two or three $CH_2$ groups may be replaced by O, NH, and/or 1-5H atoms by F and/or Cl; very particularly preferably alkylene having 1, 2, 3 or 4 C atoms.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-ureidophenyl, o-, m- or p-formylphenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $XR^7$, phenyl, OA, $OXR^7$ and/or $CONR^9R^{10}$.

Ar' denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-ureidophenyl, o-, m- or p-formylphenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar' preferably denotes phenyl which is mono-, di- or trisubstituted by Hal, A, $XR^7$, OA, $OXR^7$ and/or $CONR^9R^{10}$.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-2- or -4-imidazolyl, 2,3-dihydro-1-, -2-, -3-, -4- or -5-pyrazolyl, tetrahydro-1, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8- 3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Irrespective of further substitutions, Het' denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het' can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-2- or -4-imidazolyl, 2,3-dihydro-1-, -2-, -3-, -4- or -5-pyrazolyl, tetrahydro-1, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8- 3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het' preferably denotes a mono- or bicyclic saturated, unsaturated or aromatic heterocycle having 1 to 3 N, O and/or S atoms, which may be unsubstituted or mono-, di- or trisubstituted by A, Hal, OH and/or OA and/or in which a ring nitrogen may be substituted by —$O^-$.

Het' particularly preferably denotes pyridyl, N-oxypyridyl, furyl, thienyl, pyrrolyl, oxazolyl, isoxazolyl, imidazolyl, pyrimidinyl, pyrazolyl, thiazolyl, pyrazinyl, pyridazinyl, pyrrolidinyl, piperidinyl, morpholinyl, piperazinyl, benzodioxanyl, benzodioxolyl, indolyl, quinolinyl, benzimidazolyl, benzothiadiazolyl or indazolyl, each of which is unsubstituted or mono-, di- or trisubstituted by A, Hal, OH and/or OA.

Het" preferably denotes pyridyl, furyl, thienyl, pyrrolyl, oxazolyl, isoxazolyl, imidazolyl or pyrimidinyl.

Het''' preferably denotes pyrrolidinyl, piperidinyl, morpholinyl, tetrahydrofuranyl, tetrahydrothiofuranyl or piperazinyl.

The compounds of the formula I may have one or more chiral centres and therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ir, which conform to the formula I and in which the radicals not designated in greater detail have the meaning indicated for the formula I, but in which in Ia $R^1$ denotes OH or $OCH_3$;
in Ib $R^3$ denotes H;
in Ic $R^2$ denotes $CONA[(CH_2)_oAr]$, $CONA[(CH_2)_oHet']$, $SO_2NA[(CH_2)_oAr']$ or $SO_2NA[(CH_2)_oHet']$,
  where A denotes alkyl having 1, 2, 3 or 4 C atoms;
in Id $R^2$ denotes $CON(CH_3)CH_2Ar$, $CON(CH_3)CH_2Het'$, $SO_2N(CH_3)CH_2Ar'$ or $SO_2N(CH_3)CH_2Het'$;
in Ie $R^4$, $R^5$, $R^6$ each, independently of one another, denote H, Hal, CN, A, $O(CH_2)_oHet'$, $O(CH_2)_oCN$, $(CH_2)_oNH_2$, $(CH_2)_oNHA$ or $(CH_2)_oNAA'$;
in If $R^4$, $R^5$ denote H,
  $R^6$ denotes H, Hal, CN, A, $O(CH_2)_oHet'$, $O(CH_2)_oCN$, $(CH_2)_oNH_2$, $(CH_2)_oNHA$ or $(CH_2)_oNAA'$;
in Ig X denotes alkylene having 1-6 C atoms, in which one, two or three $CH_2$ groups may be replaced by O, NH, and/or 1-5H atoms may be replaced by F and/or Cl;
in Ih X denotes alkylene having 1, 2, 3 or 4 C atoms;
in Ii Ar denotes phenyl which is unsubstituted or mono-, di- or trisubstituted by Hal, A, $XR^7$, phenyl, Het", OXHet'", OA, $OXR^7$ and/or $CONR^9R^{10}$;
in Ij Ar' denotes phenyl which is mono-, di- or trisubstituted by Hal, A, $XR^7$, OA, $OXR^7$ and/or $CONR^9R^{10}$;
in Ik $R^7$ denotes CN, $CONR^9R^{10}$, $NR^9R^{10}$ or $OR^9$;
in Il Het' denotes a mono- or bicyclic saturated, unsaturated or aromatic heterocycle having 1 to 3 N, O and/or S atoms, which may be unsubstituted or mono-, di- or trisubstituted by A, Hal, OH and/or OA and/or in which a ring nitrogen may be substituted by —O⁻;
in Im Het' denotes pyridyl, N-oxypyridyl, furyl, thienyl, pyrrolyl, oxazolyl, isoxazolyl, imidazolyl, pyrimidinyl, pyrazolyl, thiazolyl, pyrazinyl, pyridazinyl, pyrrolidinyl, piperidinyl, morpholinyl, piperazinyl, benzodioxanyl, benzodioxolyl, indolyl, quinolinyl, benzimidazolyl, benzothiadiazolyl or indazolyl, each of which is unsubstituted or mono-, di- or trisubstituted by A, Hal, OH and/or OA;
in In A denotes unbranched or branched alkyl having 1-6 C atoms, in which one, two or three $CH_2$ groups may be replaced by O, S, SO, $SO_2$, NH and/or by —CH=CH— groups and/or in addition 1-5H atoms may be replaced by F, Cl and/or Br,
  Alk or cyclic alkyl having 3-7 C atoms;
in Io $R^9$, $R^{10}$ each, independently of one another, denote H or alkyl having 1-5 C atoms, in which 1-5H atoms may be replaced by F and/or Cl;
in Ip A denotes unbranched or branched alkyl having 1-6 C atoms, in which 1-5H atoms may be replaced by F, Cl and/or Br;
in Iq $R^1$ denotes OH or $OCH_3$,
  $R^2$ denotes $CONA[(CH_2)_oAr]$, $CONA[(CH_2)_oHet']$, $SO_2NA[(CH_2)_oAr']$ or $SO_2NA[(CH_2)_oHet']$,
  where A denotes alkyl having 1, 2, 3 or 4 C atoms,
  $R^3$ denotes H,
  $R^4$, $R^5$, $R^6$ each, independently of one another, denote H, Hal, CN, A, $O(CH_2)_oHet'$, $O(CH_2)_oCN$, $(CH_2)_oNH_2$, $(CH_2)_oNHA$ or $(CH_2)_oNAA'$,
  X denotes alkylene having 1-6 C atoms, in which one, two or three $CH_2$ groups may be replaced by O, NH, and/or 1-5H atoms may be replaced by F, and/or Cl,
  Ar denotes phenyl which is unsubstituted or mono-, di- or trisubstituted by Hal, A, $XR^7$, phenyl, Het", OXHet'", OA, $OXR^7$ and/or $CONR^9R^{10}$,
  Ar' denotes phenyl which is mono-, di- or trisubstituted by Hal, A, $XR^7$, OA, $OXR^7$ and/or $CONR^9R^{10}$,
  $R^7$ denotes CN, $CONR^9R^{10}$, $NR^9R^{10}$ or $OR^9$,
  Het' denotes a mono- or bicyclic saturated, unsaturated or aromatic heterocycle having 1 to 3 N, O and/or S atoms, which may be unsubstituted or mono-, di- or trisubstituted by A, Hal, OH and/or OA and/or in which a ring nitrogen may be substituted by —O⁻,
  A denotes unbranched or branched alkyl having 1-6 C atoms, in which one, two or three $CH_2$ groups may be replaced by O, S, SO, $SO_2$, NH and/or by —CH=CH— groups and/or in addition 1-5H atoms may be replaced by F, Cl and/or Br,
  Alk or cyclic alkyl having 3-7 C atoms,
  $R^9$, $R^{10}$ each, independently of one another, denote H or alkyl having 1-5 C atoms, in which 1-5H atoms may be replaced by F and/or Cl;
in Ir $R^1$ denotes OH or $OCH_3$,
  $R^2$ denotes $CON(CH_3)CH_2Ar$, $CON(CH_3)CH_2Het'$, $SO_2N(CH_3)CH_2Ar'$ or $SO_2N(CH_3)CH_2Het'$,
  $R^3$ denotes H,
  $R^4$, $R^5$ denote H,
  $R^6$ denotes H, Hal, CN, A, $O(CH_2)_oHet'$, $O(CH_2)_oCN$, $(CH_2)_oNH_2$, $(CH_2)_oNHA$ or $(CH_2)_oNAA'$,
  X denotes alkylene having 1, 2, 3 or 4 C atoms,
  Ar denotes phenyl which is unsubstituted or mono-, di- or trisubstituted by Hal, A, $XR^7$, phenyl, Het", OXHet'", OA, $OXR^7$ and/or $CONR^9R^{10}$,
  Ar' denotes phenyl which is mono-, di- or trisubstituted by Hal, A, $XR^7$, OA, $OXR^7$ and/or $CONR^9R^{10}$,
  $R^7$ denotes CN, $CONR^9R^{10}$, $NR^9R^{10}$ or $OR^9$,
  Het' denotes pyridyl, N-oxypyridyl, furyl, thienyl, pyrrolyl, oxazolyl, isoxazolyl, imidazolyl, pyrimidinyl, pyrazolyl, thiazolyl, pyrazinyl, pyridazinyl, pyrrolidinyl, piperidinyl, morpholinyl, piperazinyl, benzodioxanyl, benzodioxolyl, indolyl, quinolinyl, benzimidazolyl, benzothiadiazolyl or indazolyl, each of which is unsubstituted or mono-, di- or trisubstituted by A, Hal, OH and/or OA,
  A denotes unbranched or branched alkyl having 1-6 C atoms, in which 1-5H atoms may be replaced by F, Cl and/or Br,
  or cyclic alkyl having 3-7 C atoms,
  $R^9$, $R^{10}$ each, independently of one another, denote H or alkyl having 1-5 C atoms, in which 1-5H atoms may be replaced by F and/or Cl;

and pharmaceutically usable derivatives, solvates, salts, tautomers and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

Compounds of the formula I can preferably be obtained by reacting a compound of the formula II with a compound of the formula III.

The compounds of the formula II and III are generally known. If they are not know, they can be prepared by methods known per se.

The reaction is carried out by methods which are known to the person skilled in the art.

The reaction is carried out in a suitable inert solvent.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The solvent is particularly preferably, for example, tetrahydrofuran.

Depending on the conditions used, the reaction time is between a few minutes and 14 days, the reaction temperature is between about −30° and 140°, normally between −10° and 130°, in particular between about 30° and about 125°.

Compounds of the formula I can furthermore be obtained by reacting compounds of the formula IV with compounds of the formula V to give thiosemicarbazide derivatives and subsequently cyclising the latter.

The starting compounds of the formulae IV and V are generally known. If they are not known, they can be prepared by methods known per se.

The reaction of the compounds of the formula IV with compounds of the formula V is carried out under the same conditions, relating to the reaction time, temperature and solvents, as has been described for the reaction of the compounds of the formula II with compounds of the formula III.

The cyclisation of the thiosemicarbazide derivatives is carried out under basic conditions. Suitable bases are preferably alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine or diethanolamine.

The protecting groups are removed by methods which are known to the person skilled in the art.

The cleavage of an ether, for example a methyl ether, is carried out in a suitable solvent, as indicated above, preferably by addition of boron tribromide.

The reaction is particularly preferably carried out in dichloromethane at a reaction temperature between about −30° and 50°, normally between −20° and 20°, in particular between about −15° and about 0°.

The compounds of the formula I can furthermore be obtained by liberating them from functional derivatives thereof by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' denotes an amino-protecting group, for example BOC or CBZ) instead of an $NH_2$ group.

Preference is furthermore given to starting materials which carry a hydroxyl-protecting group instead of the H atom of an hydroxyl group, for example those which conform to the formula I, but contain an R"O-phenyl group (in which R" denotes an hydroxyl-protecting group) instead of an hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf or Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, p-nitrobenzoyl, p-toluenesulfonyl, tert-butyl and acetyl, where benzyl and tert-butyl are particularly preferred. COOH groups are preferably protected in the form of their tert-butyl esters.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Protecting groups which can be removed hydrogenolytically (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

It is furthermore possible to convert a compound of the formula I into another compound of the formula I by converting one or more radical(s) $R^1$, $R^2$, $R^3$, $R^4$, $R^5$ and/or $R^6$ into one or more other radicals $R^1$, $R^2$, $R^3$, $R^4$, $R^5$ and/or $R^6$, for example by reducing nitro groups to amino groups, for example by hydrogenation on Raney nickel or Pd/carbon in an inert solvent, such as methanol or ethanol, and/or
converting an ester group into a carboxyl group and/or converting an amino group into an alkylated amine by reductive amination and/or
esterifying carboxyl groups by reaction with alcohols and/or converting acid chlorides into an acid amide by reaction with an amine.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.1 mg to 3 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound according to the invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

Further medicament active ingredients are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discormolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 5-fluorodeoxyuridine monophosphate, cytarabine, 5-azacytidine, thioguanine, azathioprine, adenosine, pentostatin, erythrohydroxynonyladenine, cladribine, 6-mercaptopurine, gemcitabine, cytosinarabinoside, podophyllotoxin or podophyllotoxin derivatives, such as, for example, etoposide, etoposide phosphate or teniposide, melphalan, vinblastine, vinorelbine, vincristine, leurosidine, vindesine, leurosine, docetaxel and paclitaxel. Other preferred antineoplastic agents are selected from the group discormolide, epothilone D, estramustine, carboplatin, cisplatin, oxaliplatin, cyclophosphamide, bleomycin, gemcitabine, ifosamide, melphalan, hexamethylmelamine, thiotepa, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

Further medicament active ingredients are preferably antibiotics. Preferred antibiotics are selected from the group dactinomycin, daunorubicin, idarubicin, epirubicin, mitoxantrone, bleomycin, plicamycin, mitomycin.

Further medicament active ingredients are preferably enzyme inhibitors. Preferred enzyme inhibitors are selected from the group of the histone deacetylation inhibitors (for example suberoylanilide hydroxamic acid [SAHA]) and the tyrosine kinase inhibitors (for example ZD 1839 [Iressa]).

Further medicament active ingredients are preferably nuclear export inhibitors. Nuclear export inhibitors prevent the output of biopolymers (for example RNA) from the cell nucleus. Preferred nuclear export inhibitors are selected from the group callystatin, leptomycin B, ratjadone.

Further medicament active ingredients are preferably nuclear export inhibitors. Nuclear export inhibitors prevent the output of biopolymers (for example RNA) from the cell nucleus. Preferred nuclear export inhibitors are selected from the group callystatin, leptomycin B, ratjadone.

Further medicament active ingredients are preferably immunosuppressants. Preferred immunosuppressants are selected from the group rapamycin, CCI-779 (Wyeth), RAD001 (Novartis), AP23573 (Ariad Pharmaceuticals).

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios,
and an effective amount of a further medicament active ingredient in dissolved or lyophilised form.

Use

The present compounds are suitable as pharmaceutical active ingredients for mammals, in particular for humans, in the treatment of diseases in which HSP90 plays a role.

The invention thus relates to the use of compounds according to the invention, and pharmaceutically usable derivatives, solvates and stereoisomers thereof, including mixtures thereof in all ratios, for the preparation of a medicament for the treatment of diseases in which the inhibition, regulation and/or modulation of HSP90 plays a role.

Preference is given here to SGK.

Preference is given to the use of compounds according to the invention and pharmaceutically usable derivatives, solvates and stereoisomers thereof, including mixtures thereof in all ratios, for the preparation of a medicament for the treatment of tumour diseases, for example fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous cell carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy-chain disease;

viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type I (HIV-I) and human immunodeficiency virus type II (HIV-II);

for immune suppression in transplants; inflammation-induced diseases, such as rheumatoid arthritis, asthma, multiple sclerosis, type 1 diabetes, lupus erythematosus, psoriasis and inflammatory bowel disease; cystic fibrosis; diseases associated with angiogenesis, such as, for example, diabetic retinopathy, haemangioma, endometriosis, tumour angiogenesis; infectious diseases; autoimmune diseases; ischaemia; promotion of nerve regeneration; fibrogenetic diseases, such as, for example, dermatosclerosis, polymyositis, systemic lupus, cirrhosis of the liver, keloid formation, interstitial nephritis and pulmonary fibrosis;

The compounds according to the invention can inhibit, in particular, the growth of cancer, tumour cells and tumour metastases and are therefore suitable for tumour therapy.

The present invention furthermore encompasses the use of the compounds according to the invention and/or physiologically acceptable salts and solvates thereof for the preparation of a medicament for the protection of normal cells against toxicity caused by chemotherapy, and for the treatment of diseases in which incorrect protein folding or aggregation is a principal causal factor, such as, for example, scrapie, Creutzfeldt-Jakob disease, Huntington's or Alzheimer's.

The invention also relates to the use of the compounds according to the invention and/or physiologically acceptable salts and solvates thereof for the preparation of a medicament for the treatment of diseases of the central nervous system, of cardiovascular diseases and cachexia.

In a further embodiment, the invention also relates to the use of the compounds according to the invention and/or physiologically acceptable salts and solvates thereof for the preparation of a medicament for HSP90 modulation, where the modulated biological HSP90 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

In a further embodiment, the invention also relates to the use of the compounds according to the invention and/or physiologically acceptable salts and solvates thereof for the preparation of a medicament for the treatment of ischaemia as a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Test Method for the Measurement of HSP90 Inhibitors

The binding of geldanamycin or 17-allylamino-17-demethoxygeldanamycin (17AAG) to HSP90 and competitive inhibition thereof can be utilised in order to determine the inhibitory activity of the compounds according to the invention (Carreras et al. 2003, Chiosis et al. 2002).

In the specific case, a radioligand filter binding test is used. The radioligand used here is tritium-labelled 17-allylaminogeldanamycin, [3H]17AAG. This filter binding test allows a targeted search for inhibitors which interfere with the ATP binding site.

Material

Recombinant human HSP90α (*E. coli* expressed, 95% purity);

[3H]17AAG (17-allylaminogeldanamycin, [allylamino-2,3-$^3$H. Specific activity: $1.11 \times 10^{12}$ Bq/mmol (Moravek, MT-1717);

HEPES filter buffer (50 mM HEPES, pH 7.0, 5 mM MgCl2, BSA 0.01%)

Multiscreen F B (1 μm) filter plate (Millipore, MAFBNOB 50).

Method

The 96-well microtitre filter plates are firstly irrigated and coated with 0.1% of polyethylenimine.

The test is carried out under the following conditions:
Reaction temperature 22° C.
Reaction time: 30 min., shaking at 800 rpm
Test volume: 50 μl
Final Concentrations:
50 mM HEPES HCl, pH 7.0, 5 mM MgCl2, 0.01% (w/v) BSA
HSP90: 1.5 μg/assay

[3H]17AAG: 0.08 µM.

At the end of the reaction, the supernatant in the filter plate is removed by suction with the aid of a vacuum manifold (Multiscreen Separation System, Millipore), and the filter is washed twice.

The filter plates are then measured in a beta counter (Microbeta, Wallac) with scintillator (Microscint 20, Packard).

"% of control" is determined from the "counts per minutes" values and the $IC_{50}$ value of a compound is calculated therefrom.

Test Results

TABLE I

HSP90 inhibition by compounds according to the invention

| Compound of the formula I | $IC_{50}$* |
|---|---|
| "A1" | A |
| "A6" | A |
| "A6a" | A |
| "A6b" | A |
| "A9" | A |
| "A12" | A |
| "A15" | A |
| "A18a" | A |
| "A24" | A |
| "A27" | A |
| "A51" | A |
| "A57" | A |
| "A57a" | A |
| "A57b" | A |
| "A58" | A |
| "A58a" | A |
| "A58b" | A |
| "A58c" | A |
| "A59a" | A |
| "A59b" | A |
| "A62a" | A |
| "A62b" | A |
| "A62c" | A |
| "A116a" | A |
| "A116b" | A |
| "A116c" | B |
| "A116d" | A |

*$IC_{50}$: 10 nM-1 µM = A
1 µM-10 µM = B
>10 µM = C

Above and below, all temperatures are indicated in °C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

LC-MS Conditions

HP 1100 series Hewlett Packard System having the following features: ion source: electrospray (positive mode); scan: 100-1000 m/e; fragmentation voltage: 60 V; gas temperature: 300° C., DAD: 220 nm.

Flow rate: 2.4 ml/min. The splitter used reduced the flow rate for the MS to 0.75 ml/min. after the DAD.

Column: Chromolith SpeedROD RP-18e 50-4.6
Solvent: LiChrosolv quality from Merck KGaA
Solvent A: H2O (0.01% of TFA)
Solvent B: ACN (0.008% of TFA)
Gradient:
20% of B→100% of B: 0 min to 2.8 min
100% of B: 2.8 min to 3.3 min
100% of B→20% of B: 3.3 min to 4 min The retention times $R_f$ or $R_t$ [min] and M+H$^+$ data MW indicated in the following examples are the measurement results of the LC-MS measurements.

EXAMPLE 1

Preparation of 5-[2,4-dihydroxy-5-(N-benzyl-N-methylaminocarbonyl)phenyl]-4-(2-methylphenyl)-3-hydroxy-4H-1,2,4-triazole ("A1")

1.1 80 g of 5-bromo-2,4-dihydroxybenzoic acid are initially introduced in 1 l of methanol, 8 ml of sulfuric acid are added, and the mixture is boiled for 16 hours. The solvent is removed, the residue is taken up in MTB ether, and the solution is subjected to conventional work-up, giving 80 g of methyl 5-bromo-2,4-dihydroxybenzoate.

1.2 92.6 g of potassium carbonate are added to a solution of 80 g of methyl 5-bromo-2,4-dihydroxybenzoate in 1 l of acetonitrile, and 77 ml of benzyl bromide are added dropwise. The mixture is heated for 3 hours and cooled, the solvent is removed, and the residue is subjected to conventional work-up, giving 150 g of methyl 5-bromo-2,4-dibenzyloxybenzoate (crude product).

1.3 800 ml of 2N NaOH are added to a solution of 150 g of methyl 5-bromo-2,4-dibenzyloxybenzoate in 500 ml of THF, and the mixture is stirred at 50° for 2 hours and subsequently stirred at room temperature for 16 hours. The red alkaline phase is separated off and cooled, and conc. hydrochloric acid is added dropwise to pH 2-3. The precipitated product is separated off and dried, giving 132 g of 5-bromo-2,4-dibenzyloxybenzoic acid.

1.4 9 g of 5-bromo-2,4-dibenzyloxybenzoic acid, 40 ml of thionyl chloride and 1 drop of DMF are stirred at room temperature for 4 hours. The thionyl chloride is removed, and the residue is treated twice with dichloromethane, giving 9.4 g of 5-bromo-2,4-dibenzyloxybenzoyl chloride, which is processed further directly.

1.5 A solution of 4.5 g of 5-bromo-2,4-dibenzyloxybenzoyl chloride in 6 ml of dichloromethane is added dropwise with ice-cooling to a solution of 1.126 ml of o-toluidine and 1.211 ml of pyridine in 40 ml of dichloromethane. The mixture is stirred at room temperature for a further 16 hours and subjected to conventional work-up, giving 3 g of 5-bromo-2,4-dibenzyloxy-N-o-tolylbenzamide.

1.6 1.5 g of PCl$_5$ are added under an argon atmosphere to a solution of 3 g of 5-bromo-2,4-dibenzyloxy-N-o-tolylbenzamidine in 30 ml of toluene, and the mixture is refluxed for 3 hours. The solvent is distilled off, the residue is dissolved in 50 ml of THF, and 70 ml of 1 M hydrazine solution in THF are added dropwise. The mixture is stirred at room temperature for a further 16 hours, poured into water and extracted with ethyl acetate. Conventional work-up gives N-(2-methylphenyl)-3-bromo-4,6-dibenzyloxybenzamide hydrazone.

1.7 A solution of 30.98 g of N-(2-methylphenyl)-3-bromo-4,6-dibenzyloxybenzamide hydrazone in 200 ml of THF is slowly added at 45-50° to a solution of 11.67 g of 1,1'-carbonyldiimidazole in 1 l of THF. The mixture is stirred at room temperature for 30 minutes, the solvent is removed, and the residue is subjected to conventional work-up, giving 26 g of 5-(2,4-dibenzyloxy-5-bromophenyl)-4-(2-methylphenyl)-3-hydroxy-4H-1,2,4-triazole, $R_f$ 2.25.

1.8 Reaction in an autoclave at 100°/4-8 bar/5 hours:
7.3 g of 5-(2,4-dibenzyloxy-5-bromophenyl)-4-(2-methylphenyl)-3-hydroxy-4H-1,2,4-triazole, 150 ml of methanol, 0.3 l of carbon monoxide, 150 mg of [1,1'-bis(diphenylphosphino)ferrocene]dichloropalladium(II), 2 g of triethylamine and 10 ml of toluene.

Work-up gives a mixture of 3 compounds, two having the molecular weight of the monobenzyl ether and dibenzyl ether

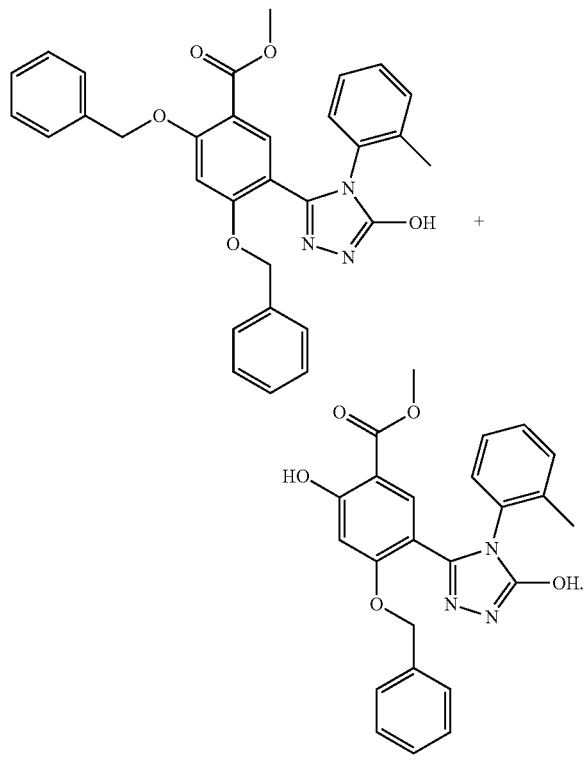

The product mixture is employed directly in the ester cleavage.

1.9 Reaction of the ester obtained in 1.8 with 2 N NaOH in methanol/THF under standard conditions followed by conventional work-up gives a mixture of

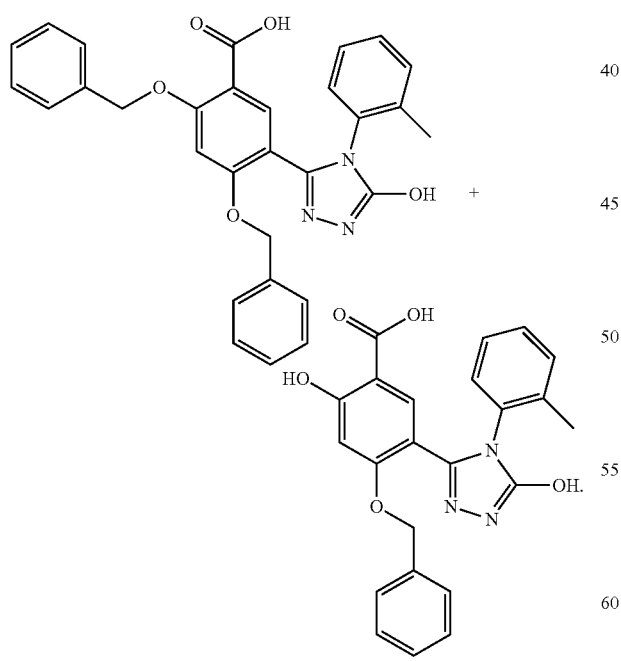

1.10 A solution of 3.045 g of the carboxylic acids obtained in 1.9 in 100 ml of THF is cooled, and 1.319 ml of 4-methylmorpholine and 2.119 g of O-(1H-benzotriazol-1-yl)-N,N,N',N'-tetramethyluronium tetrafluoroborate (TBTU) are added. The mixture is stirred for 1 hour, 0.878 ml of N-benzylmethylamine is added, and the mixture is stirred at room temperature for a further 16 hours. The THF is separated off, and the mixture is subjected to conventional work-up, giving a mixture of

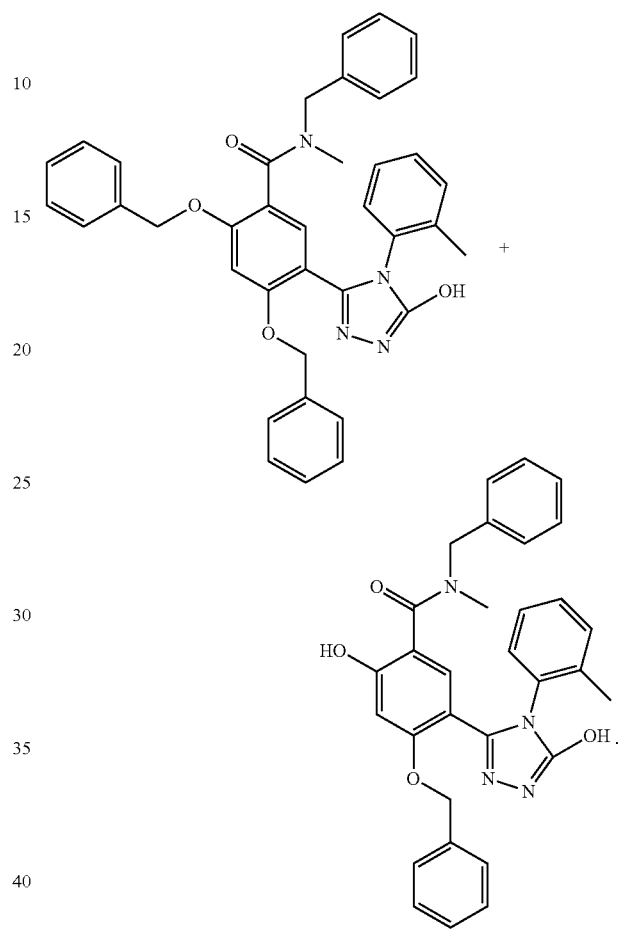

1.11 3.6 g of the amides obtained in 1.10 in 36 ml of THF are hydrogenated under standard conditions in the presence of 1.8 g of Pd/C (5%). The catalyst is subsequently separated off, and the mixture is subjected to conventional work-up, giving 915 mg of 5-[2,4-dihydroxy-5-(N-benzyl-N-methylaminocarbonyl)phenyl]-4-(2-methylphenyl)-3-hydroxy-4H-1,2,4-triazole, MW 431.5

"A1"

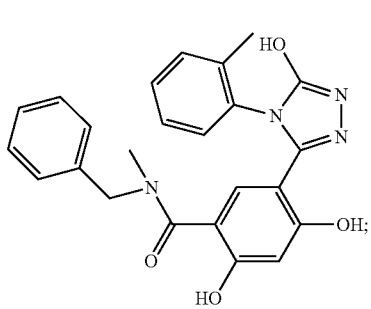

$^1$H NMR (500 MHz, DMSO-d$_6$) δ [ppm] 11.91 (s, 1H), 10.18 (s, 1H), 9.96 (s, 1H), 7.40-7.21 (m, 8H), 7.02 (b, 2H), 6.30 (s, 1H), 4.51 (s, 2H), 2.51 (s, 3H), 2.14 (s, 3H).

The following compounds are obtained analogously:

| Compound No. | Structure/Name | MW |
|---|---|---|
| "A2" | [structure: benzamide with HO, HO substituents, N-methyl-N-benzyl amide, linked to triazole with OH, phenyl-O-CH2CH2-piperazine-NH] | 545.6 |
| "A3" | 5-[2,4-Dihydroxy-5-(N-benzyl-N-methylaminocarbonyl)phenyl]-4-phenyl-3-hydroxy-4H-1,2,4-triazole [structure shown] | 417.4 |
| "A4" | 5-[2,4-Dihydroxy-5-(N-benzyl-N-methylaminocarbonyl)phenyl]-4-(2-chlorophenyl)-3-hydroxy-4H-1,2,4-triazole [structure shown] | 451.9 |
| "A5" | 5-[2,4-Dihydroxy-5-(N-benzyl-N-methylaminocarbonyl)phenyl]-4-(2-fluorophenyl)-3-hydroxy-4H-1,2,4-triazole | 435.4 |
| "A6" | 5-{2,4-Dihydroxy-5-[N-(2-methoxybenzyl)-N-methyl-aminocarbonyl]phenyl}-4-(2-methylphenyl)-3-hydroxy-4H-1,2,4-triazole | 461.5 |

| Compound No. | Structure/Name | MW |
|---|---|---|

[Structure: benzamide with 2,4-dihydroxy substitution, bearing N-methyl-N-(2-methoxybenzyl) amide; with 4-(2-methylphenyl)-3-hydroxy-4H-1,2,4-triazol-5-yl substituent]

¹H NMR (500 MHz, DMSO-d₆) δ [ppm] 11.89 (s, 1 H), 10.16 (s, 1 H), 9.92 (s, 1 H), 7.31-6.92 (m, 9 H), 6.27 (s, 1 H), 4.12 (s, 2 H), 3.78 (s, 3 H), 2.71 (s, 3 H), 2.11 (s, 3 H)

| | | |
|---|---|---|
| "A6a" | 5-{2,4-Dihydroxy-5-[N-(3-methoxybenzyl)-N-methyl-aminocarbonyl]phenyl}-4-(2-methylphenyl)-3-hydroxy-4H-1,2,4-triazole | 461.5 |

¹H NMR (500 MHz, DMSO-d₆) δ [ppm] 11.89 (s, 1 H), 10.18 (s, 1 H), 9.94 (s, 1 H), 7.23 (m, 3 H), 7.06-6.82 (m, 6 H), 6.29 (s, 1 H), 4.19 (s, 2 H), 3.74 (s, 3 H), 2.68 (s, 3 H), 2.12 (s, 3 H)

| | | |
|---|---|---|
| "A6b" | 5-{2,4-Dihydroxy-5-[N-(4-methoxybenzyl)-N-methyl-aminocarbonyl]phenyl}-4-(2-methylphenyl)-3-hydroxy-4H-1,2,4-triazole | 461.5 |
| "A7" | 5-{2,4-Dihydroxy-5-[N-(2-methoxybenzyl)-N-methyl-aminocarbonyl]phenyl}-4-(2-chlorophenyl)-3-hydroxy-4H-1,2,4-triazole | 481.9 |
| "A8" | 5-{2,4-Dihydroxy-5-[N-(2-methoxybenzyl)-N-methyl-aminocarbonyl]phenyl}-4-(2-fluorophenyl)-3-hydroxy-4H-1,2,4-triazole | 465.5 |
| "A9" | 5-{2,4-Dihydroxy-5-[N-(2-fluorobenzyl)-N-methyl-aminocarbonyl]phenyl}-4-(2-methylphenyl)-3-hydroxy-4H-1,2,4-triazole | 449.5 |

¹H NMR (500 MHz, DMSO-d₆) δ [ppm] 11.89 (s, 1 H), 10.18 (s, 1 H), 9.95 (s, 1 H), 7.34 (dd, 1 H), 7.30-7.05 (m, 7 H), 6.98 (s, 1 H), 6.28 (s, 1 H), 4.54 (s, 2 H), 2.71 (s, 3 H), 2.13 (s, 3 H)

| | | |
|---|---|---|
| "A10" | 5-{2,4-Dihydroxy-5-[N-(2-fluorobenzyl)-N-methyl-aminocarbonyl]phenyl}-4-(2-chlorophenyl)-3-hydroxy-4H-1,2,4-triazole | 469.9 |
| "A11" | 5-{2,4-Dihydroxy-5-[N-(2-fluorobenzyl)-N-methyl-aminocarbonyl]phenyl}-4-(2-fluorophenyl)-3-hydroxy-4H-1,2,4-triazole | 453.4 |
| "A12" | 5-{2,4-Dihydroxy-5-[N-(4-fluorobenzyl)-N-methyl-aminocarbonyl]phenyl}-4-(2-methylphenyl)-3-hydroxy-4H-1,2,4-triazole | 449.5 |

¹H NMR (500 MHz, DMSO-d₆) δ [ppm] 11.90 (s, 1 H), 10.16 (s, 1 H), 9.95 (s, 1 H), 7.40-7.21 (m, 7 H), 7.02 (b, 2 H), 6.28 (s, 1 H), 4.47 (s, 2 H), 2.47 (s, 3 H), 2.13 (s, 3 H)

| | | |
|---|---|---|
| "A13" | 5-{2,4-Dihydroxy-5-[N-(4-fluorobenzyl)-N-methyl-aminocarbonyl]phenyl}-4-(2-chlorophenyl)-3-hydroxy-4H-1,2,4-triazole | 469.9 |
| "A14" | 5-{2,4-Dihydroxy-5-[N-(4-fluorobenzyl)-N-methyl-aminocarbonyl]phenyl}-4-(2-fluorophenyl)-3-hydroxy-4H-1,2,4-triazole | 453.4 |
| "A15" | 5-{2,4-Dihydroxy-5-[N-(3-fluorobenzyl)-N-methyl-aminocarbonyl]phenyl}-4-(2-methylphenyl)-3-hydroxy-4H-1,2,4-triazole | 449.5 |

¹H NMR (500 MHz, DMSO-d₆) δ [ppm] 11.89 (s, 1 H), 10.20 (s, 1 H), 9.95 (s, 1 H), 7.40 (dd, 1 H), 7.25-7.00 (m, 8 H), 6.29 (s, 1 H), 4.54 (s, 2 H), 2.69 (s, 3 H), 2.13 (s, 3 H)

| | | |
|---|---|---|
| "A16" | 5-{2,4-Dihydroxy-5-[N-(3-fluorobenzyl)-N-methyl-aminocarbonyl]phenyl}-4-(2-chlorophenyl)-3-hydroxy-4H-1,2,4-triazole | 469.9 |
| "A17" | 5-{2,4-Dihydroxy-5-[N-(3-fluorobenzyl)-N-methyl-aminocarbonyl]phenyl}-4-(2-fluorophenyl)-3-hydroxy-4H-1,2,4-triazole | 453.4 |
| "A18" | 5-{2,4-Dihydroxy-5-[N-(3-methylbenzyl)-N-methyl-aminocarbonyl]phenyl}-4-(2-methylphenyl)-3-hydroxy-4H-1,2,4-triazole | 445.5 |

¹H NMR (500 MHz, DMSO-d₆) δ [ppm] 11.87 (s, 1 H), 10.17 (s, 1 H), 9.96 (s, 1 H), 7.33-6.90 (m, 9 H), 6.28 (s, 1 H), 4.45 (s, 2 H), 2.67 (s, 3 H), 2.31 (s, 3 H), 2.13 (s, 3 H)

-continued

| Compound No. | Structure/Name | MW |
|---|---|---|
| "A18a" | 5-{2,4-Dihydroxy-5-[N-(2-methylbenzyl)-N-methyl-aminocarbonyl]phenyl}-4-(2-methylphenyl)-3-hydroxy-4H-1,2,4-triazole | 445.5 |
| "A19" | 5-{2,4-Dihydroxy-5-[N-(3-methylbenzyl)-N-methyl-aminocarbonyl]phenyl}-4-(2-chlorophenyl)-3-hydroxy-4H-1,2,4-triazole | 465.9 |
| "A20" | 5-{2,4-Dihydroxy-5-[N-(3-methylbenzyl)-N-methyl-aminocarbonyl]phenyl}-4-(2-fluorophenyl)-3-hydroxy-4H-1,2,4-triazole | 449.5 |
| "A21" | 5-{2,4-Dihydroxy-5-[N-(4-methylbenzyl)-N-methyl-aminocarbonyl]phenyl}-4-(2-methylphenyl)-3-hydroxy-4H-1,2,4-triazole | 445.5 |
| "A22" | 5-{2,4-Dihydroxy-5-[N-(4-methylbenzyl)-N-methyl-aminocarbonyl]phenyl}-4-(2-chlorophenyl)-3-hydroxy-4H-1,2,4-triazole | 465.9 |
| "A23" | 5-{2,4-Dihydroxy-5-[N-(4-methylbenzyl)-N-methyl-aminocarbonyl]phenyl}-4-(2-fluorophenyl)-3-hydroxy-4H-1,2,4-triazole | 449.5 |
| "A24" | 5-{2,4-Dihydroxy-5-[N-(3-chlorobenzyl)-N-methyl-aminocarbonyl]phenyl}-4-(2-methylphenyl)-3-hydroxy-4H-1,2,4-triazole | 465.9 |

$^1$H NMR (500 MHz, DMSO-$d_6$) δ [ppm] 11.92 (s, 1 H), 10.20 (s, 1 H), 9.95 (s, 1 H), 7.41-7.06 (m, 8 H), 7.00 (s, 1 H), 6.30 (s, 1 H), 4.54 (s, 2 H), 2.69 (s, 3 H), 2.13 (s, 3 H)

| | | |
|---|---|---|
| "A25" | 5-{2,4-Dihydroxy-5-[N-(3-chlorobenzyl)-N-methyl-aminocarbonyl]phenyl}-4-(2-chlorophenyl)-3-hydroxy-4H-1,2,4-triazole | 486.3 |
| "A26" | 5-{2,4-Dihydroxy-5-[N-(3-chlorobenzyl)-N-methyl-aminocarbonyl]phenyl}-4-(2-fluorophenyl)-3-hydroxy-4H-1,2,4-triazole | 469.9 |
| "A27" | 5-{2,4-Dihydroxy-5-[N-(2-chlorobenzyl)-N-methyl-aminocarbonyl]phenyl}-4-(2-methylphenyl)-3-hydroxy-4H-1,2,4-triazole | 465.9 |

$^1$H NMR (500 MHz, DMSO-$d_6$) δ [ppm] 11.89 (s, 1 H), 10.22 (s, 1 H), 9.96 (s, 1 H), 7.43-7.07 (m, 8 H), 7.00 (s, 1 H), 6.29 (s, 1 H), 4.65 (s, 2 H), 2.73 (s, 3 H), 2.13 (s, 3 H)

| | | |
|---|---|---|
| "A28" | 5-{2,4-Dihydroxy-5-[N-(2-chlorobenzyl)-N-methyl-aminocarbonyl]phenyl}-4-(2-chlorophenyl)-3-hydroxy-4H-1,2,4-triazole | 486.3 |
| "A29" | 5-{2,4-Dihydroxy-5-[N-(2-chlorobenzyl)-N-methyl-aminocarbonyl]phenyl}-4-(2-fluorophenyl)-3-hydroxy-4H-1,2,4-triazole | 469.9 |
| "A30" | 5-{2,4-Dihydroxy-5-[N-(pyridin-2-ylmethyl)-N-methyl-aminocarbonyl]phenyl}-4-(2-methylphenyl)-3-hydroxy-4H-1,2,4-triazole | 432.5 |

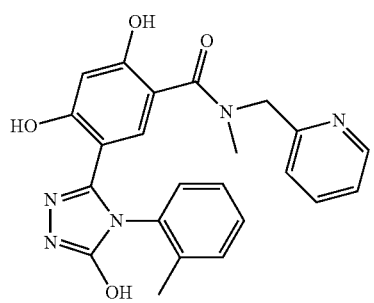

| | | |
|---|---|---|
| "A31" | 5-{2,4-Dihydroxy-5-[N-(pyridin-2-ylmethyl)-N-methyl-aminocarbonyl]phenyl}-4-(2-chlorophenyl)-3-hydroxy-4H-1,2,4-triazole | 452.9 |
| "A32" | 5-{2,4-Dihydroxy-5-[N-(pyridin-2-ylmethyl)-N-methyl-aminocarbonyl]phenyl}-4-(2-fluorophenyl)-3-hydroxy-4H-1,2,4-triazole | 436.4 |
| "A33" | 5-{2,4-Dihydroxy-5-[N-(pyridin-3-ylmethyl)-N-methyl-aminocarbonyl]phenyl}-4-(2-methylphenyl)-3-hydroxy-4H-1,2,4-triazole | 432.5 |
| "A34" | 5-{2,4-Dihydroxy-5-[N-(pyridin-3-ylmethyl)-N-methyl-aminocarbonyl]phenyl}-4-(2-chlorophenyl)-3-hydroxy-4H-1,2,4-triazole | 451.9 |
| "A35" | 5-{2,4-Dihydroxy-5-[N-(pyridin-3-ylmethyl)-N-methyl-aminocarbonyl]phenyl}-4-(2-fluorophenyl)-3-hydroxy-4H-1,2,4-triazole | 436.4 |

-continued

| Compound No. | Structure/Name | MW |
|---|---|---|
| "A36" | 5-{2,4-Dihydroxy-5-[N-(pyridin-4-ylmethyl)-N-methyl-aminocarbonyl]phenyl}-4-(2-methylphenyl)-3-hydroxy-4H-1,2,4-triazole | 432.5 |
| "A37" | 5-{2,4-Dihydroxy-5-[N-(pyridin-4-ylmethyl)-N-methyl-aminocarbonyl]phenyl}-4-(2-chlorophenyl)-3-hydroxy-4H-1,2,4-triazole | 452.9 |
| "A38" | 5-{2,4-Dihydroxy-5-[N-(pyridin-4-ylmethyl)-N-methyl-aminocarbonyl]phenyl}-4-(2-fluorophenyl)-3-hydroxy-4H-1,2,4-triazole | 436.4 |
| "A39" | 5-{2,4-Dihydroxy-5-[N-(1-oxypyridin-2-ylmethyl)-N-methylaminocarbonyl]phenyl}-4-(2-methylphenyl)-3-hydroxy-4H-1,2,4-triazole | 448.5 |
| "A40" | 5-{2,4-Dihydroxy-5-[N-(1-oxypyridin-2-ylmethyl)-N-methylaminocarbonyl]phenyl}-4-(2-chlorophenyl)-3-hydroxy-4H-1,2,4-triazole | 468.9 |
| "A41" | 5-{2,4-Dihydroxy-5-[N-(1-oxypyridin-2-ylmethyl)-N-methylaminocarbonyl]phenyl}-4-(2-fluorophenyl)-3-hydroxy-4H-1,2,4-triazole | 452.4 |
| "A42" | 5-{2,4-Dihydroxy-5-[N-(1-oxypyridin-3-ylmethyl)-N-methylaminocarbonyl]phenyl}-4-(2-methylphenyl)-3-hydroxy-4H-1,2,4-triazole | 448.5 |
| "A43" | 5-{2,4-Dihydroxy-5-[N-(1-oxypyridin-3-ylmethyl)-N-methylaminocarbonyl]phenyl}-4-(2-chlorophenyl)-3-hydroxy-4H-1,2,4-triazole | 468.9 |
| "A44" | 5-{2,4-Dihydroxy-5-[N-(1-oxypyridin-3-ylmethyl)-N-methylaminocarbonyl]phenyl}-4-(2-fluorophenyl)-3-hydroxy-4H-1,2,4-triazole | 452.4 |
| "A45" | 5-{2,4-Dihydroxy-5-[N-(1-oxypyridin-4-ylmethyl)-N-methylaminocarbonyl]phenyl}-4-(2-methylphenyl)-3-hydroxy-4H-1,2,4-triazole | 448.5 |
| "A46" | 5-{2,4-Dihydroxy-5-[N-(1-oxypyridin-4-ylmethyl)-N-methylaminocarbonyl]phenyl}-4-(2-chlorophenyl)-3-hydroxy-4H-1,2,4-triazole | 468.9 |
| "A47" | 5-{2,4-Dihydroxy-5-[N-(1-oxypyridin-4-ylmethyl)-N-methylaminocarbonyl]phenyl}-4-(2-fluorophenyl)-3-hydroxy-4H-1,2,4-triazole | 452.4 |
| "A48" | 5-{2,4-Dihydroxy-5-[N-(2-chloro-6-fluorobenzyl)-N-methylaminocarbonyl]phenyl}-4-(2-methylphenyl)-3-hydroxy-4H-1,2,4-triazole | 483.9 |
| "A49" | 5-{2,4-Dihydroxy-5-[N-(2-chloro-6-fluorobenzyl)-N-methylaminocarbonyl]phenyl}-4-(2-chlorophenyl)-3-hydroxy-4H-1,2,4-triazole | 504.3 |
| "A50" | 5-{2,4-Dihydroxy-5-[N-(2-chloro-6-fluorobenzyl)-N-methylaminocarbonyl]phenyl}-4-(2-fluorophenyl)-3-hydroxy-4H-1,2,4-triazole | 487.9 |
| "A51" | 5-{2,4-Dihydroxy-5-[N-(3-chloro-6-methoxybenzyl)-N-methylaminocarbonyl]phenyl}-4-(2-methylphenyl)-3-hydroxy-4H-1,2,4-triazole | 495.9 |
| | $^1$H NMR (500 MHz, DMSO-$d_6$) δ [ppm] 11.89 (s, 1 H), 10.27 (s, 1 H), 9.95 (s, 1 H), 7.30 (dd, 1 H), 7.23-7.01 (m, 6 H), 6.99 (s, 1 H), 6.30 (s, 1 H), 4.49 (s, 2 H), 2.74 (s, 3 H), 2.13 (s, 3 H) | |
| "A52" | 5-{2,4-Dihydroxy-5-[N-(3-chloro-6-methoxybenzyl)-N-methylaminocarbonyl]phenyl}-4-(2-chlorophenyl)-3-hydroxy-4H-1,2,4-triazole | 516.4 |
| "A53" | 5-{2,4-Dihydroxy-5-[N-(3-chloro-6-methoxybenzyl)-N-methylaminocarbonyl]phenyl}-4-(2-fluorophenyl)-3-hydroxy-4H-1,2,4-triazole | 499.9 |
| "A54" | 5-{2,4-Dihydroxy-5-[N-(3-fluoro-6-methoxybenzyl)-N-methylaminocarbonyl]phenyl}-4-(2-methylphenyl)-3-hydroxy-4H-1,2,4-triazole | 479.5 |

-continued

| Compound No. | Structure/Name | MW |
|---|---|---|
| "A55" | 5-{2,4-Dihydroxy-5-[N-(3-fluoro-6-methoxybenzyl)-N-methylaminocarbonyl]phenyl}-4-(2-chlorophenyl)-3-hydroxy-4H-1,2,4-triazole | 499.9 |
| "A56" | 5-{2,4-Dihydroxy-5-[N-(3-fluoro-6-methoxybenzyl)-N-methylaminocarbonyl]phenyl}-4-(2-fluorophenyl)-3-hydroxy-4H-1,2,4-triazole | 483.4 |
| "A57" | 5-{2,4-Dihydroxy-5-[N-(furan-2-ylmethyl)-N-methyl-aminocarbonyl]phenyl}-4-(2-methylphenyl)-3-hydroxy-4H-1,2,4-triazole | 421.4 |

$^1$H NMR (500 MHz, DMSO-$d_6$) δ [ppm] 11.92 (s, 1 H), 10.13 (s, 1 H), 9.97 (s, 1 H), 7.62 (s, 1 H), 7.27-6.97 (m, 6 H), 6.44 (s, 1 H), 6.29 (s, 1 H), 4.45 (s, 2 H), 2.75 (s, 3 H), 2.15 (s, 3 H)

| | | |
|---|---|---|
| "A57a" | 5-{2,4-Dihydroxy-5-[N-(furan-2-ylmethyl)-N-methyl-aminocarbonyl]phenyl}-4-phenyl-3-hydroxy-4H-1,2,4-triazole | 407.4 |

$^1$H NMR (500 MHz, DMSO-$d_6$) δ [ppm] 11.95 (s, 1 H), 10.16 (s, 1 H), 9.93 (s, 1 H), 7.60 (s, 1 H), 7.33-7.25 (m, 3 H), 7.15-7.13 (m, 2 H), 7.04 (s, 1 H), 6.41 (dd, 1 H), 6.29 (s, 1 H), 6.26 (bs, 1 H), 4.45 (bs, 2 H), 2.78 (s, 3 H)

| | | |
|---|---|---|
| "A57b" | 5-{2,4-Dihydroxy-5-[N-(furan-2-ylmethyl)-N-methyl-aminocarbonyl]phenyl}-4-(3-methylphenyl)-3-hydroxy-4H-1,2,4-triazole | 421.4 |

$^1$H NMR (500 MHz, DMSO-$d_6$) δ [ppm] 11.90 (s, 1 H), 10.14 (s, 1 H), 9.93 (s, 1 H), 7.60 (s, 1 H), 7.18 (dd, 1 H), 7.08 (d, 1 H), 7.03 (s, 1 H), 7.00 (s, 1 H), 6.90 (d, 1 H), 6.41 (t, 1 H), 6.30 (s, 1 H), 6.26 (bs, 1 H), 4.45 (bs, 2 H), 2.78 (s, 3 H), 2.19 (s, 3 H)

| | | |
|---|---|---|
| "A58" | 5-{2,4-Dihydroxy-5-[N-(furan-2-ylmethyl)-N-methyl-aminocarbonyl]phenyl}-4-(2-chlorophenyl)-3-hydroxy-4H-1,2,4-triazole | 441.8 |

$^1$H NMR (500 MHz, DMSO-$d_6$) δ [ppm] 11.95 (s, 1 H), 10.15 (s, 1 H), 10.00 (s, 1 H), 7.60 (s, 1 H), 7.51 (d, 1 H), 7.41-7.32 (m, 3 H), 6.95 (s, 1 H), 6.42 (dd, 1 H), 6.28 (s, 1 H), 6.23 (bs, 1 H), 4.44 (bs, 2 H), 2.73 (s, 3 H)

| | | |
|---|---|---|
| "A58a" | 5-{2,4-Dihydroxy-5-[N-(furan-2-ylmethyl)-N-methyl-aminocarbonyl]phenyl}-4-(3-chlorophenyl)-3-hydroxy-4H-1,2,4-triazole | 441.8 |

$^1$H NMR (500 MHz, DMSO-$d_6$) δ [ppm] 12.00 (s, 1 H), 10.19 (s, 1 H), 9.96 (s, 1 H), 7.59 (s, 1 H), 7.36-7.32 (m, 3 H), 7.27 (s, 1 H), 7.11 (m, 2 H), 7.10 (bs, 1 H), 6.40 (s, 1 H), 6.31 (s, 1 H), 6.27 (bs, 1 H), 4.49 (bs, 2 H), 2.81 (s, 3 H)

| | | |
|---|---|---|
| "A58b" | 5-{2,4-Dihydroxy-5-[N-(furan-2-ylmethyl)-N-methyl-aminocarbonyl]phenyl}-4-(3,5-dichlorophenyl)-3-hydroxy-4H-1,2,4-triazole | 476.3 |

$^1$H NMR (500 MHz, DMSO-$d_6$) δ [ppm] 12.07 (s, 1 H), 10.23 (s, 1 H), 10.02 (s, 1 H), 7.59 (s, 1 H), 7.55 (t, 1 H), 7.24 (d, 2 H), 7.16 (s, 1 H), 6.40 (s, 1 H), 6.33 (s, 1 H), 6.28 (bs, 1 H), 4.50 (bs, 2 H), 2.82 (s, 3 H)

| | | |
|---|---|---|
| "A58c" | 5-{2,4-Dihydroxy-5-[N-(furan-2-ylmethyl)-N-methyl-aminocarbonyl]phenyl}-4-(4-chlorophenyl)-3-hydroxy-4H-1,2,4-triazole | 441.8 |

$^1$H NMR (500 MHz, DMSO-$d_6$) δ [ppm] 11.97 (s, 1 H), 10.20 (s, 1 H), 9.92 (s, 1 H), 7.60 (s, 1 H), 7.39 (d, 2 H), 7.17 (d, 2 H), 7.09 (s, 1 H), 6.42 (t, 1 H), 6.30 (s, 1 H), 6.27 (bs, 1 H), 4.47 (bs, 2 H), 2.80 (s, 3 H)

| | | |
|---|---|---|
| "A59" | 5-{2,4-Dihydroxy-5-[N-(furan-2-ylmethyl)-N-methyl-aminocarbonyl]phenyl}-4-(2-fluorophenyl)-3-hydroxy-4H-1,2,4-triazole | 425.4 |
| "A59a" | 5-{2,4-Dihydroxy-5-[N-(furan-2-ylmethyl)-N-methyl-aminocarbonyl]phenyl}-4-(3-fluorophenyl)-3-hydroxy-4H-1,2,4-triazole | 425.4 |

$^1$H NMR (500 MHz, DMSO-$d_6$) δ [ppm] 11.99 (s, 1 H), 10.20 (s, 1 H), 9.96 (s, 1 H), 7.59 (s, 1 H), 7.35 (dd, 1 H), 7.14 (dq, 1 H), 7.10 (s, 1 H), 7.06 (dt, 1 H), 6.97 (dd, 1 H), 6.41 (t, 1 H), 6.39 (s, 1 H), 6.27 (bs, 1 H), 4.48 (bs, 2 H), 2.80 (s, 3 H)

| | | |
|---|---|---|
| "A59b" | 5-{2,4-Dihydroxy-5-[N-(furan-2-ylmethyl)-N-methyl-aminocarbonyl]phenyl}-4-(3-ethylphenyl)-3-hydroxy-4H-1,2,4-triazole | 435.5 |

$^1$H NMR (500 MHz, DMSO-$d_6$) δ [ppm] 11.90 (s, 1 H), 10.14 (s, 1 H), 9.91 (s, 1 H), 7.59 (s, 1 H), 7.22 (t, 1 H), 7.10 (d, 1 H), 7.04 (s, 1 H), 7.00 (d, 1 H), 6.94 (s, 1 H), 6.41 (t, 1 H), 6.31 (s, 1 H), 6.26 (bs, 1 H), 4.45 (bs, 2 H), 2.77 (s, 3 H), 2.45 (q, 2 H), 1.00 (t, 3 H)

| | | |
|---|---|---|
| "A60" | 5-{2,4-Dihydroxy-5-[N-(furan-3-ylmethyl)-N-methyl-aminocarbonyl]phenyl}-4-(2-methylphenyl)-3-hydroxy-4H-1,2,4-triazole | 421.4 |
| "A61" | 5-{2,4-Dihydroxy-5-[N-(furan-3-ylmethyl)-N-methyl-aminocarbonyl]phenyl}-4-(2-chlorophenyl)-3-hydroxy-4H-1,2,4-triazole | 441.8 |
| "A62" | 5-{2,4-Dihydroxy-5-[N-(furan-3-ylmethyl)-N-methyl-aminocarbonyl]phenyl}-4-(2-fluorophenyl)-3-hydroxy-4H-1,2,4-triazole | 425.4 |
| "A62a" | 5-{2,4-Dihydroxy-5-[N-(thiophen-2-ylmethyl)-N-methylaminocarbonyl]phenyl}-4-(2-methylphenyl)-3-hydroxy-4H-1,2,4-triazole | 437.5 |

-continued

| Compound No. | Structure/Name | MW |
|---|---|---|

¹H NMR (500 MHz, DMSO-d₆) δ [ppm] 11.90 (s, 1 H), 10.15 (s, 1 H), 9.97 (s, 1 H), 7.46 (d, 1 H), 7.26-6.96 (m, 7 H), 6.28 (s, 1 H), 4.62 (bs, 2 H), 2.71 (s, 3 H), 2.14 (s, 3 H)

"A62b"   5-{2,4-Dihydroxy-5-[N-(furan-2-ylmethyl)-N-methyl-aminocarbonyl]phenyl}-4-(3-methoxyphenyl)-3-hydroxy-4H-1,2,4-triazole   437.4

¹H NMR (500 MHz, DMSO-d₆) δ [ppm] 11.91 (s, 1 H), 10.15 (s, 1 H), 9.95 (s, 1 H), 7.59 (s, 1 H), 7.21 (t, 1 H), 7.05 (s, 1 H), 6.84 (d, 1 H), 6.74 (s, 1 H), 6.72 (s, 1 H), 6.40 (t, 1 H), 6.32 (s, 1 H), 6.25 (bs, 1 H), 4.53 (bs, 2 H), 3.62 (s, 3 H), 2.78 (s, 3 H)

"A62c"   5-{2,4-Dihydroxy-5-[N-(furan-2-ylmethyl)-N-methyl-aminocarbonyl]phenyl}-4-(2-ethylphenyl)-3-hydroxy-4H-1,2,4-triazole   435.5

¹H NMR (500 MHz, DMSO-d₆) δ [ppm] 11.91 (s, 1 H), 10.14 (s, 1 H), 10.00 (s, 1 H), 7.61 (s, 1 H), 7.29 (d, 1 H), 7.11 (m, 1 H), 7.06 (d, 1 H), 6.90 (s, 1 H), 6.42 (t, 1 H), 6.29 (s, 1 H), 6.22 (bs, 1 H), 4.41 (bs, 2 H), 2.70 (s, 3 H), 2.44 (q, 2 H), 1.05 (t, 2 H)

"A63"   518.6

"A64"   539.0

"A65"   522.5

"A66"   504.6

-continued

| Compound No. | Structure/Name | MW |
|---|---|---|
| "A67" | | 525.0 |
| "A68" | | 508.5 |
| "A69" | 5-{2,4-Dihydroxy-5-[N-(2-aminoethoxybenzyl)-N-methylaminocarbonyl]phenyl}-4-(2-methylphenyl)-3-hydroxy-4H-1,2,4-triazole | 490.5 |
| "A70" | 5-{2,4-Dihydroxy-5-[N-(2-aminoethoxybenzyl)-N-methylaminocarbonyl]phenyl}-4-(2-chlorophenyl)-3-hydroxy-4H-1,2,4-triazole | 510.9 |
| "A71" | 5-{2,4-Dihydroxy-5-[N-(2-aminoethoxybenzyl)-N-methylaminocarbonyl]phenyl}-4-(2-fluorophenyl)-3-hydroxy-4H-1,2,4-triazole | 494.5 |
| "A72" | 5-{2,4-Dihydroxy-5-[N-(2-hydroxyethoxybenzyl)-N-methylaminocarbonyl]phenyl}-4-(2-methylphenyl)-3-hydroxy-4H-1,2,4-triazole | 491.5 |
| "A73" | 5-{2,4-Dihydroxy-5-[N-(2-hydroxyethoxybenzyl)-N-methylaminocarbonyl]phenyl}-4-(2-chlorophenyl)-3-hydroxy-4H-1,2,4-triazole | 511.9 |
| "A74" | 5-{2,4-Dihydroxy-5-[N-(2-hydroxyethoxybenzyl)-N-methylaminocarbonyl]phenyl}-4-(2-fluorophenyl)-3-hydroxy-4H-1,2,4-triazole | 495.5 |
| "A75" | | 532.6 |
| "A76" | | 553.0 |

-continued

| Compound No. | Structure/Name | MW |
|---|---|---|
| "A77" | | 536.6 |
| "A78" | | 504.5 |
| "A79" | | 524.9 |
| "A80" | | 508.5 |
| "A81" | 5-{2,4-Dihydroxy-5-[N-(1-methylpyrrol-2-ylmethyl)-N-methylaminocarbonyl]phenyl}-4-(2-methylphenyl)-3-hydroxy-4H-1,2,4-triazole | 434.5 |
| "A82" | 5-{2,4-Dihydroxy-5-[N-(1-methylpyrrol-2-ylmethyl)-N-methylaminocarbonyl]phenyl}-4-(2-chlorophenyl)-3-hydroxy-4H-1,2,4-triazole | 454.9 |

-continued

| Compound No. | Structure/Name | MW |
|---|---|---|
| "A83" | 5-{2,4-Dihydroxy-5-[N-(1-methylpyrrol-2-ylmethyl)-N-methylaminocarbonyl]phenyl}-4-(2-fluorophenyl)-3-hydroxy-4H-1,2,4-triazole | 438.4 |
| "A84" | 5-{2,4-Dihydroxy-5-[N-(isoxazol-3-ylmethyl)-N-methylaminocarbonyl]phenyl}-4-(2-methylphenyl)-3-hydroxy-4H-1,2,4-triazole | 422.4 |
| "A85" | 5-{2,4-Dihydroxy-5-[N-(isoxazol-3-ylmethyl)-N-methylaminocarbonyl]phenyl}-4-(2-chlorophenyl)-3-hydroxy-4H-1,2,4-triazole | 442.8 |
| "A86" | 5-{2,4-Dihydroxy-5-[N-(isoxazol-3-ylmethyl)-N-methylaminocarbonyl]phenyl}-4-(2-fluorophenyl)-3-hydroxy-4H-1,2,4-triazole | 426.4 |
| "A87" | 5-{2,4-Dihydroxy-5-[N-(pyridazin-3-ylmethyl)-N-methylaminocarbonyl]phenyl}-4-(2-methylphenyl)-3-hydroxy-4H-1,2,4-triazole | 433.4 |
| "A88" | 5-{2,4-Dihydroxy-5-[N-(pyridazin-3-ylmethyl)-N-methylaminocarbonyl]phenyl}-4-(2-chlorophenyl)-3-hydroxy-4H-1,2,4-triazole | 453.9 |
| "A89" | 5-{2,4-Dihydroxy-5-[N-(pyridazin-3-ylmethyl)-N-methylaminocarbonyl]phenyl}-4-(2-fluorophenyl)-3-hydroxy-4H-1,2,4-triazole | 437.4 |
| "A90" | 5-{2,4-Dihydroxy-5-[N-(pyrazin-2-ylmethyl)-N-methylaminocarbonyl]phenyl}-4-(2-methylphenyl)-3-hydroxy-4H-1,2,4-triazole | 433.4 |
| "A91" | 5-{2,4-Dihydroxy-5-[N-(pyrazin-2-ylmethyl)-N-methylaminocarbonyl]phenyl}-4-(2-chlorophenyl)-3-hydroxy-4H-1,2,4-triazole | 453.9 |
| "A92" | 5-{2,4-Dihydroxy-5-[N-(pyrazin-2-ylmethyl)-N-methylaminocarbonyl]phenyl}-4-(2-fluorophenyl)-3-hydroxy-4H-1,2,4-triazole | 437.4 |
| "A93" | 5-{2,4-Dihydroxy-5-[N-(2-aminocarbonyl-5-chlorobenzyl)-N-methylaminocarbonyl]phenyl}-4-(2-methylphenyl)-3-hydroxy-4H-1,2,4-triazole | 508.9 |
| "A94" | 5-{2,4-Dihydroxy-5-[N-(2-aminocarbonyl-5-chlorobenzyl)-N-methylaminocarbonyl]phenyl}-4-(2-chlorophenyl)-3-hydroxy-4H-1,2,4-triazole | 529.4 |
| "A95" | 5-{2,4-Dihydroxy-5-[N-(2-aminocarbonyl-5-chlorobenzyl)-N-methylaminocarbonyl]phenyl}-4-(2-fluorophenyl)-3-hydroxy-4H-1,2,4-triazole | 512.9 |
| "A96" | 5-(2,4-Dihydroxy-5-{N-[3-(2-methylaminoethoxy)-benzyl]-N-methylaminocarbonyl}phenyl)-4-(2-methylphenyl)-3-hydroxy-4H-1,2,4-triazole | 504.6 |
| "A97" | 5-(2,4-Dihydroxy-5-{N-[3-(2-methylaminoethoxy)-benzyl]-N-methylaminocarbonyl}phenyl)-4-(2-chlorophenyl)-3-hydroxy-4H-1,2,4-triazole | 525.0 |
| "A98" | 5-(2,4-Dihydroxy-5-{N-[3-(2-methylaminoethoxy)-benzyl]-N-methylaminocarbonyl}phenyl)-4-(2-fluorophenyl)-3-hydroxy-4H-1,2,4-triazole | 508.5 |
| "A99" | 5-{2,4-Dihydroxy-5-[N-(2,3-dimethoxybenzyl)-N-methylaminocarbonyl]phenyl}-4-(2-methylphenyl)-3-hydroxy-4H-1,2,4-triazole | 491.5 |
| "A100" | 5-{2,4-Dihydroxy-5-[N-(2,3-dimethoxybenzyl)-N-methylaminocarbonyl]phenyl}-4-(2-chlorophenyl)-3-hydroxy-4H-1,2,4-triazole | 511.9 |
| "A101" | 5-{2,4-Dihydroxy-5-[N-(2,3-dimethoxybenzyl)-N-methylaminocarbonyl]phenyl}-4-(2-fluorophenyl)-3-hydroxy-4H-1,2,4-triazole | 495.5 |
| "A102" | 5-(2,4-Dihydroxy-5-{N-[2-(2-cyanoethoxy)benzyl]-N-methylaminocarbonyl}phenyl)-4-(2-methylphenyl)-3-hydroxy-4H-1,2,4-triazole | 500.5 |
| "A103" | 5-(2,4-Dihydroxy-5-{N-[2-(2-cyanoethoxy)benzyl]-N-methylaminocarbonyl}phenyl)-4-(2-chlorophenyl)-3- | 520.9 |

| Compound No. | Structure/Name | MW |
|---|---|---|
| | hydroxy-4H-1,2,4-triazole | |
| "A104" | 5-(2,4-Dihydroxy-5-{N-[2-(2-cyanoethoxy)benzyl]-N-methylaminocarbonyl}phenyl)-4-(2-fluorophenyl)-3-hydroxy-4H-1,2,4-triazole | 504.5 |
| "A105" | 5-{2,4-Dihydroxy-5-[N-(4-fluorobenzyl)-N-methyl-aminocarbonyl]phenyl}-4-(2-methyl-aminomethylphenyl)-3-hydroxy-4H-1,2,4-triazole | 478.5 |
| "A106" | 5-{2,4-Dihydroxy-5-[N-(4-fluorobenzyl)-N-methyl-aminocarbonyl]phenyl}-4-(3-aminomethylphenyl)-3-hydroxy-4H-1,2,4-triazole | 464.5 |
| "A107" | 5-[2,4-Dihydroxy-5-(N-benzyl-N-methyl-aminocarbonyl)phenyl]-4-(2-cyanophenyl)-3-hydroxy-4H-1,2,4-triazole | 442.4 |
| "A108" | 5-[2,4-Dihydroxy-5-(N-benzyl-N-methyl-aminocarbonyl)phenyl]-4-(2-ethylphenyl)-3-hydroxy-4H-1,2,4-triazole | 445.5 |
| "A109" | 5-{2,4-Dihydroxy-5-[N-(benzo-1,4-dioxan-5-yl)-N-methylaminocarbonyl]phenyl}-4-(2-methylphenyl)-3-hydroxy-4H-1,2,4-triazole | 489.5 |

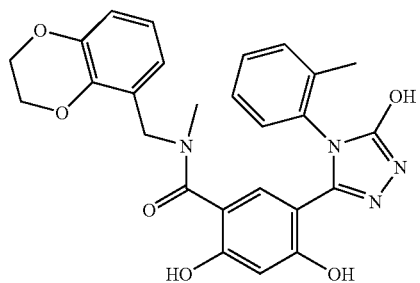

| | | |
|---|---|---|
| "A110" | 5-{2,4-Dihydroxy-5-[N-(2-isopropylbenzyl)-N-methyl-aminocarbonyl]phenyl}-4-(2-chlorophenyl)-3-hydroxy-4H-1,2,4-triazole | 494.0 |
| "A111" | 5-{2,4-Dihydroxy-5-[N-(2-aminomethylbenzyl)-N-methylaminocarbonyl]phenyl}-4-(2-chlorophenyl)-3-hydroxy-4H-1,2,4-triazole | 480.9 |
| "A112" | 5-{2,4-Dihydroxy-5-[N-(2-methylaminomethyl-benzyl)-N-methylaminocarbonyl]phenyl}-4-(2-chlorophenyl)-3-hydroxy-4H-1,2,4-triazole | 495.0 |
| "A113" | 5-(2,4-Dihydroxy-5-{N-[2-(2-methoxyethoxy)benzyl]-N-methylaminocarbonyl}phenyl)-4-(2-chlorophenyl)-3-hydroxy-4H-1,2,4-triazole | 525.0 |
| "A114" | 5-{2,4-Dihydroxy-5-[N-(2-isopropylamino-methylbenzyl)-N-methylaminocarbonyl]phenyl}-4-(2-methylphenyl)-3-hydroxy-4H-1,2,4-triazole | 502.6 |
| "A115" | 5-[2,4-Dihydroxy-5-(N-benzyl-N-methylamino-carbonyl)phenyl]-4-[4-(3-cyanopropoxy)phenyl]-3-hydroxy-4H-1,2,4-triazole | 500.5 |
| "A116" | 5-{2,4-Dihydroxy-5-[N-(2-aminomethylbenzyl)-N-methylaminocarbonyl]phenyl}-4-(2-fluorophenyl)-3-hydroxy-4H-1,2,4-triazole | 464.5 |
| "A116a" | 5-[2-Hydroxy-4-methoxy-5-(N-benzyl-N-methyl-aminocarbonyl)phenyl]-4-(2-methylphenyl)-3-hydroxy-4H-1,2,4-triazole | 445.5 |

$^1$H NMR (500 MHz, DMSO-$d_6$) δ [ppm] 11.94 (s, 1 H), 10.20 (s, 1 H), 7.42-6.77 (m, 10 H), 6.42 (s, 1 H), 4.60 (s, 2 H), 3.72 (s, 3 H), 2.80 (s, 3 H), 2.15 (s, 3 H)

| "A116b" | 2,4-Dihydroxy-N-methyl-5-(5-oxo-4-o-tolyl-4,5-dihydro-1H-1,2,4-triazol-3-yl)-N-(2-pyridin-3-yl-benzyl)benzamide | 508.5 |

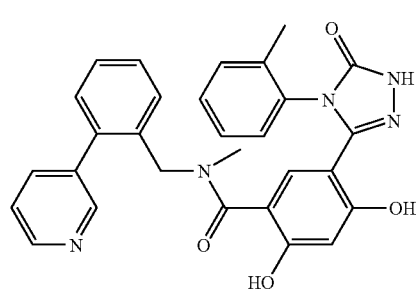

| Compound No. | Structure/Name | MW |
|---|---|---|
| | ¹H NMR (500 MHz, DMSO-d₆) δ [ppm] 11.98 (s, 1 H), 10.16 (s, 1 H), 9.94 (s, 1 H), 8.61 (s, 1 H), 7.81-6.98 (m, 11 H), 6.90 (s, 1 H), 6.26 (s, 1 H), 4.52 (s, 2 H), 2.57 (s, 3 H), 2.11 (s, 3 H) | |
| "A116c" | 2,4-Dihydroxy-N-methyl-N-[3-(2-morpholin-4-yl-ethoxy)benzyl]-5-(5-oxo-4-o-tolyl-4,5-dihydro-1H-1,2,4-triazol-3-yl)benzamide | 560.6 |
| | ¹H NMR (500 MHz, DMSO-d₆) δ [ppm] 11.90 (s, 1 H), 10.20 (s, 1 H), 9.96 (s, 1 H), 8.16 (s, 1 H), 7.25-6.72 (m, 8 H), 6.28 (s, 1 H), 4.48 (s, 2 H), 4.06 (t, 2 H), 3.57 (t, 4 H), 2.73 (s, 3 H), 2.68 (t, 4 H), 2.46 (t, 2 H), 2.13 (s, 3 H) | |
| "A116d" | 2,4-Dihydroxy-N-methyl-5-(5-oxo-4-o-tolyl-4,5-dihydro-1H-1,2,4-triazol-3-yl)-N-(3-pyrimidin-5-yl-benzyl)benzamide | 509.5 |
| "A117" | 5-{2,4-Dihydroxy-5-[N-(2-aminomethylbenzyl)-N-methylaminocarbonyl]phenyl}-4-(2-methylphenyl)-3-hydroxy-4H-1,2,4-triazole | 460.5 |

EXAMPLE 2

Preparation of 5-[2,4-dihydroxy-5-(N-propyl-N-methylsulfamoyl)phenyl]-4-(2-chlorophenyl)-3-hydroxy-4H-1,2,4-triazole ("A117a")

2.1 1 ml of conc. sulfuric acid is added to a solution of 100 g of 2,4-dimethoxybenzoic acid in 500 ml of methanol, and the mixture is refluxed for 14 hours. The mixture is cooled, the solvent is removed, the residue is dissolved in 1 litre of MTB, the solution is washed three times with 200 ml of water each time and dried, and the solvent is removed, giving 105.5 g of methyl 2,4-dimethoxybenzoate.

2.2 93.9 g of methyl 2,4-dimethoxybenzoate are added slowly, at a max. of 5°, to 128 ml of chlorosulfonic acid cooled to −5°. The mixture is stirred at 0° for 1.5 hours and at room temperature for 14 hours. The batch is poured onto ice, and the white precipitate is separated off and rinsed with a little water (=sulfonic acid chloride). The filtrate is adjusted to about pH 2 using potassium carbonate, and the precipitated material is subsequently separated off (=sulfonic acid K salt). The two crystallisates are dried, giving 24.8 g of

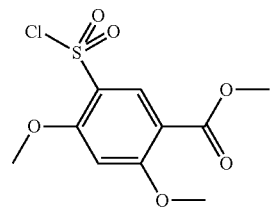

and 134.3 g of

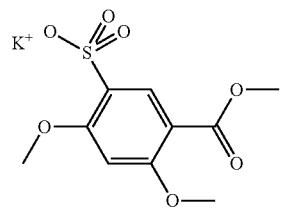

2.3 300 ml of phosphoryl chloride are added to 134.3 g of the potassium salt obtained in 2.2, and the mixture is stirred at 110° for 1 hour. The POCl₃ is removed. The residue is stirred with 500 g of ice for 1 hour. The entire mixture is filtered through a glass frit with suction. The filter cake is washed with water, giving 122 g of a mixture of 78.4% of

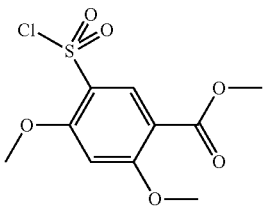

and 20.4% of

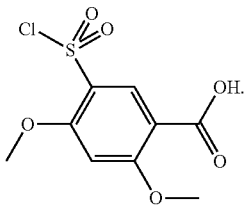

2.4 122 g of the product mixture obtained in 2.3 are added with stirring and cooling to a solution of 42 ml of methylpropylamine and 115 ml of triethylamine in 500 ml of THF, and the mixture is stirred at room temperature for a further 14 hours. Conventional work-up gives 104 g of a mixture of 84.4% of

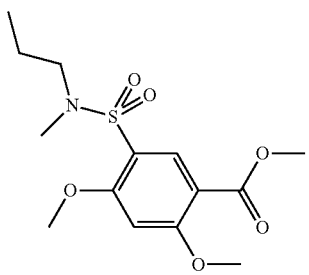

and 15.6% of

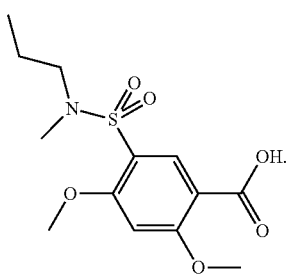

2.5 In order to remove residual moisture, the product mixture from 2.4 is treated with 500 ml of toluene. The residue is dissolved in dichloromethane, boron tribromide is added with cooling, and the mixture is stirred at room temperature for 14 hours. In order to decompose BBr₃, acetonitrile/water is added with cooling. The precipitated boric acid is separated off. The filtrate is subjected to conventional work-up, and crystallisation from toluene gives the compound 2,4-dihydroxy-5-(N-methyl-N-propylsulfamoyl)benzoic acid

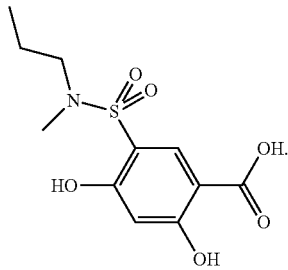

2.6 Esterification of 2,4-dihydroxy-5-(N-methyl-N-propylsulfamoyl)benzoic acid in methanol with catalysis by sulfuric acid under standard conditions gives the compound methyl 2,4-dihydroxy-5-(N-methyl-N-propylsulfamoyl) benzoate.

2.7 71.25 g of potassium carbonate are added to a solution of 75 g of methyl 2,4-dihydroxy-5-(N-methyl-N-propylsulfamoyl)benzoate in 800 ml of acetonitrile. 60 ml of benzyl bromide are subsequently added dropwise. The mixture is refluxed for 3 hours, cooled and subjected to conventional work-up. HPLC gives 113 g of methyl 2,4-dibenzyloxy-5-(N-methyl-N-propylsulfamoyl)benzoate.

2.8 113 g of methyl 2,4-dibenzyloxy-5-(N-methyl-N-propylsulfamoyl)benzoate are dissolved in 300 ml of methanol and 300 ml of THF, 600 ml of 2 N NaOH are added, and the mixture is stirred at room temperature for 14 hours. Some of the solvent is removed, and the mixture is neutralised using dilute HCl with ice-cooling. The precipitated product is separated off and dried, giving 2,4-dibenzyloxy-5-(N-methyl-N-propylsulfamoyl)benzoic acid in quantitative yield.

2.9 Reaction of 2,4-dibenzyloxy-5-(N-methyl-N-propylsulfamoyl)benzoic acid with thionyl chloride gives the compound 2,4-dibenzyloxy-5-(N-methyl-N-propylsulfamoyl) benzoyl chloride.

2.10 Reaction of 2,4-dibenzyloxy-5-(N-methyl-N-propylsulfamoyl)benzoyl chloride with 2-chloroaniline gives the compound 2,4-dibenzyloxy-5-(N-methyl-N-propylsulfamoyl)-N-(2-chlorophenyl)benzamide.

2.11 Reaction of 2,4-dibenzyloxy-5-(N-methyl-N-propylsulfamoyl)-N-(2-chlorophenyl)benzamide with hydrazine gives the compound

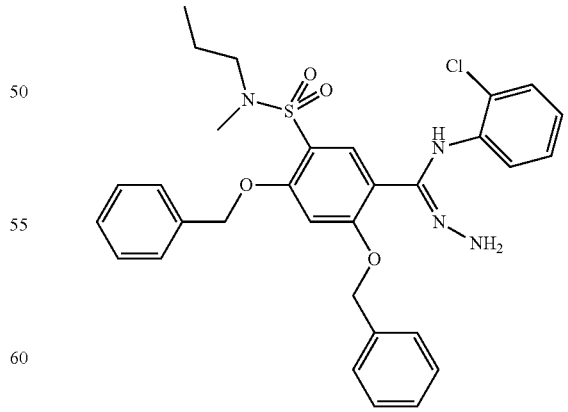

2.12 Cyclisation thereof gives the compound 5-[2,4-dibenzyloxy-5-(N-propyl-N-methylsulfamoyl)phenyl]-4-(2-chlorophenyl)-3-hydroxy-4H-1,2,4-triazole, and removal of the benzyl groups thereof by catalytic hydrogenation gives the compound 5-[2,4-dihydroxy-5-(N-propyl-N-methylsulfamoyl)phenyl]-4-(2-chlorophenyl)-3-hydroxy-4H-1,2,4-triazole ("A117a"), MW 439.9.

The following compounds are obtained analogously:

| | | |
|---|---|---|
| "A118" | 5-{2,4-Dihydroxy-5-[N-(2-methoxybenzyl)-N-methylaminosulfonyl]phenyl}-4-(2-methylphenyl)-3-hydroxy-4H-1,2,4-triazole | 497.5 |

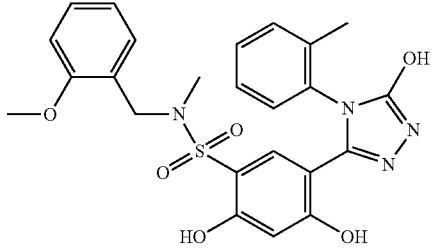

| | | |
|---|---|---|
| "A119" | 5-{2,4-Dihydroxy-5-[N-(2-methoxybenzyl)-N-methylaminosulfonyl]phenyl}-4-(2-chlorophenyl)-3-hydroxy-4H-1,2,4-triazole | 518.0 |
| "A120" | 5-{2,4-Dihydroxy-5-[N-(2-methoxybenzyl)-N-methylaminosulfonyl]phenyl}-4-(2-fluorophenyl)-3-hydroxy-4H-1,2,4-triazole | 501.5 |
| "A121" | 5-{2,4-Dihydroxy-5-[N-(2-fluorobenzyl)-N-methylaminosulfonyl]phenyl}-4-(2-methylphenyl)-3-hydroxy-4H-1,2,4-triazole | 485.5 |
| "A122" | 5-{2,4-Dihydroxy-5-[N-(2-fluorobenzyl)-N-methylaminosulfonyl]phenyl}-4-(2-chlorophenyl)-3-hydroxy-4H-1,2,4-triazole | 505.9 |
| "A123" | 5-{2,4-Dihydroxy-5-[N-(2-fluorobenzyl)-N-methylaminosulfonyl]phenyl}-4-(2-fluorophenyl)-3-hydroxy-4H-1,2,4-triazole | 489.5 |
| "A124" | 5-{2,4-Dihydroxy-5-[N-(4-fluorobenzyl)-N-methylaminosulfonyl]phenyl}-4-(2-methylphenyl)-3-hydroxy-4H-1,2,4-triazole | 485.5 |
| "A125" | 5-{2,4-Dihydroxy-5-[N-(4-fluorobenzyl)-N-methylaminosulfonyl]phenyl}-4-(2-chlorophenyl)-3-hydroxy-4H-1,2,4-triazole | 505.9 |
| "A126" | 5-{2,4-Dihydroxy-5-[N-(4-fluorobenzyl)-N-methylaminosulfonyl]phenyl}-4-(2-fluorophenyl)-3-hydroxy-4H-1,2,4-triazole | 489.5 |
| "A127" | 5-{2,4-Dihydroxy-5-[N-(3-fluorobenzyl)-N-methylaminosulfonyl]phenyl}-4-(2-methylphenyl)-3-hydroxy-4H-1,2,4-triazole | 485.5 |
| "A128" | 5-{2,4-Dihydroxy-5-[N-(3-fluorobenzyl)-N-methylaminosulfonyl]phenyl}-4-(2-chlorophenyl)-3-hydroxy-4H-1,2,4-triazole | 505.9 |
| "A129" | 5-{2,4-Dihydroxy-5-[N-(3-fluorobenzyl)-N-methylaminosulfonyl]phenyl}-4-(2-fluorophenyl)-3-hydroxy-4H-1,2,4-triazole | 489.5 |
| "A130" | 5-{2,4-Dihydroxy-5-[N-(3-methylbenzyl)-N-methylaminosulfonyl]phenyl}-4-(2-methylphenyl)-3-hydroxy-4H-1,2,4-triazole | 481.5 |
| "A131" | 5-{2,4-Dihydroxy-5-[N-(3-methylbenzyl)-N-methylaminosulfonyl]phenyl}-4-(2-chlorophenyl)-3-hydroxy-4H-1,2,4-triazole | 502.0 |
| "A132" | 5-{2,4-Dihydroxy-5-[N-(3-methylbenzyl)-N-methylaminosulfonyl]phenyl}-4-(2-fluorophenyl)-3-hydroxy-4H-1,2,4-triazole | 485.5 |
| "A133" | 5-{2,4-Dihydroxy-5-[N-(4-methylbenzyl)-N-methylaminosulfonyl]phenyl}-4-(2-methylphenyl)-3-hydroxy-4H-1,2,4-triazole | 481.5 |
| "A134" | 5-{2,4-Dihydroxy-5-[N-(4-methylbenzyl)-N-methylaminosulfonyl]phenyl}-4-(2-chlorophenyl)-3-hydroxy-4H-1,2,4-triazole | 502.0 |
| "A135" | 5-{2,4-Dihydroxy-5-[N-(4-methylbenzyl)-N-methylaminosulfonyl]phenyl}-4-(2-fluorophenyl)-3-hydroxy-4H-1,2,4-triazole | 485.5 |
| "A136" | 5-{2,4-Dihydroxy-5-[N-(3-chlorobenzyl)-N-methylaminosulfonyl]phenyl}-4-(2-methylphenyl)-3-hydroxy-4H-1,2,4-triazole | 502.0 |
| "A137" | 5-{2,4-Dihydroxy-5-[N-(3-chlorobenzyl)-N-methylaminosulfonyl]phenyl}-4-(2-chlorophenyl)-3-hydroxy-4H-1,2,4-triazole | 522.4 |
| "A138" | 5-{2,4-Dihydroxy-5-[N-(3-chlorobenzyl)-N-methylaminosulfonyl]phenyl}-4-(2-fluorophenyl)-3-hydroxy-4H-1,2,4-triazole | 505.9 |
| "A139" | 5-{2,4-Dihydroxy-5-[N-(2-chlorobenzyl)-N-methylaminosulfonyl]phenyl}-4-(2-methylphenyl)-3-hydroxy-4H-1,2,4-triazole | 502.0 |
| "A140" | 5-{2,4-Dihydroxy-5-[N-(2-chlorobenzyl)-N-methylaminosulfonyl]phenyl}-4-(2-chlorophenyl)-3-hydroxy-4H-1,2,4-triazole | 522.4 |
| "A141" | 5-{2,4-Dihydroxy-5-[N-(2-chlorobenzyl)-N-methylaminosulfonyl]phenyl}-4-(2-fluorophenyl)-3-hydroxy-4H-1,2,4-triazole | 505.9 |
| "A142" | 5-{2,4-Dihydroxy-5-[N-(pyridin-2-ylmethyl)-N-methylaminosulfonyl]phenyl}-4-(2-methylphenyl)-3-hydroxy-4H-1,2,4-triazole | 468.5 |
| "A143" | 5-{2,4-Dihydroxy-5-[N-(pyridin-2-ylmethyl)-N-methylaminosulfonyl]phenyl}-4-(2-chlorophenyl)-3-hydroxy-4H-1,2,4-triazole | 488.9 |
| "A144" | 5-{2,4-Dihydroxy-5-[N-(pyridin-2-ylmethyl)-N-methylaminosulfonyl]phenyl}-4-(2-fluorophenyl)-3-hydroxy-4H-1,2,4-triazole | 472.5 |
| "A145" | 5-{2,4-Dihydroxy-5-[N-(pyridin-3-ylmethyl)-N-methylaminosulfonyl]phenyl}-4-(2-methylphenyl)-3-hydroxy-4H-1,2,4-triazole | 468.5 |
| "A146" | 5-{2,4-Dihydroxy-5-[N-(pyridin-3-ylmethyl)-N-methylaminosulfonyl]phenyl}-4-(2-chlorophenyl)-3-hydroxy-4H-1,2,4-triazole | 488.9 |
| "A147" | 5-{2,4-Dihydroxy-5-[N-(pyridin-3-ylmethyl)-N-methylaminosulfonyl]phenyl}-4-(2-fluorophenyl)-3-hydroxy-4H-1,2,4-triazole | 472.5 |
| "A148" | 5-{2,4-Dihydroxy-5-[N-(pyridin-4-ylmethyl)-N-methylaminosulfonyl]phenyl}-4-(2-methylphenyl)-3-hydroxy-4H-1,2,4-triazole | 468.5 |
| "A149" | 5-{2,4-Dihydroxy-5-[N-(pyridin-4-ylmethyl)-N-methylaminosulfonyl]phenyl}-4-(2-chlorophenyl)-3-hydroxy-4H-1,2,4-triazole | 488.9 |
| "A150" | 5-{2,4-Dihydroxy-5-[N-(pyridin-4-ylmethyl)-N-methylaminosulfonyl]phenyl}-4-(2-fluorophenyl)-3-hydroxy-4H-1,2,4-triazole | 472.5 |
| "A151" | 5-{2,4-Dihydroxy-5-[N-(1-oxypyridin-2-ylmethyl)-N-methylaminosulfonyl]phenyl}-4-(2-methylphenyl)-3-hydroxy-4H-1,2,4-triazole | 484.5 |
| "A152" | 5-{2,4-Dihydroxy-5-[N-(1-oxypyridin-2-ylmethyl)-N-methylaminosulfonyl]phenyl}-4-(2-chlorophenyl)-3-hydroxy-4H-1,2,4-triazole | 504.9 |
| "A153" | 5-{2,4-Dihydroxy-5-[N-(1-oxypyridin-2-ylmethyl)-N-methylaminosulfonyl]phenyl}-4-(2-fluorophenyl)-3-hydroxy-4H-1,2,4-triazole | 488.5 |
| "A154" | 5-{2,4-Dihydroxy-5-[N-(1-oxypyridin-3-ylmethyl)-N-methylaminosulfonyl]phenyl}-4-(2-methylphenyl)-3-hydroxy-4H-1,2,4-triazole | 484.5 |
| "A155" | 5-{2,4-Dihydroxy-5-[N-(1-oxypyridin-3-ylmethyl)-N-methylaminosulfonyl]phenyl}-4-(2-chlorophenyl)-3-hydroxy-4H-1,2,4-triazole | 504.9 |
| "A156" | 5-{2,4-Dihydroxy-5-[N-(1-oxypyridin-3-ylmethyl)-N-methylaminosulfonyl]phenyl}-4-(2-fluorophenyl)-3-hydroxy-4H-1,2,4-triazole | 488.5 |
| "A157" | 5-{2,4-Dihydroxy-5-[N-(1-oxypyridin-4-ylmethyl)-N-methylaminosulfonyl]phenyl}-4-(2-methylphenyl)-3-hydroxy-4H-1,2,4-triazole | 484.5 |
| "A158" | 5-{2,4-Dihydroxy-5-[N-(1-oxypyridin-4-ylmethyl)-N-methylaminosulfonyl]phenyl}-4-(2-chlorophenyl)-3-hydroxy-4H-1,2,4-triazole | 504.9 |
| "A159" | 5-{2,4-Dihydroxy-5-[N-(1-oxypyridin-4-ylmethyl)-N-methylaminosulfonyl]phenyl}-4-(2-fluorophenyl)-3-hydroxy-4H-1,2,4-triazole | 488.5 |
| "A160" | 5-{2,4-Dihydroxy-5-[N-(2-chloro-6-fluorobenzyl)-N-methylaminosulfonyl]phenyl}-4-(2-methylphenyl)-3-hydroxy-4H-1,2,4-triazole | 520.0 |
| "A161" | 5-{2,4-Dihydroxy-5-[N-(2-chloro-6-fluorobenzyl)-N-methylaminosulfonyl]phenyl}-4-(2-chlorophenyl)-3-hydroxy-4H-1,2,4-triazole | 540.4 |
| "A162" | 5-{2,4-Dihydroxy-5-[N-(2-chloro-6-fluorobenzyl)-N-methylaminosulfonyl]phenyl}-4-(2-fluorophenyl)-3-hydroxy-4H-1,2,4-triazole | 523.9 |
| "A163" | 5-{2,4-Dihydroxy-5-[N-(3-chloro-6-methoxybenzyl)-N-methylaminosulfonyl]phenyl}-4-(2-methylphenyl)-3-hydroxy-4H-1,2,4-triazole | 532.0 |

| | | |
|---|---|---|
| "A164" | 5-{2,4-Dihydroxy-5-[N-(3-chloro-6-methoxybenzyl)-N-methylaminosulfonyl]phenyl}-4-(2-chlorophenyl)-3-hydroxy-4H-1,2,4-triazole | 552.4 |
| "A165" | 5-{2,4-Dihydroxy-5-[N-(3-chloro-6-methoxybenzyl)-N-methylaminosulfonyl]phenyl}-4-(2-fluorophenyl)-3-hydroxy-4H-1,2,4-triazole | 535.9 |
| "A166" | 5-{2,4-Dihydroxy-5-[N-(3-fluoro-6-methoxybenzyl)-N-methylaminosulfonyl]phenyl}-4-(2-methylphenyl)-3-hydroxy-4H-1,2,4-triazole | 515.5 |
| "A167" | 5-{2,4-Dihydroxy-5-[N-(3-fluoro-6-methoxybenzyl)-N-methylaminosulfonyl]phenyl}-4-(2-chlorophenyl)-3-hydroxy-4H-1,2,4-triazole | 535.9 |
| "A168" | 5-{2,4-Dihydroxy-5-[N-(3-fluoro-6-methoxybenzyl)-N-methylaminosulfonyl]phenyl}-4-(2-fluorophenyl)-3-hydroxy-4H-1,2,4-triazole | 519.5 |
| "A169" | 5-{2,4-Dihydroxy-5-[N-(2,3-dimethoxybenzyl)-N-methylaminosulfonyl]phenyl}-4-(2-methylphenyl)-3-hydroxy-4H-1,2,4-triazole | 527.6 |
| "A170" | 5-{2,4-Dihydroxy-5-[N-(2,3-dimethoxybenzyl)-N-methylaminosulfonyl]phenyl}-4-(2-chlorophenyl)-3-hydroxy-4H-1,2,4-triazole | 548.0 |
| "A171" | 5-{2,4-Dihydroxy-5-[N-(2,3-dimethoxybenzyl)-N-methylaminosulfonyl]phenyl}-4-(2-fluorophenyl)-3-hydroxy-4H-1,2,4-triazole | 531.5 |
| "A172" | 5-{2,4-Dihydroxy-5-[N-(furan-2-ylmethyl)-N-methyl-aminosulfonyl]phenyl}-4-(2-methylphenyl)-3-hydroxy-4H-1,2,4-triazole | 457.5 |
| "A173" | 5-{2,4-Dihydroxy-5-[N-(furan-2-ylmethyl)-N-methyl-aminosulfonyl]phenyl}-4-(2-chlorophenyl)-3-hydroxy-4H-1,2,4-triazole | 477.9 |
| "A174" | 5-{2,4-Dihydroxy-5-[N-(furan-2-ylmethyl)-N-methyl-aminosulfonyl]phenyl}-4-(2-fluorophenyl)-3-hydroxy-4H-1,2,4-triazole | 461.4 |
| "A175" | 5-{2,4-Dihydroxy-5-[N-(furan-3-ylmethyl)-N-methyl-aminosulfonyl]phenyl}-4-(2-methylphenyl)-3-hydroxy-4H-1,2,4-triazole | 457.5 |
| "A176" | 5-{2,4-Dihydroxy-5-[N-(furan-3-ylmethyl)-N-methyl-aminosulfonyl]phenyl}-4-(2-chlorophenyl)-3-hydroxy-4H-1,2,4-triazole | 477.9 |
| "A177" | 5-{2,4-Dihydroxy-5-[N-(furan-3-ylmethyl)-N-methyl-aminosulfonyl]phenyl}-4-(2-fluorophenyl)-3-hydroxy-4H-1,2,4-triazole | 461.4 |
| "A178" | 5-(2,4-Dihydroxy-5-{N-[2-(2-dimethylaminoethoxy)-benzyl]-N-methylaminosulfonyl}phenyl)-4-(2-methylphenyl)-3-hydroxy-4H-1,2,4-triazole | 554.6 |
| "A179" | 5-(2,4-Dihydroxy-5-{N-[2-(2-dimethylaminoethoxy)-benzyl]-N-methylaminosulfonyl}phenyl)-4-(2-chlorophenyl)-3-hydroxy-4H-1,2,4-triazole | 575.1 |
| "A180" | 5-(2,4-Dihydroxy-5-{N-[2-(2-dimethylaminoethoxy)-benzyl]-N-methylaminosulfonyl}phenyl)-4-(2-fluorophenyl)-3-hydroxy-4H-1,2,4-triazole | 558.6 |
| "A181" | 5-(2,4-Dihydroxy-5-{N-[2-(2-methylaminoethoxy)-benzyl]-N-methylaminosulfonyl}phenyl)-4-(2-methylphenyl)-3-hydroxy-4H-1,2,4-triazole | 540.6 |
| "A182" | 5-(2,4-Dihydroxy-5-{N-[2-(2-methylaminoethoxy)-benzyl]-N-methylaminosulfonyl}phenyl)-4-(2-chlorophenyl)-3-hydroxy-4H-1,2,4-triazole | 561.0 |
| "A183" | 5-(2,4-Dihydroxy-5-{N-[2-(2-methylaminoethoxy)-benzyl]-N-methylaminosulfonyl}phenyl)-4-(2-fluorophenyl)-3-hydroxy-4H-1,2,4-triazole | 544.6 |
| "A184" | 5-(2,4-Dihydroxy-5-{N-[2-(2-aminoethoxy)benzyl]-N-methylaminosulfonyl}phenyl)-4-(2-methylphenyl)-3-hydroxy-4H-1,2,4-triazole | 526.6 |
| "A185" | 5-(2,4-Dihydroxy-5-{N-[2-(2-aminoethoxy)benzyl]-N-methylaminosulfonyl}phenyl)-4-(2-chlorophenyl)-3-hydroxy-4H-1,2,4-triazole | 547.0 |
| "A186" | 5-(2,4-Dihydroxy-5-{N-[2-(2-aminoethoxy)benzyl]-N-methylaminosulfonyl}phenyl)-4-(2-fluorophenyl)-3-hydroxy-4H-1,2,4-triazole | 530.5 |
| "A187" | 5-(2,4-Dihydroxy-5-{N-[2-(2-hydroxyethoxy)benzyl]-N-methylaminosulfonyl}phenyl)-4-(2-methylphenyl)-3-hydroxy-4H-1,2,4-triazole | 527.6 |
| "A188" | 5-(2,4-Dihydroxy-5-{N-[2-(2-hydroxyethoxy)benzyl]-N-methylaminosulfonyl}phenyl)-4-(2-chlorophenyl)-3-hydroxy-4H-1,2,4-triazole | 548.0 |
| "A189" | 5-(2,4-Dihydroxy-5-{N-[2-(2-hydroxyethoxy)benzyl]-N-methylaminosulfonyl}phenyl)-4-(2-fluorophenyl)-3-hydroxy-4H-1,2,4-triazole | 531.5 |
| "A190" | 5-(2,4-Dihydroxy-5-{N-[2-(2-isopropylaminoethoxy)-benzyl]-N-methylaminosulfonyl}phenyl)-4-(2-methylphenyl)-3-hydroxy-4H-1,2,4-triazole | 568.7 |
| "A191" | 5-(2,4-Dihydroxy-5-{N-[2-(2-isopropylaminoethoxy)-benzyl]-N-methylaminosulfonyl}phenyl)-4-(2-chlorophenyl)-3-hydroxy-4H-1,2,4-triazole | 589.1 |
| "A192" | 5-(2,4-Dihydroxy-5-{N-[2-(2-isopropylaminoethoxy)-benzyl]-N-methylaminosulfonyl}phenyl)-4-(2-fluorophenyl)-3-hydroxy-4H-1,2,4-triazole | 572.6 |
| "A193" | 5-(2,4-Dihydroxy-5-{N-[2-(carbamoylmethoxy)-benzyl]-N-methylaminosulfonyl}phenyl)-4-(2-methylphenyl)-3-hydroxy-4H-1,2,4-triazole | 540.6 |
| "A194" | 5-(2,4-Dihydroxy-5-{N-[2-(carbamoylmethoxy)-benzyl]-N-methylaminosulfonyl}phenyl)-4-(2-chlorophenyl)-3-hydroxy-4H-1,2,4-triazole | 561.0 |
| "A195" | 5-(2,4-Dihydroxy-5-{N-[2-(carbamoylmethoxy)-benzyl]-N-methylaminosulfonyl}phenyl)-4-(2-fluorophenyl)-3-hydroxy-4H-1,2,4-triazole | 544.5 |
| "A196" | 5-{2,4-Dihydroxy-5-[N-(1-methylpyrrol-2-ylmethyl)-N-methylaminosulfonyl]phenyl}-4-(2-methylphenyl)-3-hydroxy-4H-1,2,4-triazole | 470.5 |
| "A197" | 5-{2,4-Dihydroxy-5-[N-(1-methylpyrrol-2-ylmethyl)-N-methylaminosulfonyl]phenyl}-4-(2-chlorophenyl)-3-hydroxy-4H-1,2,4-triazole | 490.9 |
| "A198" | 5-{2,4-Dihydroxy-5-[N-(1-methylpyrrol-2-ylmethyl)-N-methylaminosulfonyl]phenyl}-4-(2-fluorophenyl)-3-hydroxy-4H-1,2,4-triazole | 474.5 |
| "A199" | 5-{2,4-Dihydroxy-5-[N-(isoxazol-3-ylmethyl)-N-methylaminosulfonyl]phenyl}-4-(2-methylphenyl)-3-hydroxy-4H-1,2,4-triazole | 458.5 |
| "A200" | 5-{2,4-Dihydroxy-5-[N-(isoxazol-3-ylmethyl)-N-methylaminosulfonyl]phenyl}-4-(2-chlorophenyl)-3-hydroxy-4H-1,2,4-triazole | 478.9 |
| "A201" | 5-{2,4-Dihydroxy-5-[N-(isoxazol-3-ylmethyl)-N-methylaminosulfonyl]phenyl}-4-(2-fluorophenyl)-3-hydroxy-4H-1,2,4-triazole | 462.4 |
| "A202" | 5-{2,4-Dihydroxy-5-[N-(pyridazin-3-ylmethyl)-N-methylaminosulfonyl]phenyl}-4-(2-methylphenyl)-3-hydroxy-4H-1,2,4-triazole | 469.5 |
| "A203" | 5-{2,4-Dihydroxy-5-[N-(pyridazin-3-ylmethyl)-N-methylaminosulfonyl]phenyl}-4-(2-chlorophenyl)-3-hydroxy-4H-1,2,4-triazole | 489.9 |
| "A204" | 5-{2,4-Dihydroxy-5-[N-(pyridazin-3-ylmethyl)-N-methylaminosulfonyl]phenyl}-4-(2-fluorophenyl)-3-hydroxy-4H-1,2,4-triazole | 473.3 |
| "A205" | 5-{2,4-Dihydroxy-5-[N-(pyrazin-2-ylmethyl)-N-methylaminosulfonyl]phenyl}-4-(2-methylphenyl)-3-hydroxy-4H-1,2,4-triazole | 469.5 |
| "A206" | 5-{2,4-Dihydroxy-5-[N-(pyrazin-2-ylmethyl)-N-methylaminosulfonyl]phenyl}-4-(2-chlorophenyl)-3-hydroxy-4H-1,2,4-triazole | 489.9 |
| "A207" | 5-{2,4-Dihydroxy-5-[N-(pyrazin-2-ylmethyl)-N-methylaminosulfonyl]phenyl}-4-(2-fluorophenyl)-3-hydroxy-4H-1,2,4-triazole | 473.5 |
| "A208" | 5-{2,4-Dihydroxy-5-[N-(2-carbamoyl-5-chlorobenzyl)-N-methylaminosulfonyl]phenyl}-4-(2-methylphenyl)-3-hydroxy-4H-1,2,4-triazole | 545.0 |
| "A209" | 5-{2,4-Dihydroxy-5-[N-(2-carbamoyl-5-chlorobenzyl)-N-methylaminosulfonyl]phenyl}-4-(2-chlorophenyl)-3-hydroxy-4H-1,2,4-triazole | 565.4 |
| "A210" | 5-{2,4-Dihydroxy-5-[N-(2-carbamoyl-5-chlorobenzyl)-N-methylaminosulfonyl]phenyl}-4-(2-fluorophenyl)-3-hydroxy-4H-1,2,4-triazole | 548.9 |
| "A211" | 5-(2,4-Dihydroxy-5-{N-[2-(2-methylaminoethoxy)-benzyl]-N-methylaminosulfonyl}phenyl)-4-(2-methylphenyl)-3-hydroxy-4H-1,2,4-triazole | 540.6 |
| "A212" | 5-(2,4-Dihydroxy-5-{N-[2-(2-methylaminoethoxy)-benzyl]-N-methylaminosulfonyl}phenyl)-4-(2-chlorophenyl)-3-hydroxy-4H-1,2,4-triazole | 561.0 |
| "A213" | 5-(2,4-Dihydroxy-5-{N-[2-(2-methylaminoethoxy)-benzyl]-N-methylaminosulfonyl}phenyl)-4-(2-fluorophenyl)-3-hydroxy-4H-1,2,4-triazole | 544.6 |
| "A214" | 5-{2,4-Dihydroxy-5-[N-(2,3-dimethoxybenzyl)-N-methylaminosulfonyl]phenyl}-4-(2-methylphenyl)-3-hydroxy-4H-1,2,4-triazole | 527.6 |
| "A215" | 5-{2,4-Dihydroxy-5-[N-(2,3-dimethoxybenzyl)-N-methylaminosulfonyl]phenyl}-4-(2-chlorophenyl)-3-hydroxy-4H-1,2,4-triazole | 548.0 |

| | | |
|---|---|---|
| "A216" | 5-{2,4-Dihydroxy-5-[N-(2,3-dimethoxybenzyl)-N-methylaminosulfonyl]phenyl}-4-(2-fluorophenyl)-3-hydroxy-4H-1,2,4-triazole | 531.5 |
| "A217" | 5-(2,4-Dihydroxy-5-{N-[2-(2-cyanoethoxy)benzyl]-N-methylaminosulfonyl}phenyl)-4-(2-methylphenyl)-3-hydroxy-4H-1,2,4-triazole | 536.6 |
| "A218" | 5-(2,4-Dihydroxy-5-{N-[2-(2-cyanoethoxy)benzyl]-N-methylaminosulfonyl}phenyl)-4-(2-chlorophenyl)-3-hydroxy-4H-1,2,4-triazole | 557.0 |
| "A219" | 5-(2,4-Dihydroxy-5-{N-[2-(2-cyanoethoxy)benzyl]-N-methylaminosulfonyl}phenyl)-4-(2-fluorophenyl)-3-hydroxy-4H-1,2,4-triazole | 540.5 |
| "A220" | 5-{2,4-Dihydroxy-5-[N-(4-fluorobenzyl)-N-methyl-aminosulfonyl]phenyl}-4-(2-methylaminomethylphenyl)-3-hydroxy-4H-1,2,4-triazole | 514.5 |
| "A221" | 5-{2,4-Dihydroxy-5-[N-(4-fluorobenzyl)-N-methyl-aminosulfonyl]phenyl}-4-(2-aminomethylphenyl)-3-hydroxy-4H-1,2,4-triazole | 500.5 |
| "A222" | 5-[2,4-Dihydroxy-5-(N-benzyl-N-methylamino-sulfonyl)phenyl]-4-(2-cyanophenyl)-3-hydroxy-4H-1,2,4-triazole | 478.5 |
| "A223" | 5-[2,4-Dihydroxy-5-(N-benzyl-N-methylamino-sulfonyl)phenyl]-4-(2-cyanophenyl)-3-hydroxy-4H-1,2,4-triazole | 481.5 |
| "A224" | 5-[2,4-Dihydroxy-5-(N-benzyl-N-methylamino-sulfonyl)phenyl]-4-{4-[2-(piperazin-4-yl)ethoxy]-phenyl}-3-hydroxy-4H-1,2,4-triazole | 581.7 |
| "A225" | 5-[2,4-Dihydroxy-5-(N-benzyl-N-methylamino-sulfonyl)phenyl]-4-phenyl-3-hydroxy-4H-1,2,4-triazole | 453.5 |
| "A226" | 5-[2,4-Dihydroxy-5-(N-benzyl-N-methylamino-sulfonyl)phenyl]-4-(2-methylphenyl)-3-hydroxy-4H-1,2,4-triazole | 467.5 |
| "A227" | 5-[2,4-Dihydroxy-5-(N-benzyl-N-methylamino-sulfonyl)phenyl]-4-(2-chlorophenyl)-3-hydroxy-4H-1,2,4-triazole | 487.9 |
| "A228" | 5-[2,4-Dihydroxy-5-(N-benzyl-N-methylamino-sulfonyl)phenyl]-4-(2-fluorophenyl)-3-hydroxy-4H-1,2,4-triazole | 471.5 |

The following examples relate to pharmaceutical compositions:

EXAMPLE A

Injection Vials

A solution of 100 g of an active ingredient according to the invention and g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of the formula I

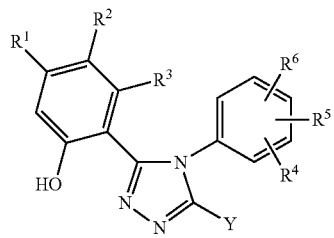

I in which
$R^1$ denotes OH, $OCH_3$, $OCF_3$, $OCHF_2$, OBzl, OAc, p-methoxybenzyloxy, SH, $S(O)_mCH_3$, $SO_2NH_2$, Hal, $CF_3$ or $CH_3$,
$R^2$ denotes $CONA[(CH_2)_oAr]$, $CONA[(CH_2)_oHet']$, $SO_2NA[(CH_2)_oAr']$ or $SO_2NA[(CH_2)_oHet']$, R³ denotes H, Hal, CN, NO₂, A, Alk, $(CH_2)_nAr$, $(CH_2)_nHet'$, COOH, COOA, COOAr, COOHet', CONH₂, CONHA, CONAA', CONHAr, CONAAr, $CON(Ar)_2$, CONHHet', $CON(Het')_2$, NH₂, NHA, NHAr, NHHet', NAA', NHCOA, NACOA', NHCOAr, NHCOHet', NHCOOA, NHCOOAr, NHCOOHet', NHCONHA, NHCONHAr, NHCONHHet', OH, OA, OAr, Het', SH, $S(O)_mA$, $S(O)_mAr$, $S(O)_mHet'$, SO₂NH₂, SO₂NHA, SO₂NAA', SO₂NHAr, SO₂NAAr, SO₂NHHet', SO₂NAHet', SO₂NA-benzyl, $SO_2N(Ar)_2$ or $SO_2N(Hd)_2$, R⁴, R⁵, R⁶ each, independently of one another, denote H, Hal, CN, NO₂, A, Alk, $(CH_2)_nAr$, $(CH_2)_nHet'$, COOH, COOA, COOAr, COOHet', CONH₂, CONHA, CONAA', CONHAr, CONAAr, $CON(Ar)_2$, CONHHet', $CON(Het')_2$, NH₂, NHA, NHAr, NHHet', NAA', NHCOA, NHCONH₂, NACOA', $NHCO(CH_2)_nAr$, NHCOHet', NHCOOA, NHCOOAr, NHCOOHet', NHCONHA, NHCONHAr, NHCONHHet', OH, OA, $O(CH_2)_oHet$, $O(CH_2)_oNH_2$, $O(CH_2)_oCN$, OAr, Het', SH, $S(O)_mA$, $S(O)_mAr$, $S(O)_mHet'$, SO₂NH₂, SO₂NHA, SO₂NAA', SO₂NHAr, SO₂NAAr, SO₂NHHet', $SO_2N(Ar)_2$ or $SO_2N(Hd)_2$, R⁴ and R⁵ together also denote OCH₂O, OCH₂CH₂O, —CH=CH—CH=CH—, NH—CH=CH or CH=CH—NH, Y denotes OH or SH, A, A' each, independently of one another, denote unbranched or branched alkyl having 1-10 C atoms, in which one, two or three CH₂ groups may be replaced by O, S, SO, SO₂, NH, NR⁸ and/or by —CH=CH— groups and/or in addition 1-5H atoms may be replaced by F, Cl, Br and/or R⁷, Alk or cyclic alkyl having 3-7 C atoms, A and A' together also denote an alkylene chain having 2, 3, 4, 5 or 6 C atoms, in which a CH₂ group may be replaced by O, S, SO, SO₂, N, NH, NR⁸, NCOR⁸ or NCOOR⁸, Alk denotes alkenyl having 2-6 C atoms, R⁷ denotes CN, COOR⁹, CONR⁹R¹⁰, NR⁹R¹⁰, NHCOR⁹, NHCOOR⁹ or OR⁹, R⁸ denotes cycloalkyl having 3-7 C atoms,
cycloalkylalkylene having 4-10 C atoms,
Alk or
unbranched or branched alkyl having 1-6 C atoms, in which one, two or three CH₂ groups may be replaced by O, S, SO, SO₂, NH and/or in addition 1-5H atoms may be replaced by F and/or Cl, R⁹, R¹⁰ each, independently of one another, denote H or alkyl having 1-5 C atoms, in which 1-3 CH₂ groups may be replaced by O, S, SO, SO₂, NH, NMe or NEt and/or in addition 1-5H atoms may be replaced by F and/or Cl, R⁹ and R¹⁰ together also denote an alkylene chain having 2, 3, 4, 5 or 6 C atoms, in which a CH₂ group may be replaced by O, S, SO, SO₂, NH, NR⁸, NCOR⁸ or NCOOR⁸, Ar denotes phenyl, naphthyl or biphenyl, each of which is unsubstituted or mono-, di- or trisubstituted by Hal, A, XR⁷, Y, CN, phenyl, Het", OXHet''', OA, OXR⁷, $S(O)_mA$, $S(O)_mXR^7$, NO₂, NH₂, NR⁹R¹⁰, NR⁸R⁹, CONR⁹R¹⁰, CONR⁸R⁹, SO₂NR⁹R¹⁰, SO₂NR⁸R⁹, NR⁹COR¹⁰, NR⁹CONR⁹R¹⁰ and/or NR⁹SO₂R¹⁰, Ar' denotes phenyl, naphthyl or biphenyl, each of which is mono-, di- or trisubstituted by Hal, A, XR⁷, XR⁴, Y, CN, Ar, Het, OA, OXR⁷, OXR⁴, $S(O)_mA$, $S(O)_mXR^7$, $S(O)_mXR^4$, NO₂, NH₂, NR⁹R¹⁰, NR⁸R⁹, CONR⁹R¹⁰, CONR⁸R⁹, SO₂NR⁹R¹⁰, SO₂NR⁸R⁹, NR⁹COR¹⁰, NR⁹CONR⁹R¹⁰ and/or NR⁹SO₂R¹⁰, Het denotes a mono- or bicyclic saturated, unsaturated or aromatic heterocycle having 1 to 4 N, O and/or S atoms, which may be unsubstituted or mono-, di- or trisubstituted by Hal, A, XR⁷, Y, CN, Ar, OA, OXR⁷, $S(O)_mA$, $S(O)_mXR^7$, NO₂, NH₂, NR⁹R¹⁰, NR⁸R⁹, CONR⁹R¹⁰, CONR⁸R⁹, SO₂NR⁹R¹⁰, SO₂NR⁸R⁹, NR⁹COR¹⁰, NR⁹CONR⁹R¹⁰, NR⁹SO₂R¹⁰, =S, =NR¹¹, =NR¹¹R⁷ and/or =O (carbonyl oxygen), Het' denotes a mono- or bicyclic saturated, unsaturated or aromatic heterocycle having 1 to 4 N, O and/or S atoms, which may be unsubstituted or mono-, di- or trisubstituted by Hal, A, XR⁷, XR⁴, Y, CN, Ar, Het, OA, OXR⁷, OXR⁴, $S(O)_mA$, $S(O)_mXR^7$, $S(O)_mXR^4$, NO₂, NH₂, NR⁹R¹⁰, NR⁸R⁹, CONR⁹R¹⁰, CONR⁸R⁹, SO₂NR⁹R¹⁰, SO₂NR⁸R⁹, NR⁹COR¹⁰, NR⁹CONR⁹R¹⁰, NR⁹SO₂R¹⁰, =S, =NR¹¹, =NR¹¹R⁷ and/or =O (carbonyl oxygen), and/or in which a ring nitrogen may be substituted by —O⁻, Het" denotes a monocyclic aromatic heterocycle having 1 to 3 N, O and/or S atoms, Het''' denotes a monocyclic saturated heterocycle having 1 to 3 N, O and/or S atoms, X denotes unbranched or branched alkylene having 1-10 C atoms, in which one, two or three CH₂ groups may be replaced by O, S, SO, SO₂, NH, NR⁸ and/or by —CH=CH— groups and/or in addition 1-5H atoms may be replaced by F, Cl, Br and/or R⁷, R¹¹ denotes H or A, Hal denotes F, Cl, Br or I, m denotes 0, 1 or 2, n denotes 0, 1, 2, 3 or 4, o denotes 1, 2 or 3, or pharmaceutically usable salts, tautomers or stereoisomers thereof, including mixtures thereof in all ratios.

2. The compound of formula I according to claim 1 in which

R¹ denotes OH or OCH₃, or pharmaceutically usable salts, tautomers or stereoisomers thereof, including mixtures thereof in all ratios.

3. The compound according to claim 1 in which

R³ denotes H, or pharmaceutically usable salts, tautomers or stereoisomers thereof, including mixtures thereof in all ratios.

4. The compound according to claim 1 in which

R² denotes $CONA[(CH_2)_oAr]$, $CONA[(CH_2)_oHet']$, $SO_2NA[(CH_2)_oAr']$ or $SO_2NA[(CH_2)_oHet']$, where A denotes alkyl having 1, 2, 3 or 4 C atoms, or pharmaceutically usable salts, tautomers or stereoisomers thereof, including mixtures thereof in all ratios.

5. The compound according to claim 1 in which

R² denotes $CON(CH_3)CH_2Ar$, $CON(CH_3)CH_2Het'$, $SO_2N(CH_3)CH_2Ar'$ or $SO_2N(CH_3)CH_2Het'$, or pharmaceutically usable salts, tautomers or stereoisomers thereof, including mixtures thereof in all ratios.

6. The compound according to claim 1 in which

R⁴, R⁵, R⁶ each, independently of one another, denote H, Hal, CN, A, $O(CH_2)_oHet'$, $O(CH_2)_oCN$, $(CH_2)_oNH_2$, $(CH_2)_oNHA$ or $(CH_2)_oNAA'$, or pharmaceutically usable salts, tautomers or stereoisomers thereof, including mixtures thereof in all ratios.

7. The compound according to claim 1 in which

R⁴, R⁵ denote H,

R⁶ denotes H, Hal, CN, A, $O(CH_2)_oHet'$, $O(CH_2)_oCN$, $(CH_2)_oNH_2$, $(CH_2)_oNHA$ or $(CH_2)_oNAA'$, or pharmaceutically usable salts, tautomers or stereoisomers thereof, including mixtures thereof in all ratios.

8. The compound according to claim 1 in which

X denotes alkylene having 1-6 C atoms, in which one, two or three $CH_2$ groups may be replaced by O, NH, and/or 1-5H atoms may be replaced by F and/or Cl, or pharmaceutically usable salts, tautomers or stereoisomers thereof, including mixtures thereof in all ratios.

9. The compound according to claim 1 in which

X denotes alkylene having 1, 2, 3 or 4 C atoms, or pharmaceutically usable salts, tautomers or stereoisomers thereof, including mixtures thereof in all ratios.

10. The compound according to claim 1 in which

Ar denotes phenyl which is unsubstituted or mono-, di- or trisubstituted by Hal, A, $XR^7$, phenyl, Het'', OXHet''', OA, $OXR^7$ and/or $CONR^9R^{10}$, or pharmaceutically usable salts, tautomers or stereoisomers thereof, including mixtures thereof in all ratios.

11. The compound according to claim 1 in which

Ar' denotes phenyl which is mono-, di- or trisubstituted by Hal, A, $XR^7$, OA, $OXR^7$ and/or $CONR^9R^{10}$, or pharmaceutically usable salts, tautomers or stereoisomers thereof, including mixtures thereof in all ratios.

12. The compound according to claim 1 in which $R^7$ denotes CN, $CONR^9R^{10}$, $NR^9R^{10}$ or $OR^9$, or pharmaceutically usable salts, tautomers or stereoisomers thereof, including mixtures thereof in all ratios.

13. The compound according to claim 1 in which

Het' denotes a mono- or bicyclic saturated, unsaturated or aromatic heterocycle having 1 to 3 N, O and/or S atoms, which may be unsubstituted or mono-, di- or trisubstituted by A, Hal, OH and/or OA and/or in which a ring nitrogen may be substituted by $—O^-$, or pharmaceutically usable salts, tautomers or stereoisomers thereof, including mixtures thereof in all ratios.

14. The compound according to claim 1 in which

Het' denotes pyridyl, N-oxypyridyl, furyl, thienyl, pyrrolyl, oxazolyl, isoxazolyl, imidazolyl, pyrimidinyl, pyrazolyl, thiazolyl, pyrazinyl, pyridazinyl, pyrrolidinyl, piperidinyl, morpholinyl, piperazinyl, benzodioxanyl, benzodioxolyl, indolyl, quinolinyl, benzimidazolyl, benzothiadiazolyl or indazolyl, each of which is unsubstituted or mono-, di- or trisubstituted by A, Hal, OH and/or OA, or pharmaceutically usable salts, tautomers or stereoisomers thereof, including mixtures thereof in all ratios.

15. The compound according to claim 1 in which

A denotes unbranched or branched alkyl having 1-6 C atoms, in which one, two or three $CH_2$ groups may be replaced by O, S, SO, $SO_2$, NH and/or by $—CH=CH—$ groups and/or in addition 1-5 H atoms may be replaced by F, Cl and/or Br, Alk or cyclic alkyl having 3-7 C atoms, or pharmaceutically usable salts, tautomers or stereoisomers thereof, including mixtures thereof in all ratios.

16. The compound according to claim 1 in which $R^9$, $R^{10}$ each, independently of one another, denote H or alkyl having 1-5 C atoms, in which 1-5H atoms may be replaced by F and/or Cl, or pharmaceutically usable salts, tautomers or stereoisomers thereof, including mixtures thereof in all ratios.

17. The compound according to claim 1 in which

A denotes unbranched or branched alkyl having 1-6 C atoms, in which 1-5H atoms may be replaced by F, Cl and/or Br, or cyclic alkyl having 3-7 C atoms, or pharmaceutically usable salts, tautomers or stereoisomers thereof, including mixtures thereof in all ratios.

18. The compound according to claim 1 in which $R^1$ denotes OH or $OCH_3$, $R^2$ denotes $CONA[(CH_2)_oAr]$, $CONA[(CH_2)_oHet']$, $SO_2NA[(CH_2)_oAr']$ or $SO_2NA[(CH_2)_oHet']$, where A denotes alkyl having 1, 2, 3 or 4 C atoms, $R^3$ denotes H, $R^4$, $R^5$, $R^6$ each, independently of one another, denote H, Hal, CN, A, $O(CH_2)_oHet'$, $O(CH_2)_oCN$, $(CH_2)_oNH_2$, $(CH_2)_oNHA$ or $(CH_2)_oNAA'$, X denotes alkylene having 1-6 C atoms, in which one, two or three $CH_2$ groups may be replaced by O, NH, and/or 1-5H atoms may be replaced by F, and/or Cl, Ar denotes phenyl which is unsubstituted or mono-, di- or trisubstituted by Hal, A, $XR^7$, phenyl, Het'', OXHet''', OA, $OXR^7$ and/or $CONR^9R^{10}$, Ar' denotes phenyl which is mono-, di- or trisubstituted by Hal, A, $XR^7$, OA, $OXR^7$ and/or $CONR^9R^{10}$, $R^7$ denotes CN, $CONR^9R^{10}$, $NR^9R^{10}$ or $OR^9$, Het' denotes a mono- or bicyclic saturated, unsaturated or aromatic heterocycle having 1 to 3 N, O and/or S atoms, which may be unsubstituted or mono-, di- or trisubstituted by A, Hal, OH and/or OA and/or in which a ring nitrogen may be substituted by—$O^-$, A denotes unbranched or branched alkyl having 1-6 C atoms, in which one, two or three $CH_2$ groups may be replaced by O, S, SO, $SO_2$, NH and/or by —CH=CH— groups and/or in addition 1-5 H atoms may be replaced by F, Cl and/or Br, Alk or cyclic alkyl having 3-7 C atoms, $R^9$, $R^{10}$ each, independently of one another, denote H or alkyl having 1-5 C atoms, in which 1-5H atoms may be replaced by F and/or Cl, or pharmaceutically usable salts, tautomers or stereoisomers thereof, including mixtures thereof in all ratios.

19. The compound according to claim 1 in which $R^1$ denotes OH or $OCH_3$, $R^2$ denotes $CON(CH_3)CH_2Ar$, $CON(CH_3)CH_2Het'$, $SO_2N(CH_3)CH_2Ar'$ or $SO_2N(CH_3)CH_2Het'$, $R^3$ denotes H, $R^4$, $R^5$ denote H, $R^6$ denotes H, Hal, CN, A, $O(CH_2)_oHet'$, $O(CH_2)_oCN$, $(CH_2)_oNH_2$, $(CH_2)_oNHA$ or $(CH_2)_oNAA'$, X denotes alkylene having 1, 2, 3 or 4 C atoms, Ar denotes phenyl which is unsubstituted or mono-, di- or trisubstituted by Hal, A, $XR^7$, phenyl, Het'', OXHet''', OA, $OXR^7$ and/or $CONR^9R^{10}$, Ar' denotes phenyl which is mono-, di- or trisubstituted by Hal, A, $XR^7$, OA, $OXR^7$ and/or $CONR^9R^{10}$, $R^7$ denotes CN, $CONR^9R^{10}$, $NR^9R^{10}$ or $OR^9$, Het' denotes pyridyl, N-oxypyridyl, furyl, thienyl, pyrrolyl, oxazolyl, isoxazolyl, imidazolyl, pyrimidinyl, pyrazolyl, thiazolyl, pyrazinyl, pyridazinyl, pyrrolidinyl, piperidinyl, morpholinyl, piperazinyl, benzodioxanyl, benzodioxolyl, indolyl, quinolinyl, benzimidazolyl, benzothiadiazolyl or indazolyl, each of which is unsubstituted or mono-, di- or trisubstituted by A, Hal, OH and/or OA, A denotes unbranched or branched alkyl having 1-6 C atoms, in which 1-5H atoms may be replaced by F, Cl and/or Br, or cyclic alkyl having 3-7 C atoms, $R^9$, $R^{10}$ each, independently of one another, denote H or alkyl having 1-5 C atoms, in which 1-5H atoms may be replaced by F and/or Cl, or pharmaceutically usable salts, tautomers or stereoisomers thereof, including mixtures thereof in all ratios.

20. The compound according to claim 1, of the formula

| Compound No. | Name and/or structure |
|---|---|
| "A1" | 5-[2,4-Dihydroxy-5-(N-benzyl-N-methylaminocarbonyl)phenyl]-4-(2-methylphenyl)-3-hydroxy-4H-1,2,4-triazole |
| "A2" | *(structure)* |
| "A3" | 5-[2,4-Dihydroxy-5-(N-benzyl-N-methylaminocarbonyl)phenyl]-4-phenyl-3-hydroxy-4H-1,2,4-triazole |
| | *(structure)* |
| "A4" | 5-[2,4-Dihydroxy-5-(N-benzyl-N-methylaminocarbonyl)phenyl]-4-(2-chlorophenyl)-3-hydroxy-4H-1,2,4-triazole |
| | *(structure)* |
| "A5" | 5-[2,4-Dihydroxy-5-(N-benzyl-N-methylaminocarbonyl)phenyl]-4-(2-fluorophenyl)-3-hydroxy-4H-1,2,4-triazole |
| "A6" | 5-{2,4-Dihydroxy-5-[N-(2-methoxybenzyl)-N-methyl-aminocarbonyl]phenyl}-4-(2-methylphenyl)-3-hydroxy-4H-1,2,4-triazole |
| | *(structure)* |
| "A6a" | 5-{2,4-Dihydroxy-5-[N-(3-methoxybenzyl)-N-methyl-aminocarbonyl]phenyl}-4-(2-methylphenyl)-3-hydroxy-4H-1,2,4-triazole |
| "A6b" | 5-{2,4-Dihydroxy-5-[N-(4-methoxybenzyl)-N-methyl-aminocarbonyl]phenyl}-4-(2-methylphenyl)-3-hydroxy-4H-1,2,4-triazole |
| "A7" | 5-{2,4-Dihydroxy-5-[N-(2-methoxybenzyl)-N-methyl-aminocarbonyl]phenyl}-4-(2-chlorophenyl)-3-hydroxy-4H-1,2,4-triazole |
| "A8" | 5-{2,4-Dihydroxy-5-[N-(2-methoxybenzyl)-N-methyl-aminocarbonyl]phenyl}-4-(2-fluorophenyl)-3-hydroxy-4H-1,2,4-triazole |
| "A9" | 5-{2,4-Dihydroxy-5-[N-(2-fluorobenzyl)-N-methyl-aminocarbonyl]phenyl}-4-(2-methylphenyl)-3-hydroxy-4H-1,2,4-triazole |
| "A10" | 5-{2,4-Dihydroxy-5-[N-(2-fluorobenzyl)-N-methyl-aminocarbonyl]phenyl}-4-(2-chlorophenyl)-3-hydroxy-4H-1,2,4-triazole |
| "A11" | 5-{2,4-Dihydroxy-5-[N-(2-fluorobenzyl)-N-methyl-aminocarbonyl]phenyl}-4-(2-fluorophenyl)-3-hydroxy-4H-1,2,4-triazole |
| "A12" | 5-{2,4-Dihydroxy-5-[N-(4-fluorobenzyl)-N-methyl-aminocarbonyl]phenyl}-4-(2-methylphenyl)-3-hydroxy-4H-1,2,4-triazole |
| "A13" | 5-{2,4-Dihydroxy-5-[N-(4-fluorobenzyl)-N-methyl-aminocarbonyl]phenyl}-4-(2-chlorophenyl)-3-hydroxy-4H-1,2,4-triazole |
| "A14" | 5-{2,4-Dihydroxy-5-[N-(4-fluorobenzyl)-N-methyl-aminocarbonyl]phenyl}-4-(2-fluorophenyl)-3-hydroxy-4H-1,2,4-triazole |
| "A15" | 5-{2,4-Dihydroxy-5-[N-(3-fluorobenzyl)-N-methyl-aminocarbonyl]phenyl}-4-(2-methylphenyl)-3-hydroxy-4H-1,2,4-triazole |
| "A16" | 5-{2,4-Dihydroxy-5-[N-(3-fluorobenzyl)-N-methyl-aminocarbonyl]phenyl}-4-(2-chlorophenyl)-3-hydroxy-4H-1,2,4-triazole |
| "A17" | 5-{2,4-Dihydroxy-5-[N-(3-fluorobenzyl)-N-methyl-aminocarbonyl]phenyl}-4-(2-fluorophenyl)-3-hydroxy-4H-1,2,4-triazole |
| "A18" | 5-{2,4-Dihydroxy-5-[N-(3-methylbenzyl)-N-methyl-aminocarbonyl]phenyl}-4-(2-methylphenyl)-3-hydroxy-4H-1,2,4-triazole |
| "A18a" | 5-{2,4-Dihydroxy-5-[N-(2-methylbenzyl)-N-methyl-aminocarbonyl]phenyl}-4-(2-methylphenyl)-3-hydroxy-4H-1,2,4-triazole |
| "A19" | 5-{2,4-Dihydroxy-5-[N-(3-methylbenzyl)-N-methyl-aminocarbonyl]phenyl}-4-(2-chlorophenyl)-3-hydroxy-4H-1,2,4-triazole |
| "A20" | 5-{2,4-Dihydroxy-5-[N-(3-methylbenzyl)-N-methyl-aminocarbonyl]phenyl}-4-(2-fluorophenyl)-3-hydroxy-4H-1,2,4-triazole |
| "A21" | 5-{2,4-Dihydroxy-5-[N-(4-methylbenzyl)-N-methyl-aminocarbonyl]phenyl}-4-(2-methylphenyl)-3-hydroxy-4H-1,2,4-triazole |
| "A22" | 5-{2,4-Dihydroxy-5-[N-(4-methylbenzyl)-N-methyl-aminocarbonyl]phenyl}-4-(2-chlorophenyl)-3-hydroxy-4H-1,2,4-triazole |
| "A23" | 5-{2,4-Dihydroxy-5-[N-(4-methylbenzyl)-N-methyl-aminocarbonyl]phenyl}-4-(2-fluorophenyl)-3-hydroxy-4H-1,2,4-triazole |
| "A24" | 5-{2,4-Dihydroxy-5-[N-(3-chlorobenzyl)-N-methyl-aminocarbonyl]phenyl}-4-(2-methylphenyl)-3-hydroxy-4H-1,2,4-triazole |
| "A25" | 5-{2,4-Dihydroxy-5-[N-(3-chlorobenzyl)-N-methyl-aminocarbonyl]phenyl}-4-(2-chlorophenyl)-3-hydroxy-4H-1,2,4-triazole |
| "A26" | 5-{2,4-Dihydroxy-5-[N-(3-chlorobenzyl)-N-methyl-aminocarbonyl]phenyl}-4-(2-fluorophenyl)-3-hydroxy-4H-1,2,4-triazole |
| "A27" | 5-{2,4-Dihydroxy-5-[N-(2-chlorobenzyl)-N-methyl-aminocarbonyl]phenyl}-4-(2-methylphenyl)-3-hydroxy-4H-1,2,4-triazole |
| "A28" | 5-{2,4-Dihydroxy-5-[N-(2-chlorobenzyl)-N-methyl-aminocarbonyl]phenyl}-4-(2-chlorophenyl)-3-hydroxy-4H-1,2,4-triazole |

| Compound No. | Name and/or structure |
|---|---|
| "A29" | 5-{2,4-Dihydroxy-5-[N-(2-chlorobenzyl)-N-methyl-aminocarbonyl]phenyl}-4-(2-fluorophenyl)-3-hydroxy-4H-1,2,4-triazole |
| "A30" | 5-{2,4-Dihydroxy-5-[N-(pyridin-2-ylmethyl)-N-methyl-aminocarbonyl]phenyl}-4-(2-methylphenyl)-3-hydroxy-4H-1,2,4-triazole <chemical structure> |
| "A31" | 5-{2,4-Dihydroxy-5-[N-(pyridin-2-ylmethyl)-N-methyl-aminocarbonyl]phenyl}-4-(2-chlorophenyl)-3-hydroxy-4H-1,2,4-triazole |
| "A32" | 5-{2,4-Dihydroxy-5-[N-(pyridin-2-ylmethyl)-N-methyl-aminocarbonyl]phenyl}-4-(2-fluorophenyl)-3-hydroxy-4H-1,2,4-triazole |
| "A33" | 5-{2,4-Dihydroxy-5-[N-(pyridin-3-ylmethyl)-N-methyl-aminocarbonyl]phenyl}-4-(2-methylphenyl)-3-hydroxy-4H-1,2,4-triazole |
| "A34" | 5-{2,4-Dihydroxy-5-[N-(pyridin-3-ylmethyl)-N-methyl-aminocarbonyl]phenyl}-4-(2-chlorophenyl)-3-hydroxy-4H-1,2,4-triazole |
| "A35" | 5-{2,4-Dihydroxy-5-[N-(pyridin-3-ylmethyl)-N-methyl-aminocarbonyl]phenyl}-4-(2-fluorophenyl)-3-hydroxy-4H-1,2,4-triazole |
| "A36" | 5-{2,4-Dihydroxy-5-[N-(pyridin-4-ylmethyl)-N-methyl-aminocarbonyl]phenyl}-4-(2-methylphenyl)-3-hydroxy-4H-1,2,4-triazole |
| "A37" | 5-{2,4-Dihydroxy-5-[N-(pyridin-4-ylmethyl)-N-methyl-aminocarbonyl]phenyl}-4-(2-chlorophenyl)-3-hydroxy-4H-1,2,4-triazole |
| "A38" | 5-{2,4-Dihydroxy-5-[N-(pyridin-4-ylmethyl)-N-methyl-aminocarbonyl]phenyl}-4-(2-fluorophenyl)-3-hydroxy-4H-1,2,4-triazole |
| "A39" | 5-{2,4-Dihydroxy-5-[N-(1-oxypyridin-2-ylmethyl)-N-methyl-aminocarbonyl]phenyl}-4-(2-methylphenyl)-3-hydroxy-4H-1,2,4-triazole <chemical structure> |
| "A40" | 5-{2,4-Dihydroxy-5-[N-(1-oxypyridin-2-ylmethyl)-N-methyl-aminocarbonyl]phenyl}-4-(2-chlorophenyl)-3-hydroxy-4H-1,2,4-triazole |
| "A41" | 5-{2,4-Dihydroxy-5-[N-(1-oxypyridin-2-ylmethyl)-N-methyl-aminocarbonyl]phenyl}-4-(2-fluorophenyl)-3-hydroxy-4H-1,2,4-triazole |
| "A42" | 5-{2,4-Dihydroxy-5-[N-(1-oxypyridin-3-ylmethyl)-N-methyl-aminocarbonyl]phenyl}-4-(2-methylphenyl)-3-hydroxy-4H-1,2,4-triazole |
| "A43" | 5-{2,4-Dihydroxy-5-[N-(1-oxypyridin-3-ylmethyl)-N-methyl-aminocarbonyl]phenyl}-4-(2-chlorophenyl)-3-hydroxy-4H-1,2,4-triazole |
| "A44" | 5-{2,4-Dihydroxy-5-[N-(1-oxypyridin-3-ylmethyl)-N-methyl-aminocarbonyl]phenyl}-4-(2-fluorophenyl)-3-hydroxy-4H-1,2,4-triazole |
| "A45" | 5-{2,4-Dihydroxy-5-[N-(1-oxypyridin-4-ylmethyl)-N-methyl-aminocarbonyl]phenyl}-4-(2-methylphenyl)-3-hydroxy-4H-1,2,4-triazole |
| "A46" | 5-{2,4-Dihydroxy-5-[N-(1-oxypyridin-4-ylmethyl)-N-methyl-aminocarbonyl]phenyl}-4-(2-chlorophenyl)-3-hydroxy-4H-1,2,4-triazole |
| "A47" | 5-{2,4-Dihydroxy-5-[N-(1-oxypyridin-4-ylmethyl)-N-methyl-aminocarbonyl]phenyl}-4-(2-fluorophenyl)-3-hydroxy-4H-1,2,4-triazole |
| "A48" | 5-{2,4-Dihydroxy-5-[N-(2-chloro-6-fluorobenzyl)-N-methyl-aminocarbonyl]phenyl}-4-(2-methylphenyl)-3-hydroxy-4H-1,2,4-triazole |
| "A49" | 5-{2,4-Dihydroxy-5-[N-(2-chloro-6-fluorobenzyl)-N-methyl-aminocarbonyl]phenyl}-4-(2-chlorophenyl)-3-hydroxy-4H-1,2,4-triazole |
| "A50" | 5-{2,4-Dihydroxy-5-[N-(2-chloro-6-fluorobenzyl)-N-methyl-aminocarbonyl]phenyl}-4-(2-fluorophenyl)-3-hydroxy-4H-1,2,4-triazole |
| "A51" | 5-{2,4-Dihydroxy-5-[N-(3-chloro-6-methoxybenzyl)-N-methyl-aminocarbonyl]phenyl}-4-(2-methylphenyl)-3-hydroxy-4H-1,2,4-triazole |
| "A52" | 5-{2,4-Dihydroxy-5-[N-(3-chloro-6-methoxybenzyl)-N-methyl-aminocarbonyl]phenyl}-4-(2-chlorophenyl)-3-hydroxy-4H-1,2,4-triazole |
| "A53" | 5-{2,4-Dihydroxy-5-[N-(3-chloro-6-methoxybenzyl)-N-methyl-aminocarbonyl]phenyl}-4-(2-fluorophenyl)-3-hydroxy-4H-1,2,4-triazole |
| "A54" | 5-{2,4-Dihydroxy-5-[N-(3-fluoro-6-methoxybenzyl)-N-methyl-aminocarbonyl]phenyl}-4-(2-methylphenyl)-3-hydroxy-4H-1,2,4-triazole |
| "A55" | 5-{2,4-Dihydroxy-5-[N-(3-fluoro-6-methoxybenzyl)-N-methyl-aminocarbonyl]phenyl}-4-(2-chlorophenyl)-3-hydroxy-4H-1,2,4-triazole |
| "A56" | 5-{2,4-Dihydroxy-5-[N-(3-fluoro-6-methoxybenzyl)-N-methyl-aminocarbonyl]phenyl}-4-(2-fluorophenyl)-3-hydroxy-4H-1,2,4-triazole |
| "A57" | 5-{2,4-Dihydroxy-5-[N-(furan-2-ylmethyl)-N-methyl-aminocarbonyl]phenyl}-4-(2-methylphenyl)-3-hydroxy-4H-1,2,4-triazole |
| "A57a" | 5-{2,4-Dihydroxy-5-[N-(furan-2-ylmethyl)-N-methyl-aminocarbonyl]phenyl}-4-phenyl-3-hydroxy-4H-1,2,4-triazole |
| "A57b" | 5-{2,4-Dihydroxy-5-[N-(furan-2-ylmethyl)-N-methyl-aminocarbonyl]phenyl}-4-(3-methylphenyl)-3-hydroxy-4H-1,2,4-triazole |
| "A58" | 5-{2,4-Dihydroxy-5-[N-(furan-2-ylmethyl)-N-methyl-aminocarbonyl]phenyl}-4-(2-chlorophenyl)-3-hydroxy-4H-1,2,4-triazole |
| "A58a" | 5-{2,4-Dihydroxy-5-[N-(furan-2-ylmethyl)-N-methyl-aminocarbonyl]phenyl}-4-(3-chlorophenyl)-3-hydroxy-4H-1,2,4-triazole |
| "A58b" | 5-{2,4-Dihydroxy-5-[N-(furan-2-ylmethyl)-N-methyl-aminocarbonyl]phenyl}-4-(3,5-dichlorophenyl)-3-hydroxy-4H-1,2,4-triazole |
| "A58c" | 5-{2,4-Dihydroxy-5-[N-(furan-2-ylmethyl)-N-methyl-aminocarbonyl]phenyl}-4-(4-chlorophenyl)-3-hydroxy-4H-1,2,4-triazole |
| "A59" | 5-{2,4-Dihydroxy-5-[N-(furan-2-ylmethyl)-N-methyl-aminocarbonyl]phenyl}-4-(2-fluorophenyl)-3-hydroxy-4H-1,2,4-triazole |
| "A59a" | 5-{2,4-Dihydroxy-5-[N-(furan-2-ylmethyl)-N-methyl-aminocarbonyl]phenyl}-4-(3-fluorophenyl)-3-hydroxy-4H-1,2,4-triazole |
| "A59b" | 5-{2,4-Dihydroxy-5-[N-(furan-2-ylmethyl)-N-methyl-aminocarbonyl]phenyl}-4-(3-ethylphenyl)-3-hydroxy-4H-1,2,4-triazole |
| "A60" | 5-{2,4-Dihydroxy-5-[N-(furan-3-ylmethyl)-N-methyl-aminocarbonyl]phenyl}-4-(2-methylphenyl)-3-hydroxy-4H-1,2,4-triazole |
| "A61" | 5-{2,4-Dihydroxy-5-[N-(furan-3-ylmethyl)-N-methyl-aminocarbonyl]phenyl}-4-(2-chlorophenyl)-3-hydroxy-4H-1,2,4-triazole |

-continued

| Compound No. | Name and/or structure |
|---|---|
| "A62" | 5-{2,4-Dihydroxy-5-[N-(furan-3-ylmethyl)-N-methyl-aminocarbonyl]phenyl}-4-(2-fluorophenyl)-3-hydroxy-4H-1,2,4-triazole |
| "A62a" | 5-{2,4-Dihydroxy-5-[N-(thiophen-2-ylmethyl)-N-methyl-aminocarbonyl]phenyl}-4-(2-methylphenyl)-3-hydroxy-4H-1,2,4-triazole |
| "A62b" | 5-{2,4-Dihydroxy-5-[N-(furan-2-ylmethyl)-N-methyl-aminocarbonyl]phenyl}-4-(3-methoxyphenyl)-3-hydroxy-4H-1,2,4-triazole |
| "A62c" | 5-{2,4-Dihydroxy-5-[N-(furan-2-ylmethyl)-N-methyl-aminocarbonyl]phenyl}-4-(2-ethylphenyl)-3-hydroxy-4H-1,2,4-triazole |
| "A63" | |
| "A64" | |
| "A65" | |
| "A66" | |
| "A67" | |
| "A68" | |
| "A69" | 5-{2,4-Dihydroxy-5-[N-(2-aminoethoxybenzyl)-N-methyl-aminocarbonyl]phenyl}-4-(2-methylphenyl)-3-hydroxy-4H-1,2,4-triazole |
| "A70" | 5-{2,4-Dihydroxy-5-[N-(2-aminoethoxybenzyl)-N-methyl-aminocarbonyl]phenyl}-4-(2-chlorophenyl)-3-hydroxy-4H-1,2,4-triazole |
| "A71" | 5-{2,4-Dihydroxy-5-[N-(2-aminoethoxybenzyl)-N-methyl-aminocarbonyl]phenyl}-4-(2-fluorophenyl)-3-hydroxy-4H-1,2,4-triazole |
| "A72" | 5-{2,4-Dihydroxy-5-[N-(2-hydroxyethoxybenzyl)-N-methyl-aminocarbonyl]phenyl}-4-(2-methylphenyl)-3-hydroxy-4H-1,2,4-triazole |
| "A73" | 5-{2,4-Dihydroxy-5-[N-(2-hydroxyethoxybenzyl)-N-methyl-aminocarbonyl]phenyl}-4-(2-chlorophenyl)-3-hydroxy-4H-1,2,4-triazole |
| "A74" | 5-{2,4-Dihydroxy-5-[N-(2-hydroxyethoxybenzyl)-N-methyl-aminocarbonyl]phenyl}-4-(2-fluorophenyl)-3-hydroxy-4H-1,2,4-triazole |
| "A75" | |
| "A76" | |
| "A77" | |

-continued

| Compound No. | Name and/or structure |
|---|---|
| "A78" | (structure) |
| "A79" | (structure) |
| "A80" | (structure) |
| "A81" | 5-{2,4-Dihydroxy-5-[N-(1-methylpyrrol-2-ylmethyl)-N-methyl-aminocarbonyl]phenyl}-4-(2-methylphenyl)-3-hydroxy-4H-1,2,4-triazole (structure) |
| "A82" | 5-{2,4-Dihydroxy-5-[N-(1-methylpyrrol-2-ylmethyl)-N-methyl-aminocarbonyl]phenyl}-4-(2-chlorophenyl)-3-hydroxy-4H-1,2,4-triazole |
| "A83" | 5-{2,4-Dihydroxy-5-[N-(1-methylpyrrol-2-ylmethyl)-N-methyl-aminocarbonyl]phenyl}-4-(2-fluorophenyl)-3-hydroxy-4H-1,2,4-triazole |
| "A84" | 5-{2,4-Dihydroxy-5-[N-(isoxazol-3-ylmethyl)-N-methyl-aminocarbonyl]phenyl}-4-(2-methylphenyl)-3-hydroxy-4H-1,2,4-triazole |
| "A85" | 5-{2,4-Dihydroxy-5-[N-(isoxazol-3-ylmethyl)-N-methyl-aminocarbonyl]phenyl}-4-(2-chlorophenyl)-3-hydroxy-4H-1,2,4-triazole |
| "A86" | 5-{2,4-Dihydroxy-5-[N-(isoxazol-3-ylmethyl)-N-methyl-aminocarbonyl]phenyl}-4-(2-fluorophenyl)-3-hydroxy-4H-1,2,4-triazole |
| "A87" | 5-{2,4-Dihydroxy-5-[N-(pyridazin-3-ylmethyl)-N-methyl-aminocarbonyl]phenyl}-4-(2-methylphenyl)-3-hydroxy-4H-1,2,4-triazole |
| "A88" | 5-{2,4-Dihydroxy-5-[N-(pyridazin-3-ylmethyl)-N-methyl-aminocarbonyl]phenyl}-4-(2-chlorophenyl)-3-hydroxy-4H-1,2,4-triazole |

-continued

| Compound No. | Name and/or structure |
|---|---|
| "A89" | 5-{2,4-Dihydroxy-5-[N-(pyridazin-3-ylmethyl)-N-methyl-aminocarbonyl]phenyl}-4-(2-fluorophenyl)-3-hydroxy-4H-1,2,4-triazole |
| "A90" | 5-{2,4-Dihydroxy-5-[N-(pyrazin-2-ylmethyl)-N-methyl-aminocarbonyl]phenyl}-4-(2-methylphenyl)-3-hydroxy-4H-1,2,4-triazole |
| "A91" | 5-{2,4-Dihydroxy-5-[N-(pyrazin-2-ylmethyl)-N-methyl-aminocarbonyl]phenyl}-4-(2-chlorophenyl)-3-hydroxy-4H-1,2,4-triazole |
| "A92" | 5-{2,4-Dihydroxy-5-[N-(pyrazin-2-ylmethyl)-N-methyl-aminocarbonyl]phenyl}-4-(2-fluorophenyl)-3-hydroxy-4H-1,2,4-triazole |
| "A93" | 5-{2,4-Dihydroxy-5-[N-(2-aminocarbonyl-5-chlorobenzyl)-N-methylaminocarbonyl]phenyl}-4-(2-methylphenyl)-3-hydroxy-4H-1,2,4-triazole |
| "A94" | 5-{2,4-Dihydroxy-5-[N-(2-aminocarbonyl-5-chlorobenzyl)-N-methylaminocarbonyl]phenyl}-4-(2-chlorophenyl)-3-hydroxy-4H-1,2,4-triazole |
| "A95" | 5-{2,4-Dihydroxy-5-[N-(2-aminocarbonyl-5-chlorobenzyl)-N-methylaminocarbonyl]phenyl}-4-(2-fluorophenyl)-3-hydroxy-4H-1,2,4-triazole |
| "A96" | 5-(2,4-Dihydroxy-5-{N-[3-(2-methylaminoethoxy)benzyl]-N-methylaminocarbonyl}phenyl)-4-(2-methylphenyl)-3-hydroxy-4H-1,2,4-triazole (structure) |
| "A97" | 5-(2,4-Dihydroxy-5-{N-[3-(2-methylaminoethoxy)benzyl]-N-methylaminocarbonyl}phenyl)-4-(2-chlorophenyl)-3-hydroxy-4H-1,2,4-triazole |
| "A98" | 5-(2,4-Dihydroxy-5-{N-[3-(2-methylaminoethoxy)benzyl]-N-methylaminocarbonyl}phenyl)-4-(2-fluorophenyl)-3-hydroxy-4H-1,2,4-triazole |
| "A99" | 5-{2,4-Dihydroxy-5-[N-(2,3-dimethoxybenzyl)-N-methyl-aminocarbonyl]phenyl}-4-(2-methylphenyl)-3-hydroxy-4H-1,2,4-triazole |
| "A100" | 5-{2,4-Dihydroxy-5-[N-(2,3-dimethoxybenzyl)-N-methyl-aminocarbonyl]phenyl}-4-(2-chlorophenyl)-3-hydroxy-4H-1,2,4-triazole |
| "A101" | 5-{2,4-Dihydroxy-5-[N-(2,3-dimethoxybenzyl)-N-methyl-aminocarbonyl]phenyl}-4-(2-fluorophenyl)-3-hydroxy-4H-1,2,4-triazole |
| "A102" | 5-(2,4-Dihydroxy-5-{N-[2-(2-cyanoethoxy)benzyl]-N-methyl-aminocarbonyl}phenyl)-4-(2-methylphenyl)-3-hydroxy-4H-1,2,4-triazole |
| "A103" | 5-(2,4-Dihydroxy-5-{N-[2-(2-cyanoethoxy)benzyl]-N-methyl-aminocarbonyl}phenyl)-4-(2-chlorophenyl)-3-hydroxy-4H-1,2,4-triazole |
| "A104" | 5-(2,4-Dihydroxy-5-{N-[2-(2-cyanoethoxy)benzyl]-N-methyl-aminocarbonyl}phenyl)-4-(2-fluorophenyl)-3-hydroxy-4H-1,2,4-triazole |
| "A105" | 5-{2,4-Dihydroxy-5-[N-(4-fluorobenzyl)-N-methyl-aminocarbonyl]phenyl}-4-(2-methylaminomethylphenyl)-3-hydroxy-4H-1,2,4-triazole |
| "A106" | 5-{2,4-Dihydroxy-5-[N-(4-fluorobenzyl)-N-methyl-aminocarbonyl]phenyl}-4-(3-aminomethylphenyl)-3-hydroxy-4H-1,2,4-triazole |
| "A107" | 5-[2,4-Dihydroxy-5-(N-benzyl-N-methylaminocarbonyl) phenyl]-4-(2-cyanophenyl)-3-hydroxy-4H-1,2,4-triazole |
| "A108" | 5-[2,4-Dihydroxy-5-(N-benzyl-N-methylaminocarbonyl) phenyl]-4-(2-ethylphenyl)-3-hydroxy-4H-1,2,4-triazole |
| "A109" | 5-{2,4-Dihydroxy-5-[N-(benzo-1,4-dioxan-5-yl)-N-methyl-aminocarbonyl]phenyl}-4-(2-methylphenyl)-3-hydroxy-4H-1,2,4-triazole |

-continued

| Compound No. | Name and/or structure |
|---|---|
| "A110" | 5-{2,4-Dihydroxy-5-[N-(2-isopropylbenzyl)-N-methyl-aminocarbonyl]phenyl}-4-(2-chlorophenyl)-3-hydroxy-4H-1,2,4-triazole |
| "A111" | 5-{2,4-Dihydroxy-5-[N-(2-aminomethylbenzyl)-N-methyl-aminocarbonyl]phenyl}-4-(2-chlorophenyl)-3-hydroxy-4H-1,2,4-triazole |
| "A112" | 5-{2,4-Dihydroxy-5-[N-(2-methylaminomethylbenzyl)-N-methyl-aminocarbonyl]phenyl}-4-(2-chlorophenyl)-3-hydroxy-4H-1,2,4-triazole |
| "A113" | 5-(2,4-Dihydroxy-5-{N-[2-(2-methoxyethoxy)benzyl]-N-methyl-aminocarbonyl}phenyl)-4-(2-chlorophenyl)-3-hydroxy-4H-1,2,4-triazole |
| "A114" | 5-{2,4-Dihydroxy-5-[N-(2-isopropylaminomethylbenzyl)-N-methylaminocarbonyl]phenyl}-4-(2-methylphenyl)-3-hydroxy-4H-1,2,4-triazole |
| "A115" | 5-[2,4-Dihydroxy-5-(N-benzyl-N-methylaminocarbonyl)phenyl]-4-[4-(3-cyanopropoxy)phenyl]-3-hydroxy-4H-1,2,4-triazole |
| "A116" | 5-{2,4-Dihydroxy-5-[N-(2-aminomethylbenzyl)-N-methyl-aminocarbonyl]phenyl}-4-(2-fluorophenyl)-3-hydroxy-4H-1,2,4-triazole |
| "A116a" | 5-[2-Hydroxy-4-methoxy-5-(N-benzyl-N-methylaminocarbonyl)-phenyl]-4-(2-methylphenyl)-3-hydroxy-4H-1,2,4-triazole |
| "A116b" | 2,4-Dihydroxy-N-methyl-5-(5-oxo-4-o-tolyl-4,5-dihydro-1H-1,2,4-triazol-3-yl)-N-(2-pyridin-3-ylbenzyl)benzamide |
| "A116c" | 2,4-Dihydroxy-N-methyl-N-[3-(2-morpholin-4-ylethoxy)benzyl]-5-(5-oxo-4-o-tolyl-4,5-dihydro-1H-1,2,4-triazol-3-yl)benzamide |
| "A116d" | 2,4-Dihydroxy-N-methyl-5-(5-oxo-4-o-tolyl-4,5-dihydro-1H-1,2,4-triazol-3-yl)-N-(3-pyrimidin-5-ylbenzyl)benzamide |
| "A117" | 5-{2,4-Dihydroxy-5-[N-(2-aminomethylbenzyl)-N-methyl-aminocarbonyl]phenyl}-4-(2-methylphenyl)-3-hydroxy-4H-1,2,4-triazole |
| "A117a" | 5-[2,4-Dihydroxy-5-(N-propyl-N-methylsulfamoyl)phenyl]-4-(2-chlorophenyl)-3-hydroxy-4H-1,2,4-triazole |
| "A118" | 5-{2,4-Dihydroxy-5-[N-(2-methoxybenzyl)-N-methyl-aminosulfonyl]phenyl}-4-(2-methylphenyl)-3-hydroxy-4H-1,2,4-triazole |
| "A119" | 5-{2,4-Dihydroxy-5-[N-(2-methoxybenzyl)-N-methyl-aminosulfonyl]phenyl}-4-(2-chlorophenyl)-3-hydroxy-4H-1,2,4-triazole |
| "A120" | 5-{2,4-Dihydroxy-5-[N-(2-methoxybenzyl)-N-methyl-aminosulfonyl]phenyl}-4-(2-fluorophenyl)-3-hydroxy-4H-1,2,4-triazole |
| "A121" | 5-{2,4-Dihydroxy-5-[N-(2-fluorobenzyl)-N-methyl-aminosulfonyl]phenyl}-4-(2-methylphenyl)-3-hydroxy-4H-1,2,4-triazole |
| "A122" | 5-{2,4-Dihydroxy-5-[N-(2-fluorobenzyl)-N-methyl-aminosulfonyl]phenyl}-4-(2-chlorophenyl)-3-hydroxy-4H-1,2,4-triazole |
| "A123" | 5-{2,4-Dihydroxy-5-[N-(2-fluorobenzyl)-N-methyl-aminosulfonyl]phenyl}-4-(2-fluorophenyl)-3-hydroxy-4H-1,2,4-triazole |
| "A124" | 5-{2,4-Dihydroxy-5-[N-(4-fluorobenzyl)-N-methyl-aminosulfonyl]phenyl}-4-(2-methylphenyl)-3-hydroxy-4H-1,2,4-triazole |
| "A125" | 5-{2,4-Dihydroxy-5-[N-(4-fluorobenzyl)-N-methyl-aminosulfonyl]phenyl}-4-(2-chlorophenyl)-3-hydroxy-4H-1,2,4-triazole |
| "A126" | 5-{2,4-Dihydroxy-5-[N-(4-fluorobenzyl)-N-methyl-aminosulfonyl]phenyl}-4-(2-fluorophenyl)-3-hydroxy-4H-1,2,4-triazole |
| "A127" | 5-{2,4-Dihydroxy-5-[N-(3-fluorobenzyl)-N-methyl-aminosulfonyl]phenyl}-4-(2-methylphenyl)-3-hydroxy-4H-1,2,4-triazole |
| "A128" | 5-{2,4-Dihydroxy-5-[N-(3-fluorobenzyl)-N-methyl-aminosulfonyl]phenyl}-4-(2-chlorophenyl)-3-hydroxy-4H-1,2,4-triazole |
| "A129" | 5-{2,4-Dihydroxy-5-[N-(3-fluorobenzyl)-N-methyl-aminosulfonyl]phenyl}-4-(2-fluorophenyl)-3-hydroxy-4H-1,2,4-triazole |
| "A130" | 5-{2,4-Dihydroxy-5-[N-(3-methylbenzyl)-N-methyl-aminosulfonyl]phenyl}-4-(2-methylphenyl)-3-hydroxy-4H-1,2,4-triazole |
| "A131" | 5-{2,4-Dihydroxy-5-[N-(3-methylbenzyl)-N-methyl-aminosulfonyl]phenyl}-4-(2-chlorophenyl)-3-hydroxy-4H-1,2,4-triazole |
| "A132" | 5-{2,4-Dihydroxy-5-[N-(3-methylbenzyl)-N-methyl-aminosulfonyl]phenyl}-4-(2-fluorophenyl)-3-hydroxy-4H-1,2,4-triazole |

| Compound No. | Name and/or structure |
|---|---|
| "A133" | 5-{2,4-Dihydroxy-5-[N-(4-methylbenzyl)-N-methyl-aminosulfonyl]phenyl}-4-(2-methylphenyl)-3-hydroxy-4H-1,2,4-triazole |
| "A134" | 5-{2,4-Dihydroxy-5-[N-(4-methylbenzyl)-N-methyl-aminosulfonyl]phenyl}-4-(2-chlorophenyl)-3-hydroxy-4H-1,2,4-triazole |
| "A135" | 5-{2,4-Dihydroxy-5-[N-(4-methylbenzyl)-N-methyl-aminosulfonyl]phenyl}-4-(2-fluorophenyl)-3-hydroxy-4H-1,2,4-triazole |
| "A136" | 5-{2,4-Dihydroxy-5-[N-(3-chlorobenzyl)-N-methyl-aminosulfonyl]phenyl}-4-(2-methylphenyl)-3-hydroxy-4H-1,2,4-triazole |
| "A137" | 5-{2,4-Dihydroxy-5-[N-(3-chlorobenzyl)-N-methyl-aminosulfonyl]phenyl}-4-(2-chlorophenyl)-3-hydroxy-4H-1,2,4-triazole |
| "A138" | 5-{2,4-Dihydroxy-5-[N-(3-chlorobenzyl)-N-methyl-aminosulfonyl]phenyl}-4-(2-fluorophenyl)-3-hydroxy-4H-1,2,4-triazole |
| "A139" | 5-{2,4-Dihydroxy-5-[N-(2-chlorobenzyl)-N-methyl-aminosulfonyl]phenyl}-4-(2-methylphenyl)-3-hydroxy-4H-1,2,4-triazole |
| "A140" | 5-{2,4-Dihydroxy-5-[N-(2-chlorobenzyl)-N-methyl-aminosulfonyl]phenyl}-4-(2-chlorophenyl)-3-hydroxy-4H-1,2,4-triazole |
| "A141" | 5-{2,4-Dihydroxy-5-[N-(2-chlorobenzyl)-N-methyl-aminosulfonyl]phenyl}-4-(2-fluorophenyl)-3-hydroxy-4H-1,2,4-triazole |
| "A142" | 5-{2,4-Dihydroxy-5-[N-(pyridin-2-ylmethyl)-N-methyl-aminosulfonyl]phenyl}-4-(2-methylphenyl)-3-hydroxy-4H-1,2,4-triazole |
| "A143" | 5-{2,4-Dihydroxy-5-[N-(pyridin-2-ylmethyl)-N-methyl-aminosulfonyl]phenyl}-4-(2-chlorophenyl)-3-hydroxy-4H-1,2,4-triazole |
| "A144" | 5-{2,4-Dihydroxy-5-[N-(pyridin-2-ylmethyl)-N-methyl-aminosulfonyl]phenyl}-4-(2-fluorophenyl)-3-hydroxy-4H-1,2,4-triazole |
| "A145" | 5-{2,4-Dihydroxy-5-[N-(pyridin-3-ylmethyl)-N-methyl-aminosulfonyl]phenyl}-4-(2-methylphenyl)-3-hydroxy-4H-1,2,4-triazole |
| "A146" | 5-{2,4-Dihydroxy-5-[N-(pyridin-3-ylmethyl)-N-methyl-aminosulfonyl]phenyl}-4-(2-chlorophenyl)-3-hydroxy-4H-1,2,4-triazole |
| "A147" | 5-{2,4-Dihydroxy-5-[N-(pyridin-3-ylmethyl)-N-methyl-aminosulfonyl]phenyl}-4-(2-fluorophenyl)-3-hydroxy-4H-1,2,4-triazole |
| "A148" | 5-{2,4-Dihydroxy-5-[N-(pyridin-4-ylmethyl)-N-methyl-aminosulfonyl]phenyl}-4-(2-methylphenyl)-3-hydroxy-4H-1,2,4-triazole |
| "A149" | 5-{2,4-Dihydroxy-5-[N-(pyridin-4-ylmethyl)-N-methyl-aminosulfonyl]phenyl}-4-(2-chlorophenyl)-3-hydroxy-4H-1,2,4-triazole |
| "A150" | 5-{2,4-Dihydroxy-5-[N-(pyridin-4-ylmethyl)-N-methyl-aminosulfonyl]phenyl}-4-(2-fluorophenyl)-3-hydroxy-4H-1,2,4-triazole |
| "A151" | 5-{2,4-Dihydroxy-5-[N-(1-oxypyridin-2-ylmethyl)-N-methyl-aminosulfonyl]phenyl}-4-(2-methylphenyl)-3-hydroxy-4H-1,2,4-triazole |
| "A152" | 5-{2,4-Dihydroxy-5-[N-(1-oxypyridin-2-ylmethyl)-N-methyl-aminosulfonyl]phenyl}-4-(2-chlorophenyl)-3-hydroxy-4H-1,2,4-triazole |
| "A153" | 5-{2,4-Dihydroxy-5-[N-(1-oxypyridin-2-ylmethyl)-N-methyl-aminosulfonyl]phenyl}-4-(2-fluorophenyl)-3-hydroxy-4H-1,2,4-triazole |
| "A154" | 5-{2,4-Dihydroxy-5-[N-(1-oxypyridin-3-ylmethyl)-N-methyl-aminosulfonyl]phenyl}-4-(2-methylphenyl)-3-hydroxy-4H-1,2,4-triazole |
| "A155" | 5-{2,4-Dihydroxy-5-[N-(1-oxypyridin-3-ylmethyl)-N-methyl-aminosulfonyl]phenyl}-4-(2-chlorophenyl)-3-hydroxy-4H-1,2,4-triazole |
| "A156" | 5-{2,4-Dihydroxy-5-[N-(1-oxypyridin-3-ylmethyl)-N-methyl-aminosulfonyl]phenyl}-4-(2-fluorophenyl)-3-hydroxy-4H-1,2,4-triazole |
| "A157" | 5-{2,4-Dihydroxy-5-[N-(1-oxypyridin-4-ylmethyl)-N-methyl-aminosulfonyl]phenyl}-4-(2-methylphenyl)-3-hydroxy-4H-1,2,4-triazole |
| "A158" | 5-{2,4-Dihydroxy-5-[N-(1-oxypyridin-4-ylmethyl)-N-methyl-aminosulfonyl]phenyl}-4-(2-chlorophenyl)-3-hydroxy-4H-1,2,4-triazole |
| "A159" | 5-{2,4-Dihydroxy-5-[N-(1-oxypyridin-4-ylmethyl)-N-methyl-aminosulfonyl]phenyl}-4-(2-fluorophenyl)-3-hydroxy-4H-1,2,4-triazole |
| "A160" | 5-{2,4-Dihydroxy-5-[N-(2-chloro-6-fluorobenzyl)-N-methyl-aminosulfonyl]phenyl}-4-(2-methylphenyl)-3-hydroxy-4H-1,2,4-triazole |
| "A161" | 5-{2,4-Dihydroxy-5-[N-(2-chloro-6-fluorobenzyl)-N-methyl-aminosulfonyl]phenyl}-4-(2-chlorophenyl)-3-hydroxy-4H-1,2,4-triazole |
| "A162" | 5-{2,4-Dihydroxy-5-[N-(2-chloro-6-fluorobenzyl)-N-methyl-aminosulfonyl]phenyl}-4-(2-fluorophenyl)-3-hydroxy-4H-1,2,4-triazole |
| "A163" | 5-{2,4-Dihydroxy-5-[N-(3-chloro-6-methoxybenzyl)-N-methyl-aminosulfonyl]phenyl}-4-(2-methylphenyl)-3-hydroxy-4H-1,2,4-triazole |
| "A164" | 5-{2,4-Dihydroxy-5-[N-(3-chloro-6-methoxybenzyl)-N-methyl-aminosulfonyl]phenyl}-4-(2-chlorophenyl)-3-hydroxy-4H-1,2,4-triazole |
| "A165" | 5-{2,4-Dihydroxy-5-[N-(3-chloro-6-methoxybenzyl)-N-methyl-aminosulfonyl]phenyl}-4-(2-fluorophenyl)-3-hydroxy-4H-1,2,4-triazole |
| "A166" | 5-{2,4-Dihydroxy-5-[N-(3-fluoro-6-methoxybenzyl)-N-methyl-aminosulfonyl]phenyl}-4-(2-methylphenyl)-3-hydroxy-4H-1,2,4-triazole |
| "A167" | 5-{2,4-Dihydroxy-5-[N-(3-fluoro-6-methoxybenzyl)-N-methyl-aminosulfonyl]phenyl}-4-(2-chlorophenyl)-3-hydroxy-4H-1,2,4-triazole |
| "A168" | 5-{2,4-Dihydroxy-5-[N-(3-fluoro-6-methoxybenzyl)-N-methyl-aminosulfonyl]phenyl}-4-(2-fluorophenyl)-3-hydroxy-4H-1,2,4-triazole |
| "A169" | 5-{2,4-Dihydroxy-5-[N-(2,3-dimethoxybenzyl)-N-methyl-aminosulfonyl]phenyl}-4-(2-methylphenyl)-3-hydroxy-4H-1,2,4-triazole |
| "A170" | 5-{2,4-Dihydroxy-5-[N-(2,3-dimethoxybenzyl)-N-methyl-aminosulfonyl]phenyl}-4-(2-chlorophenyl)-3-hydroxy-4H-1,2,4-triazole |
| "A171" | 5-{2,4-Dihydroxy-5-[N-(2,3-dimethoxybenzyl)-N-methyl-aminosulfonyl]phenyl}-4-(2-fluorophenyl)-3-hydroxy-4H-1,2,4-triazole |
| "A172" | 5-{2,4-Dihydroxy-5-[N-(furan-2-ylmethyl)-N-methyl-aminosulfonyl]phenyl}-4-(2-methylphenyl)-3-hydroxy-4H-1,2,4-triazole |
| "A173" | 5-{2,4-Dihydroxy-5-[N-(furan-2-ylmethyl)-N-methyl-aminosulfonyl]phenyl}-4-(2-chlorophenyl)-3-hydroxy-4H-1,2,4-triazole |
| "A174" | 5-{2,4-Dihydroxy-5-[N-(furan-2-ylmethyl)-N-methyl-aminosulfonyl]phenyl}-4-(2-fluorophenyl)-3-hydroxy-4H-1,2,4-triazole |
| "A175" | 5-{2,4-Dihydroxy-5-[N-(furan-3-ylmethyl)-N-methyl-aminosulfonyl]phenyl}-4-(2-methylphenyl)-3-hydroxy-4H-1,2,4-triazole |
| "A176" | 5-{2,4-Dihydroxy-5-[N-(furan-3-ylmethyl)-N-methyl-aminosulfonyl]phenyl}-4-(2-chlorophenyl)-3-hydroxy-4H-1,2,4-triazole |
| "A177" | 5-{2,4-Dihydroxy-5-[N-(furan-3-ylmethyl)-N-methyl-aminosulfonyl]phenyl}-4-(2-fluorophenyl)-3-hydroxy-4H-1,2,4-triazole |
| "A178" | 5-(2,4-Dihydroxy-5-{N-[2-(2-dimethylaminoethoxy)benzyl]-N-methylaminosulfonyl}phenyl)-4-(2-methylphenyl)-3-hydroxy-4H-1,2,4-triazole |
| "A179" | 5-(2,4-Dihydroxy-5-{N-[2-(2-dimethylaminoethoxy)benzyl]-N-methylaminosulfonyl}phenyl)-4-(2-chlorophenyl)-3-hydroxy-4H-1,2,4-triazole |
| "A180" | 5-(2,4-Dihydroxy-5-{N-[2-(2-dimethylaminoethoxy)benzyl]-N-methylaminosulfonyl}phenyl)-4-(2-fluorophenyl)-3-hydroxy-4H-1,2,4-triazole |
| "A181" | 5-(2,4-Dihydroxy-5-{N-[2-(2-methylaminoethoxy)benzyl]-N-methylaminosulfonyl}phenyl)-4-(2-methylphenyl)-3-hydroxy-4H-1,2,4-triazole |

| Compound No. | Name and/or structure |
|---|---|
| "A182" | 5-(2,4-Dihydroxy-5-{N-[2-(2-methylaminoethoxy)benzyl]-N-methylaminosulfonyl}phenyl)-4-(2-chlorophenyl)-3-hydroxy-4H-1,2,4-triazole |
| "A183" | 5-(2,4-Dihydroxy-5-{N-[2-(2-methylaminoethoxy)benzyl]-N-methylaminosulfonyl}phenyl)-4-(2-fluorophenyl)-3-hydroxy-4H-1,2,4-triazole |
| "A184" | 5-(2,4-Dihydroxy-5-{N-[2-(2-aminoethoxy)benzyl]-N-methyl-aminosulfonyl}phenyl)-4-(2-methylphenyl)-3-hydroxy-4H-1,2,4-triazole |
| "A185" | 5-(2,4-Dihydroxy-5-{N-[2-(2-aminoethoxy)benzyl]-N-methyl-aminosulfonyl}phenyl)-4-(2-chlorophenyl)-3-hydroxy-4H-1,2,4-triazole |
| "A186" | 5-(2,4-Dihydroxy-5-{N-[2-(2-aminoethoxy)benzyl]-N-methyl-aminosulfonyl}phenyl)-4-(2-fluorophenyl)-3-hydroxy-4H-1,2,4-triazole |
| "A187" | 5-(2,4-Dihydroxy-5-{N-[2-(2-hydroxyethoxy)benzyl]-N-methyl-aminosulfonyl}phenyl)-4-(2-methylphenyl)-3-hydroxy-4H-1,2,4-triazole |
| "A188" | 5-(2,4-Dihydroxy-5-{N-[2-(2-hydroxyethoxy)benzyl]-N-methyl-aminosulfonyl}phenyl)-4-(2-chlorophenyl)-3-hydroxy-4H-1,2,4-triazole |
| "A189" | 5-(2,4-Dihydroxy-5-{N-[2-(2-hydroxyethoxy)benzyl]-N-methyl-aminosulfonyl}phenyl)-4-(2-fluorophenyl)-3-hydroxy-4H-1,2,4-triazole |
| "A190" | 5-(2,4-Dihydroxy-5-{N-[2-(2-isopropylaminoethoxy)benzyl]-N-methylaminosulfonyl}phenyl)-4-(2-methylphenyl)-3-hydroxy-4H-1,2,4-triazole |
| "A191" | 5-(2,4-Dihydroxy-5-{N-[2-(2-isopropylaminoethoxy)benzyl]-N-methylaminosulfonyl}phenyl)-4-(2-chlorophenyl)-3-hydroxy-4H-1,2,4-triazole |
| "A192" | 5-(2,4-Dihydroxy-5-{N-[2-(2-isopropylaminoethoxy)benzyl]-N-methylaminosulfonyl}phenyl)-4-(2-fluorophenyl)-3-hydroxy-4H-1,2,4-triazole |
| "A193" | 5-(2,4-Dihydroxy-5-{N-[2-(carbamoylmethoxy)benzyl]-N-methyl-aminosulfonyl}phenyl)-4-(2-methylphenyl)-3-hydroxy-4H-1,2,4-triazole |
| "A194" | 5-(2,4-Dihydroxy-5-{N-[2-(carbamoylmethoxy)benzyl]-N-methyl-aminosulfonyl}phenyl)-4-(2-chlorophenyl)-3-hydroxy-4H-1,2,4-triazole |
| "A195" | 5-(2,4-Dihydroxy-5-{N-[2-(carbamoylmethoxy)benzyl]-N-methyl-aminosulfonyl}phenyl)-4-(2-fluorophenyl)-3-hydroxy-4H-1,2,4-triazole |
| "A196" | 5-{2,4-Dihydroxy-5-[N-(1-methylpyrrol-2-ylmethyl)-N-methyl-aminosulfonyl]phenyl}-4-(2-methylphenyl)-3-hydroxy-4H-1,2,4-triazole |
| "A197" | 5-{2,4-Dihydroxy-5-[N-(1-methylpyrrol-2-ylmethyl)-N-methyl-aminosulfonyl]phenyl}-4-(2-chlorophenyl)-3-hydroxy-4H-1,2,4-triazole |
| "A198" | 5-{2,4-Dihydroxy-5-[N-(1-methylpyrrol-2-ylmethyl)-N-methyl-aminosulfonyl]phenyl}-4-(2-fluorophenyl)-3-hydroxy-4H-1,2,4-triazole |
| "A199" | 5-{2,4-Dihydroxy-5-[N-(isoxazol-3-ylmethyl)-N-methyl-aminosulfonyl]phenyl}-4-(2-methylphenyl)-3-hydroxy-4H-1,2,4-triazole |
| "A200" | 5-{2,4-Dihydroxy-5-[N-(isoxazol-3-ylmethyl)-N-methyl-aminosulfonyl]phenyl}-4-(2-chlorophenyl)-3-hydroxy-4H-1,2,4-triazole |
| "A201" | 5-{2,4-Dihydroxy-5-[N-(isoxazol-3-ylmethyl)-N-methyl-aminosulfonyl]phenyl}-4-(2-fluorophenyl)-3-hydroxy-4H-1,2,4-triazole |
| "A202" | 5-{2,4-Dihydroxy-5-[N-(pyridazin-3-ylmethyl)-N-methyl-aminosulfonyl]phenyl}-4-(2-methylphenyl)-3-hydroxy-4H-1,2,4-triazole |
| "A203" | 5-{2,4-Dihydroxy-5-[N-(pyridazin-3-ylmethyl)-N-methyl-aminosulfonyl]phenyl}-4-(2-chlorophenyl)-3-hydroxy-4H-1,2,4-triazole |
| "A204" | 5-{2,4-Dihydroxy-5-[N-(pyridazin-3-ylmethyl)-N-methyl-aminosulfonyl]phenyl}-4-(2-fluorophenyl)-3-hydroxy-4H-1,2,4-triazole |
| "A205" | 5-{2,4-Dihydroxy-5-[N-(pyrazin-2-ylmethyl)-N-methyl-aminosulfonyl]phenyl}-4-(2-methylphenyl)-3-hydroxy-4H-1,2,4-triazole |
| "A206" | 5-{2,4-Dihydroxy-5-[N-(pyrazin-2-ylmethyl)-N-methyl-aminosulfonyl]phenyl}-4-(2-chlorophenyl)-3-hydroxy-4H-1,2,4-triazole |
| "A207" | 5-{2,4-Dihydroxy-5-[N-(pyrazin-2-ylmethyl)-N-methyl-aminosulfonyl]phenyl}-4-(2-fluorophenyl)-3-hydroxy-4H-1,2,4-triazole |
| "A208" | 5-{2,4-Dihydroxy-5-[N-(2-carbamoyl-5-chlorobenzyl)-N-methyl-aminosulfonyl]phenyl}-4-(2-methylphenyl)-3-hydroxy-4H-1,2,4-triazole |
| "A209" | 5-{2,4-Dihydroxy-5-[N-(2-carbamoyl-5-chlorobenzyl)-N-methyl-aminosulfonyl]phenyl}-4-(2-chlorophenyl)-3-hydroxy-4H-1,2,4-triazole |
| "A210" | 5-{2,4-Dihydroxy-5-[N-(2-carbamoyl-5-chlorobenzyl)-N-methyl-aminosulfonyl]phenyl}-4-(2-fluorophenyl)-3-hydroxy-4H-1,2,4-triazole |
| "A211" | 5-(2,4-Dihydroxy-5-{N-[2-(2-methylaminoethoxy)benzyl]-N-methylaminosulfonyl}phenyl)-4-(2-methylphenyl)-3-hydroxy-4H-1,2,4-triazole |
| "A212" | 5-(2,4-Dihydroxy-5-{N-[2-(2-methylaminoethoxy)benzyl]-N-methylaminosulfonyl}phenyl)-4-(2-chlorophenyl)-3-hydroxy-4H-1,2,4-triazole |
| "A213" | 5-(2,4-Dihydroxy-5-{N-[2-(2-methylaminoethoxy)benzyl]-N-methylaminosulfonyl}phenyl)-4-(2-fluorophenyl)-3-hydroxy-4H-1,2,4-triazole |
| "A214" | 5-{2,4-Dihydroxy-5-[N-(2,3-dimethoxybenzyl)-N-methyl-aminosulfonyl]phenyl}-4-(2-methylphenyl)-3-hydroxy-4H-1,2,4-triazole |
| "A215" | 5-{2,4-Dihydroxy-5-[N-(2,3-dimethoxybenzyl)-N-methyl-aminosulfonyl]phenyl}-4-(2-chlorophenyl)-3-hydroxy-4H-1,2,4-triazole |
| "A216" | 5-{2,4-Dihydroxy-5-[N-(2,3-dimethoxybenzyl)-N-methyl-aminosulfonyl]phenyl}-4-(2-fluorophenyl)-3-hydroxy-4H-1,2,4-triazole |
| "A217" | 5-(2,4-Dihydroxy-5-{N-[2-(2-cyanoethoxy)benzyl]-N-methyl-aminosulfonyl}phenyl)-4-(2-methylphenyl)-3-hydroxy-4H-1,2,4-triazole |
| "A218" | 5-(2,4-Dihydroxy-5-{N-[2-(2-cyanoethoxy)benzyl]-N-methyl-aminosulfonyl}phenyl)-4-(2-chlorophenyl)-3-hydroxy-4H-1,2,4-triazole |
| "A219" | 5-(2,4-Dihydroxy-5-{N-[2-(2-cyanoethoxy)benzyl]-N-methyl-aminosulfonyl}phenyl)-4-(2-fluorophenyl)-3-hydroxy-4H-1,2,4-triazole |
| "A220" | 5-{2,4-Dihydroxy-5-[N-(4-fluorobenzyl)-N-methyl-aminosulfonyl]phenyl}-4-(2-methylaminomethylphenyl)-3-hydroxy-4H-1,2,4-triazole |
| "A221" | 5-{2,4-Dihydroxy-5-[N-(4-fluorobenzyl)-N-methyl-aminosulfonyl]phenyl}-4-(2-aminomethylphenyl)-3-hydroxy-4H-1,2,4-triazole | or pharmaceutically usable salts, tautomers or stereoisomers thereof, including mixtures thereof in all ratios.

21. A compounds of the formula

| "A222" | 5-[2,4-Dihydroxy-5-(N-benzyl-N-methylaminosulfonyl)phenyl]-4-(2-cyanophenyl)-3-hydroxy-4H-1,2,4-triazole |
| --- | --- |
| "A223" | 5-[2,4-Dihydroxy-5-(N-benzyl-N-methylaminosulfonyl)phenyl]-4-(2-cyanophenyl)-3-hydroxy-4H-1,2,4-triazole |
| "A224" | 5-[2,4-Dihydroxy-5-(N-benzyl-N-methylaminosulfonyl)phenyl]-4-{4-[2-(piperazin-4-yl)ethoxy]phenyl}-3-hydroxy-4H-1,2,4-triazole |
| "A225" | 5-[2,4-Dihydroxy-5-(N-benzyl-N-methylaminosulfonyl)phenyl]-4-phenyl-3-hydroxy-4H-1,2,4-triazole |
| "A226" | 5-[2,4-Dihydroxy-5-(N-benzyl-N-methylaminosulfonyl)phenyl]-4-(2-methylphenyl)-3-hydroxy-4H-1,2,4-triazole |
| "A227" | 5-[2,4-Dihydroxy-5-(N-benzyl-N-methylaminosulfonyl)phenyl]-4-(2-chlorophenyl)-3-hydroxy-4H-1,2,4-triazole |
| "A228" | 5-[2,4-Dihydroxy-5-(N-benzyl-N-methylaminosulfonyl)phenyl]-4-(2-fluorophenyl)-3-hydroxy-4H-1,2,4-triazole | or pharmaceutically usable salts, tautomers or stereoisomers thereof, including mixtures thereof in all ratios.

22. A process for the preparation of a compound of formula I according to claim 1 or pharmaceutically usable salts, tautomers or stereoisomers thereof, comprising reacting
a) a compound of the formula II

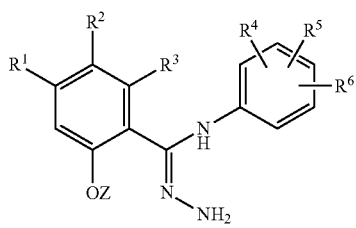

in which
$R^1$, $R^2$, $R^3$, $R^4$, $R^5$ and $R^6$ have the meanings indicated in claim 1, where $NH_2$ and/or OH groups are in protected form, and
Z denotes a hydroxyl-protecting group,
with
a compound of the formula III

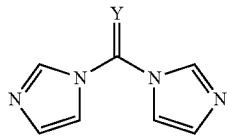

in which Y denotes O or S,
and subsequently removing the protecting groups,
or
b) reacting a compound of formula IV

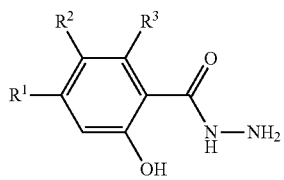

in which
$R^1$, $R^2$ and $R^3$ have the meanings indicated in claim 1,
with
a compound of formula V

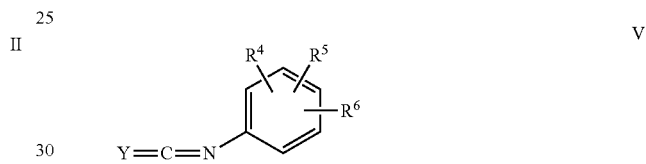

in which $R^4$, $R^5$ and $R^6$ have the meanings indicated in claim 1 and Y denotes O or S,
to give thiosemicarbazide derivatives, and subsequently cyclizing the latter,
and/or converting one or more radical(s) $R^1$, $R^2$, $R^3$, $R^4$, $R^5$ and/or $R^6$ in a compound of the formula I into one or more radical(s) $R^1$, $R^2$, $R^3$, $R^4$, $R^5$ and/or $R^6$
by
i) reducing a nitro group to an amino group,
ii) hydrolyzing an ester group to a carboxyl group,
iii) converting an amino group into an alkylated amine by reductive amination,
iv) converting an acid chloride into an amide,
and/or converting a base or acid of formula I into one of its salts.

23. A pharmaceutical composition comprising at least one compound of formula I according to claim 1,
and/or pharmaceutically usable salts, tautomers or stereoisomers thereof, including mixtures thereof in all ratios, and optionally excipients and/or adjuvants.

24. A kit consisting of separate packs of
(a) an effective amount of a compound of the formula I according to claim 1 and/or pharmaceutically usable salts, tautomers or stereoisomers thereof, including mixtures thereof in all ratios,
and
(b) an effective amount of a further medicament active ingredient.

* * * * *

UNITED STATES PATENT AND TRADEMARK OFFICE
CERTIFICATE OF CORRECTION

PATENT NO. : 8,119,795 B2
APPLICATION NO. : 12/301140
DATED : February 21, 2012
INVENTOR(S) : Eggenweiler et al.

Page 1 of 1

It is certified that error appears in the above-identified patent and that said Letters Patent is hereby corrected as shown below:

In the claims

Column 65, line 20 reads "$O(CH_2)_oHet, O(CH_2)_oNH_2, O(CH_2)_o CN, OA, Het$'" SHOULD READ -- $O(CH_2)_oHet, O(CH_2)_oNH_2, O(CH_2)_o CN, OA, OHet'$ --

Column 65, line 23 reads "$(Ar)_2$ or $SO_2N(Hd)_2$," SHOULD READ -- $(Ar)_2$ or $SO_2N(Het')_2$, --

Column 75, A78 reads " 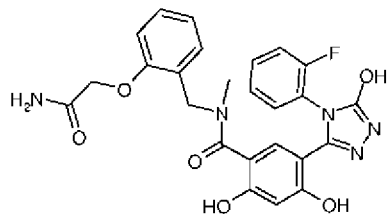 " SHOULD READ

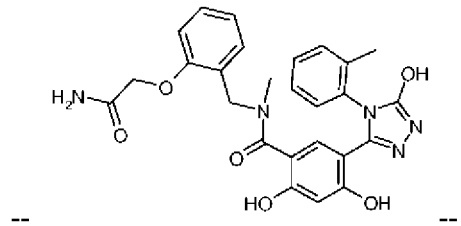

--

Column 83, line 1 reads "A compounds of the formula" SHOULD READ -- A compound of the formula --

Signed and Sealed this
Twentieth Day of October, 2015

Michelle K. Lee
*Director of the United States Patent and Trademark Office*